United States Patent [19]

Moyer et al.

[11] Patent Number: 5,721,352
[45] Date of Patent: *Feb. 24, 1998

[54] ENTOMOPOXVIRUS EXPRESSION SYSTEM

[75] Inventors: Richard W. Moyer; Richard L. Hall, both of Gainesville, Fla.; Michael E. Gruidl, Columbia, Mo.

[73] Assignee: University of Florida Research Foundation, Gainesville, Fla.

[*] Notice: The term of this patent shall not extend beyond the expiration date of Pat. No. 5,476,781.

[21] Appl. No.: 107,755

[22] Filed: Nov. 22, 1993

Related U.S. Application Data

[63] Continuation-in-part of Ser. No. 827,685, Jan. 30, 1992, abandoned, which is a continuation-in-part of Ser. No. 657,584, Feb. 19, 1991, abandoned.

[51] Int. Cl.$^6$ .................................................. C07H 21/04
[52] U.S. Cl. ................................ 536/23.2; 536/23.72
[58] Field of Search ........................... 435/69.1, 320.1, 435/172.1, 172.3; 536/23.1, 23.2, 23.72; 530/350

[56] References Cited

U.S. PATENT DOCUMENTS 5,338,679  8/1994  Yuen et al. .......................... 435/235.1

FOREIGN PATENT DOCUMENTS 0397560  11/1990  European Pat. Off. .

OTHER PUBLICATIONS

Pearson et al. "The 5' Noncoding Region Sequence of the *Choristoneura biennis* Entomopoxvirus Spheroidin Gene Functions as an Efficient Late Promoter in the Mammalian Vaccinia Expression System" Virology, vol. 180, pp. 561–566, 1991.

Hall et al. "Identification, Cloning, and Sequencing of a Fragment of *Amsacta moorei* Entomopoxvirus DNA Containing the Spheroidin Gene and Three Vaccinia Virus Related Open Reading Frames", J. of Virol., vol. 65, No. 12, Dec. 1991, pp. 6516–6527.

Upton et al. "Identification and Nucleotide Sequence of the Thymidine Kinase Gene of Shope Fibroma Virus", J. of Virol., vol. 60, No. 3, Dec. 1986, pp. 920–927.

Chakrabarti et al. "Vaccinia Virus Expression Vector: Coexpression of β-Galactosidase Provides Visual Screening of Recombinant Virus Plaques", Mol. Cell. Biol., vol. 5, No. 12, Dec. 1985, pp. 3403–3409.

Roberts, D.W., R.R. Granados (1968) "A Poxlike Virus from *Amsecta moorei*" J. Intertebr. Pathol. 12:141–143.

Gradados, R.R., M. Naughton (1976) "Replication of *Amsacta moorei* Entomopoxvirus and *Autographa californica* Nuclear Polyhedrosis Virus in Hemocyte Cell Lines from *Estigmene acrea*" Invert. Tissue Culture App. in Medicine, Biology and Agriculture 379–389.

Hukuhara, Tosihiko et al. (1990) "Replicatin of an Entomopoxvirus in Two Lepidopteran Cell Lines" Journal of Invertebrate Pathology 56:222–232.

Sato, Takeru (1989) "Establishment of Eight Cell Lines from Neonate Larvae of Tortricids (Lepidoptera) and their Several Characteristics including Susceptibility to Insect Viruses" Invertebrate Cell Systems Applications II:187–198.

Langridge, W.H.R. et al. (1977) "The Base Composition of Entomopoxvirus DNA" Virology 76:616–620.

Hall, R.L., W.F. Hink (1990) "Physical mapping and field inversion gel electrophoresis of *Amsacta moorei* entomopoxvirus DNA" Arch. Virol. 110:77–90.

Langridge, W.H.R. (1983) "Detection of *Amsacta moorei* Entomopoxvirus and Vaccinia Virus Proteins in Cell Cultures Restrictive for Poxvirus Multiplication" Journal of Invertebrate Pathology 42:77–82.

Langridge, W.H.R. (1984) "Detection of DNA Base Sequence Homology between Entomopoxvirus Isolated from Lepidoptera and Orthoptera" J. Invert. Path. 43:41–46.

Langridge, W.H.R. et al. (1982) "Structural Proteins of *Amsacta Moorei, Euxoa auxiliaris*, and *Melanoplus sanguinipes* Entomopoxviruses" J. Invert. Path. 39:346–353.

Mackett, Michael et al. (1985) "The Construction and Characterisation of Vaccinia Virus Recombinants Expressing Foreign Genes" DNA Cloning II:191–212.

Panicalli, Dennis et al. (1982) "Construction of live vaccines by using genetically engineered poxviruses: Biological activity of recombinant vaccinia virus expressing influenza virus hemagglutinin" Proc.Natl.Acad.Sci.USA 80:5364–5368.

Paoletti, Enzo et al. (1984) "Construction of live vaccines using genetically engineered poxviruses: Biological activity of vaccinia virus recombinants expressing the hepatitis B virus surface antigen & the herpes simplex virus glycoprotein D" Proc.Natl.Acad.Sci.USA 81:193–197.

Piccini, A., E. Paoletti (1986) "The Use of Vaccinia Virus for the Construction of Recombinant Vaccines" BioEssays 5:248–252.

Yuen, Leonard et al. (1990) "Identification and Sequencing of the Spheroidin Gene of *Choristoneura biennis* Entomopoxvirus" Virology 175:427–433.

*Primary Examiner*—David Guzo
*Attorney, Agent, or Firm*—Saliwanchik, Lloyd & Saliwanchik

[57] ABSTRACT

The subject invention pertains to novel Entomopoxvirus (EPV) polynucleotide sequences free from association with other viral sequences with which they are naturally associated, recombinant polynucleotide vectors containing the sequences, recombinant viruses containing the sequences, and host cells infected with the recombinant viruses are provided herein, as well as methods for use thereof in the expression of heterologous proteins in both insect and mammalian host cells.

6 Claims, 15 Drawing Sheets

```
AGATCTGATG TTCTATATAT AGTACAAATT TGTATGATTA ATTGATATTT TAAAATTCAA      60

GATA TTA AAT ATT AGA TTC TAA ACT ATT CTT CTC ATT ATC AAT ATA ACT     109
     Ile Asn Ser Glu Leu Ser Asn Lys Glu Asn Asp Ile Tyr Ser
     1               5                   10

ATC ATA ATC ATT TTT TAT TTT ACT ACA TAC ATT CAT AAT TCT ATT ACT ATT  160
Asp Tyr Asp Asn Lys Ile Lys Ser Cys Val Asn Met Ile Arg Asn Ser Asn
15              20                  25                  30

TTT TTT ATA CAT ATC TAT TAA TTC CAT AAA CTT TTT ATT TTT TAT ATT AAA  211
Lys Lys Tyr Met Asp Ile Leu Glu Met Phe Lys Lys Asn Lys Ile Asn Phe
            35                  40                  45

TAT TTC TAA TGT ATT TTT AAA TTC GTC AAT ACT ATT AAT ATC ATA TCT AGA  262
Ile Glu Leu Thr Asn Lys Phe Glu Asp Ile Ser Asn Ile Asp Tyr Arg Ser
    50                  55                  60                  65

AAT AAA TAA TGC ACC TCT ATA ACT ACT AGC CAA TAA ATC ACC AAT AAA ACT  313
Ile Phe Leu Ala Gly Arg Tyr Ser Ser Ala Leu Leu Asp Gly Ile Phe Ser
                70                  75                  80

CAT AGA ATA ATA TAA TTT TTT AAA TTC AAA TTT AGA TTT TAT GTT GAA ATA  364
Met Ser Tyr Tyr Leu Lys Lys Phe Glu Phe Lys Ser Lys Ile Asn Phe Tyr
        85                  90                  95

AAC TAT ATA ATA TAA AAA TAT TAT ATT AAA CAT ACC ACA ATC GGG ACT ATC  415
Val Ile Tyr Tyr Leu Phe Ile Ile Asn Phe Met Gly Cys Asp Pro Ser Asp
100                 105                 110                 115

ATA TTG TAA TTC AAA AGT ATT AAA AAA GTA ATA ATT TAC ATT TTT AAA TAT  466
Tyr Gln Leu Glu Phe Thr Asn Phe Phe Tyr Tyr Asn Val Asn Lys Phe Ile
        120                 125                 130

ATC ATT TAA ATA TTC TGA TAG TAC ATC AAT GTA TAA ATA AGC ATA ATT AGT  517
Asp Asn Leu Tyr Glu Ser Leu Val Asp Ile Tyr Leu Tyr Ala Tyr Asn Thr
    135                 140                 145                 150

ATT AGG AGT ACT ATT GTA GTG TTT ATG GCT TTT TAT AGT CAT ATC AGA TTC  568
Asn Pro Thr Ser Asn Tyr His Lys His Ser Lys Ile Thr Met Asp Ser Glu
            155                 160                 165

AAT AAA CAT ATA TTT TTT ATT TTG TTT TAT AAG TTC TGG TAT ATA ACC ACT  619
Ile Phe Met Tyr Lys Lys Asn Gln Lys Ile Leu Glu Pro Ile Tyr Gly Ser
        170                 175                 180

ACT ATT AAA AAA GTA TGC AGC TTT TTT ATC TTT ATC AAA GTG TTT ATC TAT  670
Ser Asn Phe Phe Tyr Ala Ala Lys Lys Asp Lys Asp Phe His Lys Asp Ile
185                 190                 195                 200

TAC GCA ACA AGT AAA ATG ATC ATT ATA AAT TAT AGG AAA CAT AAA AAA TCT  721
Val Cys Cys Thr Phe His Asp Asn Tyr Ile Ile Pro Phe Met Phe Phe Arg
        205                 210                 215

TTT TTT ATC ATT CAT TAA AAA AAA TTT TAC TCT ATC TTC AAG TTT ATA GCA  772
Lys Lys Asp Asn Met Leu Phe Phe Lys Val Arg Asp Glu Leu Lys Tyr Cys
    220                 225                 230                 235

TCT CAT AGA TGA AGC TAC TGT AGC AAT ATT TTT ATC AGT TTT TTC AAA TAA  823
Arg Met Ser Ser Ala Val Thr Ala Ile Asn Lys Asp Thr Lys Glu Phe Leu
            240                 245                 250
```

FIG. 2A

```
AAT CAA ATG AAA ATA ATC ATA ATC TGT ATT AAT CAT AGT TAA TGG ATA TAT  874
Ile Leu His Phe Tyr Asp Tyr Asp Thr Asn Ile Met Thr Leu Pro Tyr Ile
        255             260             265

ACA ATT ATA TAT ATC TCC CGA ACT TAA CCA TGT AGA TTT ATC ATG TTT TCT  925
Cys Asn Tyr Ile Asp Gly Ser Ser Leu Trp Thr Ser Lys Asp His Lys Arg
270             275             280             285

TGG GTA AGC TTT AGG TTT AGG ATT AAA TCC CAA AGG CGG TAT TCC TAT TTG  976
Pro Tyr Ala Lys Pro Lys Pro Asn Phe Gly Leu Pro Pro Ile Gly Ile Gln
            290             295             300

AGC ATC CAA ATC ATC ATA AAT TGT GGC AAA TGT AGA AAA ATC TCT TGT TTT 1027
Ala Asp Leu Asp Asp Tyr Ile Thr Ala Phe Thr Ser Phe Asp Arg Thr Lys
        305             310             315             320

GGA TAA TTC TGA TTT TAG AAA AGA CTT TCT CAT ATA TAC TAA TGG AAT GCC 1078
Ser Leu Glu Ser Lys Leu Phe Ser Lys Arg Met Tyr Val Leu Pro Ile Gly
            325             330             335

TTT ATA TTT TTT AGA TGT AAT AAA AGT ATT AAT ATT TAT ATT TTT ATC TTG 1129
Lys Tyr Lys Lys Ser Thr Ile Phe Thr Asn Ile Asn Ile Asn Lys Asp Gln
        340             345             350

TAA ATA TTT TTT TAT AGT CCA AAA TAG AAA AAA TTT TCT TTT AAT ATT ATT 1180
Leu Tyr Lys Lys Ile Thr Trp Phe Leu Phe Phe Lys Arg Lys Ile Asn Asn
355             360             365             370

TTC AAA ATT AAT ATT ATT AAT ATG ATT TGG ATC TAA AAC TAA TTC ATT ATA 1231
Glu Phe Asn Ile Asn Asn Ile His Asn Pro Asp Leu Val Leu Glu Asn Tyr
        375             380             385

TAA TAT TTC CAA GTA TTT TAT AGG TAT AAA TGT TAC TTT ACC TCT TGT TTC 1282
Leu Ile Glu Leu Tyr Lys Ile Pro Ile Phe Thr Val Lys Gly Arg Thr Glu
    390             395             400             405

ATC ATC ATC ATC TAT TTT TTC TAA TAT AGC TAT ATT TGC ATT AGT ATT ATA 1333
Asp Asp Asp Asp Ile Lys Glu Leu Ile Ala Ile Asn Ala Asn Thr Asn Tyr
                410             415             420

TTT AAT AGG ATT TAT AAA ATA TAC CAT ATT ATC TAT TTT ACT AAA AAA TAA 1384
Lys Ile Pro Asn Ile Phe Tyr Val Met Asn Asp Ile Lys Ser Phe Phe Leu
        425             430             435

CAT AGA CAT AAA ATT AAT ACC AGA TTC TGG CAT TTT TAA ATT TTT ATT TGG 1435
Met Ser Met Phe Asn Ile Gly Ser Glu Pro Met Lys Leu Asn Lys Asn Pro
440             445             450             455

< G1L            G2R >
AAA TCT TCT AAT TTT ATT ATT CAT TATTTATTTA ATAA ATG TTT CTA GTT TAT 1488
Phe Arg Arg Ile Lys Asn Asn Met                Met Phe Leu Val Tyr
            460                                465

TTC AAT ACA TTT TTA ATA ATA ATT TTA TTA TTT GGT ATT ATA GGT ATT TAT 1539
Phe Asn Thr Phe Leu Ile Ile Ile Leu Leu Phe Gly Ile Ile Gly Ile Tyr
470             475             480             485

ATA TTA ACA TTT GTG TTT AAT ATA GAT TTT TTA ATA AAT AAT AAT AAA ATA 1590
Ile Leu Thr Phe Val Phe Asn Ile Asp Phe Leu Ile Asn Asn Asn Lys Ile
        490             495             500
```

FIG. 2B

```
TAT ATA TTA TCA TAT AAC GCA ACT AAT ATA AAC AAT ATA AAT AAT TTA AAT 1641
Tyr Ile Leu Ser Tyr Asn Ala Thr Asn Ile Asn Asn Ile Asn Asn Leu Asn
        505                 510                 515                 520

TTA TAC GAT TAT TCA GAT ATT ATA TTT TTG ACA AAT TTT AAC ATA AAT AAT 1692
Leu Tyr Asp Tyr Ser Asp Ile Ile Phe Leu Thr Asn Phe Asn Ile Asn Asn
                525                 530                 535

AAT CTT TTA GTA ACA CAA GCT AAT AAT TTA CAA GAT ATA CCA ATA TTT AAT 1743
Asn Leu Leu Val Thr Gln Ala Asn Asn Leu Gln Asp Ile Pro Ile Phe Asn
            540                 545                 550

GTA AAT AAT ATT ATA TCT AAT CAA TAT AAT TTT TAT TCA GCG TCT AGT AAT 1794
Val Asn Asn Ile Ile Ser Asn Gln Tyr Asn Phe Tyr Ser Ala Ser Ser Asn
555                 560                 565                 570

AAT GTA AAT ATA TTA TTA GGA TTA AGA AAA ACA TTA AAT ATA AAT AGA AAT 1845
Asn Val Asn Ile Leu Leu Gly Leu Arg Lys Thr Leu Asn Ile Asn Arg Asn
                575                 580                 585

CCA TTT TTA TTA TTT AGA AAT ACA TCT CTA GCT ATA GTT TTC AAT AAT AAT 1896
Pro Phe Leu Leu Phe Arg Asn Thr Ser Leu Ala Ile Val Phe Asn Asn Asn
        590                 595                 600                 605

GAA ACT TTT CAC TGT TAT ATA AGT TCA AAT CAA AAT AGT GAT GTA TTA GAT 1947
Glu Thr Phe His Cys Tyr Ile Ser Ser Asn Gln Asn Ser Asp Val Leu Asp
                610                 615                 620

ATA GTA TCA CAT ATA GAA TTT ATG AAA TCT AGA TAT AAT AAA TAT GTA ATT 1998
Ile Val Ser His Ile Glu Phe Met Lys Ser Arg Tyr Asn Lys Tyr Val Ile
            625                 630                 635

ATA GGA GAA ATA CCC GTA AAT AAT AAT ATA TCT ATT AAT AAT ATA TTA AAT 2049
Ile Gly Glu Ile Pro Val Asn Asn Asn Ile Ser Ile Asn Asn Ile Leu Asn
640                 645                 650                 655

AAT TTT GCT ATT ATA ACT AAT GTG AGA TTA ATA GAT AAA TAT AAC TCT ATA 2100
Asn Phe Ala Ile Ile Thr Asn Val Arg Leu Ile Asp Lys Tyr Asn Ser Ile
                660                 665                 670

ATA TCA TTT TTA AAT ATC AAC GTA GGA ACA CTT TTT GTC ATA AAT CCA TAA 2151
Ile Ser Phe Leu Asn Ile Asn Val Gly Thr Leu Phe Val Ile Asn Pro
        675                 680                 685

TATTTAGTAA TAATCACTAA CATATTTTTT ATTAAAATGA ATAAAATATA TATTGTTATT      2211

GTCAATATTT TATATCATTT TACAGTC TTA TTT TTT TTT TTT GCT TTT AGG TAT      2265
                                Lys Lys Lys Lys Ser Lys Pro Ile
                                            690                 695

AAT TTT ACC TTC TAA ACG TTT ATC TCC CCA AAC ATC TAC AGT AGA TGG TTT 2316
Ile Lys Gly Glu Leu Arg Lys Asp Gly Trp Val Asp Val Thr Ser Pro Lys
        700                 705                 710

ATT AGA TTC TGT GTT ATA CAC ATC TGC TGG ATT TGC GGC ATT TGT ATC CAA 2367
Asn Ser Glu Thr Asn Tyr Val Asp Ala Pro Asn Ala Ala Asn Thr Asp Leu
715                 720                 725                 730

ACC ATA ATA TCC AGG TCT ATA ATT ATC TTT AAA AAC TTG GGA TTG AGA TAC 2418
Gly Tyr Tyr Gly Pro Arg Tyr Asn Asp Lys Phe Val Gln Ser Gln Ser Val
                735                 740                 745
```

FIG. 2C

```
TTC TTC AGT TTT TAA ATT ATT AAA ATA TCC AAG ATT ATT TTT TTT TGA TGA 2469
Glu Glu Thr Lys Leu Asn Asn Phe Tyr Gly Leu Asn Asn Lys Lys Ser Ser
    750                 755                 760                 765

< G3L                                G4R >
AGA CAT AATTGATATT ATAATACTTT ATAGAT ATG TCA ATA TTT ATC TAC TAT    2522
Ser Met                                   Met Ser Ile Phe Ile Tyr Tyr
                                                          770

ATT TTC AAC AAT AGA TTT TAT ATA TAT AAA AGA ATG AAT ACT GTA CAA ATT 2573
Ile Phe Asn Asn Arg Phe Tyr Ile Tyr Lys Arg Met Asn Thr Val Gln Ile
775                 780                 785                 790

TTA GTT GTC ATA TTA ATA ACA ACA GCA TTA TCT TTT CTA GTT TTT CAA TTA 2624
Leu Val Val Ile Leu Ile Thr Thr Ala Leu Ser Phe Leu Val Phe Gln Leu
                795                 800                 805

TGG TAT TAT GCC GAA AAT TAC GAA TAT ATA TTA AGA TAT AAT GAT ACA TAT 2675
Trp Tyr Tyr Ala Glu Asn Tyr Glu Tyr Ile Leu Arg Tyr Asn Asp Thr Tyr
    810                 815                 820                 825

TCA AAT TTA CAA TTT GCG AGA AGC GCA AAT ATA AAT TTT GAT GAT TTA ACT 2726
Ser Asn Leu Gln Phe Ala Arg Ser Ala Asn Ile Asn Phe Asp Asp Leu Thr
                830                 835                 840

GTT TTT GAT CCC AAC GAT AAT GTT TTT AAT GTT GAA GAA AAA TGG CGC TGT 2777
Val Phe Asp Pro Asn Asp Asn Val Phe Asn Val Glu Glu Lys Trp Arg Cys
            845                 850                 855

GCT TCA ACT AAT AAT AAT ATA TTT TAT GCA GTT TCA ACT TTT GGA TTT TTA 2828
Ala Ser Thr Asn Asn Asn Ile Phe Tyr Ala Val Ser Thr Phe Gly Phe Leu
860                 865                 870                 875

AGT ACA GAA AGT ACT GGT ATT AAT TTA ACA TAT ACA AAT TCT AGA GAT TGT 2879
Ser Thr Glu Ser Thr Gly Ile Asn Leu Thr Tyr Thr Asn Ser Arg Asp Cys
            880                 885                 890

ATT ATA GAT TTA TTT TCT AGA ATT ATA AAA ATA GTA TAT GAT CCT TGT ACT 2930
Ile Ile Asp Leu Phe Ser Arg Ile Ile Lys Ile Val Tyr Asp Pro Cys Thr
            895                 900                 905             910

GTC GAA ACA TCT AAC GAT TGT AGA TTA TTA AGA TTA TTG ATG GCC AAT ACA 2981
Val Glu Thr Ser Asn Asp Cys Arg Leu Leu Arg Leu Leu Met Ala Asn Thr
                915                 920                 925

TCA TAA ATACATTATA ATATTATTAT AATATCAATC ATAATTTTTA TATATATTTT      3037
Ser
                                            G5R >
ATCTAAAAGG ACTTTTTATT TTTTATATAT TAATAATAAT AA ATG AGT AAC GTA CCT 3094
                                               Met Ser Asn Val Pro
                                                           930

TTA GCA ACC AAA ACA ATA AGA AAA TTA TCA AAT CGA AAA TAT GAA ATA AAG 3145
Leu Ala Thr Lys Thr Ile Arg Lys Leu Ser Asn Arg Lys Tyr Glu Ile Lys
    935                 940                 945                 950

ATT TAT TTA AAA GAT GAA AAT ACT TGT TTC GAA CGT GTA GTA GAT ATG GTA 3196
Ile Tyr Leu Lys Asp Glu Asn Thr Cys Phe Glu Arg Val Val Asp Met Val
                955                 960                 965
```

FIG. 2D

```
GTT CCA TTA TAT GAT GTG TGT AAT GAA ACT TCT GGT GTT ACT TTA GAA TCA 3247
Val Pro Leu Tyr Asp Val Cys Asn Glu Thr Ser Gly Val Thr Leu Glu Ser
        970              975              980

TGT AGT CCA AAT ATA GAA GTA ATT GAA TTA GAC AAT ACT CAT GTT AGA ATC 3298
Cys Ser Pro Asn Ile Glu Val Ile Glu Leu Asp Asn Thr His Val Arg Ile
985          990              995              1000

AAA GTT CAC GGC GAT ACA TTA AAA GAA ATG TGT TTT GAA TTA TTG TTC CCG 3349
Lys Val His Gly Asp Thr Leu Lys Glu Met Cys Phe Glu Leu Leu Phe Pro
            1005             1010             1015

TGT AAT GTA AAC GAA GCC CAA GTA TGG AAA TAT GTA AGT CGA TTA TTG CTA 3400
Cys Asn Val Asn Glu Ala Gln Val Trp Lys Tyr Val Ser Arg Leu Leu Leu
        1020             1025             1030             1035

GAT AAT GTA TCA CAT AAT GAC GTA AAA TAT AAA TTA GCT AAT TTT AGA CTG 3451
Asp Asn Val Ser His Asn Asp Val Lys Tyr Lys Leu Ala Asn Phe Arg Leu
            1040             1045             1050

ACT CTT AAT GGA AAA CAT TTA AAA TTA AAA GAA ATC GAT CAA CCG CTA TTT 3502
Thr Leu Asn Gly Lys His Leu Lys Leu Lys Glu Ile Asp Gln Pro Leu Phe
            1055             1060             1065

ATT TAT TTT GTC GAT GAT TTG GGA AAT TAT GGA TTA ATT ACT AAG GAA AAT 3553
Ile Tyr Phe Val Asp Asp Leu Gly Asn Tyr Gly Leu Ile Thr Lys Glu Asn
1070             1075             1080             1085

ATT CAA AAT AAT AAT TTA CAA GTT AAC AAA GAT GCA TCA TTT ATT ACT ATA 3604
Ile Gln Asn Asn Asn Leu Gln Val Asn Lys Asp Ala Ser Phe Ile Thr Ile
            1090             1095             1100

TTT CCA CAA TAT GCG TAT ATT TGT TTA GGT AGA AAA GTA TAT TTA AAT GAA 3655
Phe Pro Gln Tyr Ala Tyr Ile Cys Leu Gly Arg Lys Val Tyr Leu Asn Glu
    1105             1110             1115             1120

AAA GTA ACT TTT GAT GTA ACT ACA GAT GCA ACT AAT ATT ACT TTA GAT TTT 3706
Lys Val Thr Phe Asp Val Thr Thr Asp Ala Thr Asn Ile Thr Leu Asp Phe
                1125             1130             1135

AAT AAA TCT GTT AAT ATC GCA GTA TCA TTC CTT GAT ATA TAT TAC GAA GTT 3757
Asn Lys Ser Val Asn Ile Ala Val Ser Phe Leu Asp Ile Tyr Tyr Glu Val
            1140             1145             1150

AAT AAT AAT GAA CAA AAA GAT TTA TTA AAA GAT TTA CTT AAG AGA TAC GGT 3808
Asn Asn Asn Glu Gln Lys Asp Leu Leu Lys Asp Leu Leu Lys Arg Tyr Gly
1155             1160             1165             1170

GAA TTT GAA GTC TAT AAC GCA GAT ACT GGA TTA ATT TAT GCT AAA AAT CTA 3859
Glu Phe Glu Val Tyr Asn Ala Asp Thr Gly Leu Ile Tyr Ala Lys Asn Leu
            1175             1180             1185

AGT ATT AAA AAT TAT GAT ACT GTG ATT CAA GTA GAA AGG TTG CCA GTT AAT 3910
Ser Ile Lys Asn Tyr Asp Thr Val Ile Gln Val Glu Arg Leu Pro Val Asn
        1190             1195             1200             1205

TTG AAA GTT AGA GCA TAT ACT AAG GAT GAA AAT GGT CGC AAT CTA TGT TTG 3961
Leu Lys Val Arg Ala Tyr Thr Lys Asp Glu Asn Gly Arg Asn Leu Cys Leu
            1210             1215             1220
```

FIG. 2E

```
                                      _____RM58_____
ATG AAA ATA ACA TCT AGT ACA GAA GTA GAC CCC GAG TAT GTA ACT AGT AAT 4012
Met Lys Ile Thr Ser Ser Thr Glu Val Asp Pro Glu Tyr Val Thr Ser Asn
        1225            1230            1235

AAT GCT TTA TTG GGT ACG CTC AGA GTA TAT AAA AAG TTT GAT AAA TCT CAT 4063
Asn Ala Leu Leu Gly Thr Leu Arg Val Tyr Lys Lys Phe Asp Lys Ser His
1240            1245            1250            1255

TTA AAA ATT GTA ATG CAT AAC AGA GGA AGT GGT AAT GTA TTT CCA TTA AGA 4114
Leu Lys Ile Val Met His Asn Arg Gly Ser Gly Asn Val Phe Pro Leu Arg
            1260            1265            1270

TCA TTA TAT CTG GAA TTG TCT AAT GTA AAA GGA TAT CCA GTT AAA GCA TCT 4165
Ser Leu Tyr Leu Glu Leu Ser Asn Val Lys Gly Tyr Pro Val Lys Ala Ser
        1275            1280            1285            1290

GAT ACT TCG AGA TTA GAT GTT GGT ATT TAC AAA TTA AAT AAA ATT TAT GTA 4216
Asp Thr Ser Arg Leu Asp Val Gly Ile Tyr Lys Leu Asn Lys Ile Tyr Val
            1295            1300            1305

GAT AAC GAC GAA AAT AAA ATT ATA TTG GAA GAA ATT GAA GCA GAA TAT AGA 4267
Asp Asn Asp Glu Asn Lys Ile Ile Leu Glu Glu Ile Glu Ala Glu Tyr Arg
        1310            1315            1320

TGC GGA AGA CAA GTA TTC CAC GAA CGT GTA AAA CTT AAT AAA CAC CAA TGT 4318
Cys Gly Arg Gln Val Phe His Glu Arg Val Lys Leu Asn Lys His Gln Cys
1325            1330            1335            1340

AAA TAT ACT CCC AAA TGT CCA TTC CAA TTT GTT GTA AAC AGC CCA GAT ACT 4369
Lys Tyr Thr Pro Lys Cys Pro Phe Gln Phe Val Val Asn Ser Pro Asp Thr
            1345            1350            1355

ACG ATT CAC TTA TAT GGT ATT TCT AAT GTT TGT TTA AAA CCT AAA GTA CCC 4420
Thr Ile His Leu Tyr Gly Ile Ser Asn Val Cys Leu Lys Pro Lys Val Pro
        1360            1365            1370            1375

AAA AAT TTA AGA CTT TGG GGA TGG ATT TTA GAT TGC GAT ACT TCT AGA TTT 4471
Lys Asn Leu Arg Leu Trp Gly Trp Ile Leu Asp Cys Asp Thr Ser Arg Phe
            1380            1385            1390

ATT AAA CAT ATG GCT GAT GGA TCT GAT GAT TTA GAT CTT GAC GTT AGG CTT 4522
Ile Lys His Met Ala Asp Gly Ser Asp Asp Leu Asp Leu Asp Val Arg Leu
        1395            1400            1405

AAT AGA AAT GAT ATA TGT TTA AAA CAA GCC ATA AAA CAA CAT TAT ACT AAT 4573
Asn Arg Asn Asp Ile Cys Leu Lys Gln Ala Ile Lys Gln His Tyr Thr Asn
1410            1415            1420            1425

GTA ATT ATA TTA GAG TAC GCA AAT ACA TAT CCA AAT TGC ACA TTA TCA TTG 4624
Val Ile Ile Leu Glu Tyr Ala Asn Thr Tyr Pro Asn Cys Thr Leu Ser Leu
            1430            1435            1440

GGT AAT AAT AGA TTT AAT AAT GTA TTT GAT ATG AAT GAT AAC AAA ACT ATA 4675
Gly Asn Asn Arg Phe Asn Asn Val Phe Asp Met Asn Asp Asn Lys Thr Ile
        1445            1450            1455            1460

TCT GAG TAT ACT AAC TTT ACA AAA AGT AGA CAA GAC CTT AAT AAC ATG TCA 4726
Ser Glu Tyr Thr Asn Phe Thr Lys Ser Arg Gln Asp Leu Asn Asn Met Ser
            1465            1470            1475
```

FIG. 2F

```
TGT ATA TTA GGA ATA AAC ATA GGT AAT TCC GTA AAT ATT AGT AGT TTG CCT 4777
Cys Ile Leu Gly Ile Asn Ile Gly Asn Ser Val Asn Ile Ser Ser Leu Pro
            1480            1485            1490

GGT TGG GTA ACA CCT CAC GAA GCT AAA ATT CTA AGA TCT GGT TGT GCT AGA 4828
Gly Trp Val Thr Pro His Glu Ala Lys Ile Leu Arg Ser Gly Cys Ala Arg
1495            1500            1505            1510

GTT AGA GAA TTT TGT AAA TCA TTC TGT GAT CTT TCT AAT AAG AGA TTC TAT 4879
Val Arg Glu Phe Cys Lys Ser Phe Cys Asp Leu Ser Asn Lys Arg Phe Tyr
                1515            1520            1525

GCT ATG GCT AGA GAT CTC GTA AGT TTA CTA TTT ATG TGT AAC TAT GTT AAT 4930
Ala Met Ala Arg Asp Leu Val Ser Leu Leu Phe Met Cys Asn Tyr Val Asn
        1530            1535            1540            1545

ATT GAA ATT AAC GAA GCA GTA TGC GAA TAT CCT GGA TAT GTC ATA TTA TTC 4981
Ile Glu Ile Asn Glu Ala Val Cys Glu Tyr Pro Gly Tyr Val Ile Leu Phe
                    1550            1555            1560

GCA AGA GCT ATT AAA GTA ATT AAT GAT TTA TTA TTA ATT AAC GGA GTA GAT 5032
Ala Arg Ala Ile Lys Val Ile Asn Asp Leu Leu Leu Ile Asn Gly Val Asp
            1565            1570            1575

AAT CTA GCA GGA TAT TCA ATT TCC TTA CCT ATA CAT TAT GGA TCT ACT GAA 5083
Asn Leu Ala Gly Tyr Ser Ile Ser Leu Pro Ile His Tyr Gly Ser Thr Glu
1580            1585            1590            1595

AAG ACT CTA CCA AAT GAA AAG TAT GGT GGT GTT GAT AAG AAA TTT AAA TAT 5134
Lys Thr Leu Pro Asn Glu Lys Tyr Gly Gly Val Asp Lys Lys Phe Lys Tyr
            1600            1605            1610

CTA TTC TTA AAG AAT AAA CTA AAA GAT TTA ATG CGT GAT GCT GAT TTT GTC 5185
Leu Phe Leu Lys Asn Lys Leu Lys Asp Leu Met Arg Asp Ala Asp Phe Val
        1615            1620            1625            1630

CAA CCT CCA TTA TAT ATT TCT ACT TAC TTT AGA ACT TTA TTG GAT GCT CCA 5236
Gln Pro Pro Leu Tyr Ile Ser Thr Tyr Phe Arg Thr Leu Leu Asp Ala Pro
                1635            1640            1645

CCA ACT GAT AAT TAT GAA AAA TAT TTG GTT GAT TCG TCC GTA CAA TCA CAA 5287
Pro Thr Asp Asn Tyr Glu Lys Tyr Leu Val Asp Ser Ser Val Gln Ser Gln
        1650            1655            1660

GAT GTT CTA CAG GGT CTG TTG AAT ACA TGT AAT ACT ATT GAT ACT AAT GCT 5338
Asp Val Leu Gln Gly Leu Leu Asn Thr Cys Asn Thr Ile Asp Thr Asn Ala
1665            1670            1675            1680

AGA GTT GCA TCA AGT GTT ATT GGA TAT GTT TAT GAA CCA TGC GGA ACA TCA 5389
Arg Val Ala Ser Ser Val Ile Gly Tyr Val Tyr Glu Pro Cys Gly Thr Ser
            1685            1690            1695

GAA CAT AAA ATT GGT TCA GAA GCA TTG TGT AAA ATG GCT AAA GAA GCA TCT 5440
Glu His Lys Ile Gly Ser Glu Ala Leu Cys Lys Met Ala Lys Glu Ala Ser
        1700            1705            1710            1715

AGA TTA GGA AAT CTA GGT TTA GTA AAT CGT ATT AAT GAA AGT AAT TAC AAC 5491
Arg Leu Gly Asn Leu Gly Leu Val Asn Arg Ile Asn Glu Ser Asn Tyr Asn
                1720            1725            1730
```

FIG. 2G

```
AAA TGT AAT AAA TAT GGT TAT AGA GGA GTA TAC GAA AAT AAC AAA CTA AAA  5542
Lys Cys Asn Lys Tyr Gly Tyr Arg Gly Val Tyr Glu Asn Asn Lys Leu Lys
            1735            1740            1745

ACA AAA TAT TAT AGA GAA ATA TTT GAT TGT AAT CCT AAT AAT AAT AAT GAA  5593
Thr Lys Tyr Tyr Arg Glu Ile Phe Asp Cys Asn Pro Asn Asn Asn Asn Glu
1750            1755            1760            1765

TTA ATA TCC AGA TAT GGA TAT AGA ATA ATG GAT TTA CAT AAA ATT GGA GAA  5644
Leu Ile Ser Arg Tyr Gly Tyr Arg Ile Met Asp Leu His Lys Ile Gly Glu
            1770            1775            1780

ATT TTT GCA AAT TAC GAT GAA AGT GAA TCT CCT TGC GAA CGA AGA TGT CAT  5695
Ile Phe Ala Asn Tyr Asp Glu Ser Glu Ser Pro Cys Glu Arg Arg Cys His
            1785            1790            1795            1800

TAC TTG GAA GAT AGA GGT CTT TTA TAT GGT CCT GAA TAT GTA CAT CAC AGA  5746
Tyr Leu Glu Asp Arg Gly Leu Leu Tyr Gly Pro Glu Tyr Val His His Arg
                1805            1810            1815

TAT CAA GAA TCA TGT ACG CCT AAT ACG TTT GGA AAT AAC ACA AAT TGT GTA  5797
Tyr Gln Glu Ser Cys Thr Pro Asn Thr Phe Gly Asn Asn Thr Asn Cys Val
            1820            1825            1830

ACA AGA AAT GGT GAA CAA CAC GTA TAC GAA AAT AGT TGT GGA GAT AAT GCA  5848
Thr Arg Asn Gly Glu Gln His Val Tyr Glu Asn Ser Cys Gly Asp Asn Ala
1835            1840            1845            1850

ACA TGT GGA AGA AGA ACA GGA TAT GGA AGA AGA AGT AGG GAT GAA TGG AAT  5899
Thr Cys Gly Arg Arg Thr Gly Tyr Gly Arg Arg Ser Arg Asp Glu Trp Asn
            1855            1860            1865

GAC TAT AGA AAA CCC CAC GTT TAT GAC AAT TGT GCC GAT GCA AAT AGT TCA  5950
Asp Tyr Arg Lys Pro His Val Tyr Asp Asn Cys Ala Asp Ala Asn Ser Ser
    1870            1875            1880            1885

TCT TCA GAT AGC TGT TCA GAC AGT AGT AGT AGT AGT GAA TCT GAA TCT GAT  6001
Ser Ser Asp Ser Cys Ser Asp Ser Ser Ser Ser Ser Glu Ser Glu Ser Asp
            1890            1895            1900

TCA GAT GGA TGT TGC GAC ACA GAT GCT AGT TTA GAT TCT GAT ATT GAA AAT  6052
Ser Asp Gly Cys Cys Asp Thr Asp Ala Ser Leu Asp Ser Asp Ile Glu Asn
    1905            1910            1915

TGT TAT CAA AAT CCA TCA AAA TGT GAT GCA GGA TGC TAA ATGAAATTTA        6101
Cys Tyr Gln Asn Pro Ser Lys Cys Asp Ala Gly Cys
1920            1925            1930

ATATTATATA ATATTAACTT ACAAGTTATA AAAATCATTA AAATGATTTT TTAAAATGAT     6161

ATTATCGATA GTTGTGATAA TGTGCTCTTT TATTTTATTA ATTGCGATGA TTATAATATT     6221

ATCTTTTAGA TATATTTAAT ATTAATTATA AATCGACTGA CAATAATATT TATTC CTA      6279

TTC ATA ATA ATC ATC TGC TAT ATA TAT TAA TGT ATC ATT CTC TAT TAT AAA  6330
Glu Tyr Tyr Asp Asp Ala Ile Tyr Ile Leu Thr Asp Asn Glu Ile Ile Phe
        1935            1940            1945

TAT AGG TAT ATT GTC TTT ATC AAT CAT TAA TTT TGC TAC AGC TGT ATT ATC  6381
Ile Pro Ile Asn Asp Lys Asp Ile Met Leu Lys Ala Val Ala Thr Asn Asp
1950            1955            1960            1965
```

FIG. 2H

```
TTT ATA TAC TAT ATT TGT GTC TTT GTT TAA TAA ACC TTT TAA TAT AGT GGC  6432
Lys Tyr Val Ile Asn Thr Asp Lys Asn Leu Leu Gly Lys Leu Ile Thr Ala
            1970            1975            1980

TCT ATC ATA ATC TTT ACA ATA TGA TAT GGG ATA TAA TTT TAT ATT AAT AAT  6483
Arg Asp Tyr Asp Lys Cys Tyr Ser Ile Pro Tyr Leu Lys Ile Asn Ile Ile
        1985            1990            1995

AAC ATT AGA TAC GTT CAT TTC TTT CAT TCT AGT TTT ACG TAT TGT GTC AAA  6534
Val Asn Ser Val Asn Met Glu Lys Met Arg Thr Lys Arg Ile Thr Asp Phe
2000            2005            2010            2015

AAT TAT TTC ATT TTC TGC TGG TTC TAT ATA TTT ATA TGT GTT ATG AAT AGA  6585
Ile Ile Glu Asn Glu Ala Pro Glu Ile Tyr Lys Tyr Thr Asn His Ile Ser
            2020            2025            2030

TTC GAT AGA TGA TGA TTT TAA TAA ATC AAA TAT AAC ATT TAT TTT ACC TTG  6636
Glu Ile Ser Ser Ser Lys Leu Leu Asp Phe Ile Val Asn Ile Lys Gly Gln
        2035            2040            2045            2050

TTT ATC TTT TAT AAT ATC TAA TAT TTC TTT ATC TAC AGA TTT TCT GTT GTT  6687
Lys Asp Lys Ile Ile Asp Leu Ile Glu Lys Asp Val Ser Lys Arg Asn Asn
            2055            2060            2065

GGT ATA TGA TAT TAA AAA ATG AAC GTT AAC ATA TCT ATA TTC TTG TGG TAA  6738
Thr Tyr Ser Ile Leu Phe His Val Asn Val Tyr Arg Tyr Glu Gln Pro Leu
        2070            2075            2080

< G6L
ATC TTT ATG AGA ATT TAA TCT TAT AGA TCT                              6768
Asp Lys His Ser Asn Leu Arg Ile Ser Arg
2085            2090        2094
```

FIG. 2I

```
GAATTCAAGT TAAATAT TTA TAA ACA ACA ATC ATA TTT TTT TAA AGA ATC TAA    53
                    Leu Cys Cys Asp Tyr Lys Lys Leu Ser Asp Leu
                     1               5                  10

TAA ATT TTT TAA CAT TTT ATT ATT ATT TGA TAA TTG TTT ATT TAA TTC GTT  104
Leu Asn Lys Leu Met Lys Asn Asn Asn Ser Leu Gln Lys Asn Leu Glu Asn
             15                  20                  25

ATT GAT ATT AAC AAT ATT ATT TAT CAT TTT ACC TAT TTT TTT TTT TCT ATC  155
Asn Ile Asn Val Ile Asn Asn Ile Met Lys Gly Ile Lys Lys Lys Arg Asp
     30                  35                  40                  45
                     RM129
TAC TAA CGA AAT ATC AGA TTT TGC ACC TTC AAT ATC AGA ATA ATA ATT ATC  206
Val Leu Ser Ile Asp Ser Lys Ala Gly Glu Ile Asp Ser Tyr Tyr Asn Asp
             50                  55                  60

< ORF Q1
ATT ATT TTG CAT TTATGAATAA AAATA TTA ATA TGA ATT ATT ATA ACA TAA     257
Asn Asn Gln Met                 Tyr Ser Asn Asn Tyr Cys Leu
         65                                          70

TCT ACA CAC AGG AAC ATA TAA ATC TTG TCC ACC TAT TTC AAT TAT TTG ATT  308
Arg Cys Val Pro Val Tyr Leu Asp Gln Gly Gly Ile Glu Ile Ile Gln Asn
         75                  80                  85                  90

TTT ATT ATG TTT TTT AAT TGT AAA AGA AGC ATC TTT ATA ACA AAA TTG ACA  359
Lys Asn His Lys Lys Ile Thr Phe Ser Ala Asp Lys Tyr Cys Phe Gln Cys
             95                 100                 105

TAT AGC TTG TAA TTT TTT TAT TTT TTC TAC TTT AGG AAT TAA TTT TGA TAT  410
Ile Ala Gln Leu Lys Lys Ile Lys Glu Val Lys Pro Ile Leu Lys Ser Ile
        110                 115                 120
                                                  RM03
AGA ATT AAA TAT ATT TCT GTT AAA GTC ACA ATT TAA TCC AGC AAC AAT AAC  461
Ser Asn Phe Ile Asn Arg Asn Phe Asp Cys Asn Leu Gly Ala Val Ile Val
125             130                 135                 140

TTT TTT TTT ATT ATT AGC CAT TTT ATC ACA AAA TTG TTC TAA ATC ATT TTC  512
Lys Lys Lys Asn Asn Ala Met Lys Asp Cys Phe Gln Glu Leu Asp Asn Glu
            145                 150                 155

TTC AAA AAA TTG ACA CTC ATC TAT GCC AAT AAT ATC ATA ATT ATC TAC GAT  563
Glu Phe Phe Gln Cys Glu Asp Ile Gly Ile Ile Asp Tyr Asn Asp Val Ile
        160                 165                 170                 175

ATT GAT TTC ATT AAT TAA ATT ATT TGT TTT AAT GTA TAA ATA TTC TTT ATT  614
Asn Ile Glu Asn Ile Leu Asn Asn Thr Lys Ile Tyr Leu Tyr Glu Lys Asn
            180                 185                 190

TAA TAT ATT TCC GTC ATG ATT TAT TAT ATT TTT ATT TAT AAA TCT ATT ATC  665
Leu Ile Asn Gly Asp His Asn Ile Ile Asn Lys Asn Ile Phe Arg Asn Asp
        195                 200                 205

TAT ATT ATG AGT TAT AAT TAC ACA TTT TTG ATT AGA TAA AAT ATA TCT ATT  716
Ile Asn His Thr Ile Ile Val Cys Lys Gln Asn Ser Leu Ile Tyr Arg Asn
210             215                 220                 225
```

FIG. 3A

```
                                                         RM04
AAT TTT TCG CAT CAA TTC TGT TGT TTT GCC AGA AAA CAT AGG ACC AAT TAT   767
Ile Lys Arg Met Leu Glu Thr Thr Lys Gly Ser Phe Met Pro Gly Ile Ile
            230             235             240

< ORF Q2
TAA TTC TAT CGA CAT TTTTTTTTAT TATTTGATAT ATTTTTTCAA AAAAAAATTA       822
Leu Glu Ile Ser Met
245
                                     ORF Q3 >
ATCAATGAAA AAAAAATAAA ATTATCAAA ATG GAT TTA CTA AAT TCT GAT ATA ATT   878
                                Met Asp Leu Leu Asn Ser Asp Ile Ile
                                    250             255

TTA ATA AAT ATT TTA AAA TAT TAT AAT TTA AAA AAA ATA ATA ATA AAC AGA   929
Leu Ile Asn Ile Leu Lys Tyr Tyr Asn Leu Lys Lys Ile Ile Ile Asn Arg
            260             265             270

GAT AAT GTT ATT AAT ATT AAT ATA TTA AAA AAA TTA GTT AAT TTA GAA GAA   980
Asp Asn Val Ile Asn Ile Asn Ile Leu Lys Lys Leu Val Asn Leu Glu Glu
275             280             285             290

TTG CAT ATA ATA TAT TAT GAT AAT AAT ATT TTA AAT AAT ATT CCA GAA AAT  1031
Leu His Ile Ile Tyr Tyr Asp Asn Asn Ile Leu Asn Asn Ile Pro Glu Asn
            295             300             305

ATT AAA AGT TTA TAT ATT TCA AAT TTA AAT ATT ATT AAT TTA AAT TTT ATA  1082
Ile Lys Ser Leu Tyr Ile Ser Asn Leu Asn Ile Ile Asn Leu Asn Phe Ile
            310             315             320             325

ACA AAA TTA AAA AAT ATA ACA TAT TTA GAT ATA TCT TAT AAC AAA AAT AGC  1133
Thr Lys Leu Lys Asn Ile Thr Tyr Leu Asp Ile Ser Tyr Asn Lys Asn Ser
            330             335             340

AAT ATA AGT AAT ATT ATA CTA CCA CAT TCT ATA GAA TTT TTA AAT TGT GAA  1184
Asn Ile Ser Asn Ile Ile Leu Pro His Ser Ile Glu Phe Leu Asn Cys Glu
            345             350             355

TCA TGT AAT ATA AAT GAC TAT AAT TTT ATT AAT AAT TTA GTA AAT TTA AAA  1235
Ser Cys Asn Ile Asn Asp Tyr Asn Phe Ile Asn Asn Leu Val Asn Leu Lys
360             365             370             375

AAA TTA ATA ATA TCT AAA AAT AAA TTT GGT AAC TTT AAT AAT GTT TTT CCT  1286
Lys Leu Ile Ile Ser Lys Asn Lys Phe Gly Asn Phe Asn Asn Val Phe Pro
            380             385             390

ATT AGT ATA GTT GAG TTA AAT ATG GAA TCA ATA CAA ATA AAA GAT TAT AAA  1337
Ile Ser Ile Val Glu Leu Asn Met Glu Ser Ile Gln Ile Lys Asp Tyr Lys
395             400             405             410

TTT ATA GAA AAA TTA ATT AAT TTA AAA AAA TTA GAT ATA TCT TTC AAT GTT  1388
Phe Ile Glu Lys Leu Ile Asn Leu Lys Lys Leu Asp Ile Ser Phe Asn Val
                415             420             425

AAA AAA AAT AAT ATA CAT TTG ATA AAA TTT CCA AAA AGT ATA ACT CAT TTA  1439
Lys Lys Asn Asn Ile His Leu Ile Lys Phe Pro Lys Ser Ile Thr His Leu
            430             435             440
```

FIG. 3B

```
TGT GAT TAT CAA TCA TAT AAA GAA AAT TAT AAT TAT TTA AAA AAT TTA TCA 1490
Cys Asp Tyr Gln Ser Tyr Lys Glu Asn Tyr Asn Tyr Leu Lys Asn Leu Ser
445             450             455             460

AAT ATA ATT GAA TAT GAA TTC                                       1511
Asn Ile Ile Glu Tyr Glu Phe
            465
```

| Label | Oligonucleotide |
|---|---|
| RM58 | GARGTNGAYC CNGARTAYGT |
| RM82 | TTTCAAATTA ACTGGCAACC |
| RM83 | GGGATGGATT TTAGATTGCG |
| RM92 | GCCTGGTTGG GTAACACCTC |
| RM118 | CTGCTAGATT ATCTACTCCG |
| RM165 | GTTCGAAACA AGTATTTTCA TCTTTTAAAT AAATC |
| RM03 | GAYGARGGRG GRCARTTYTT |
| RM04 | GGNCCCATGT TYTCNGG |
| RM129 | GGTGCAAAAT CTGATATTTC |

ENTOMOPOXVIRUS EXPRESSION SYSTEM

This application is a 371 of PCT/US92/00855 which is a Continuation-in-Part of Ser. No. 07/827,685, filed on Jan. 30, 1992, now abandoned, which is a Continuation-in-Part of Ser. No. 07/657,584, filed Feb. 19, 1991, now abandoned.

FIELD OF THE INVENTION

This invention relates generally to the field of recombinantly-produced proteins and specifically to novel, recombinant Entomopoxvirus proteins, protein regulatory sequences and their uses in expressing heterologous genes in transformed hosts.

BACKGROUND OF THE INVENTION

Poxviruses are taxonomically classified into the family Chordopoxvirinae, whose members infect vertebrate hosts, e.g., the Orthopoxvirus vaccinia, or into the family Entomopoxvirinae. Very little is known about members of the Entomopoxvirinae family other than the insect host range of individual members. One species of Entomopoxvirus (EPV) is the *Amsacta moorei* Entomopoxvirus (AmEPV), which was first isolated from larvae of the red hairy caterpillar *Amsacta moorei* [Roberts and Granados, *J. Invertebr. Pathol.*, 12:141–143 (1968)]. AmEPV is the type species of genus B of EPVs and is one of three known EPVs which will replicate in cultured insect cells [R. R. Granados et al, "Replication of *Amsacta moorei* Entomopoxvirus and *Autographa californica* Nuclear Polyhedrosis Virus in Hemocyte Cell Lines from Estigmene acrea", in *Invertebrate Tissue Culture Applications in Medicine, Biology, and Agriculture*, E. Kurstak and K. Maramorosch (ed.), Academic Press, New York, pp. 379–389 (1976); T. Hukuhara et al, *J. Invertebr. Pathol.*, 56:222–232 (1990); and T. Sato, "Establishment of Eight Cell Lines from Neonate Larvae of Torticids (Lepidoptera), and Their Several Characteristics Including Susceptibility to Insect Viruses", in *Invertebrate Cell Systems Applications*, J. Mitsuhashi (ed.), Vol. II, pp. 187–198, CRC Press, Inc., Boca Raton, Fla. (1989)].

AmEPV is one of the few insect poxviruses which can replicate in insect cell culture; AmEPV is unable to replicate in vertebrate cell lines. The AmEPV double-stranded DNA genome is about 225 kb unusually A+T rich (18.5% G+C) [W. H. R. Langridge et al, *Virology*, 76:616–620 (1977)]. Recently, a series of restriction maps for AmEPV were published [R. L. Hall et al, *Arch. Virol.*, 110:77–90 (1990)]. No DNA homology to vaccinia has been detected [W. H. Langridge, *J. Invertebr. Pathol.*, 42:77–82 (1983); W. H. Langridge, *J. Invertebr. Pathol.*, 43:41–46 (1984)].

The viral replication cycle of AmEPV resembles that of other poxviruses except for the appearance of occluded virus late in infection. For AmEPV, once a cell is infected, both occluded and extracellular virus particles are generated. The mature occlusion body particle, which is responsible for environmentally protecting the virion during infection, consists of virus embedded within a crystalline matrix consisting primarily of a single protein, spheroidin. Spheroidin, the major structural protein of AmEPV, has been reported to be 110 kDa in molecular weight and to consist of a high percentage of charged and sulfur-containing amino acids [Langridge and Roberts, *J. Invertebr. Pathol.*, 39:346–353 (1982)]. The use of viruses and virus proteins in eukaryotic host-vector systems has been the subject of a considerable amount of investigation and speculation. Many existing viral vector systems suffer from significant disadvantages and limitations which diminish their utility. For example, a number of eukaryotic viral vectors are either tumorigenic or oncogenic in mammalian systems, creating the potential for serious health and safety problems associated with resultant gene products and accidental infections. Further, in some eukaryotic host-viral vector systems, the gene product itself exhibits antiviral activity, thereby decreasing the yield of that protein.

In the case of simple viruses, the amount of exogenous DNA which can be packaged into a simple virus is limited. This limitation becomes a particularly acute problem when the genes used are eukaryotic. Because eukaryotic genes usually contain intervening sequences, they are too large to fit into simple viruses. Further, because they have many restriction sites, it is more difficult to insert exogenous DNA into complex viruses at specific locations.

Vaccinia virus has recently been developed as a eukaryotic cloning and expression vector [M. Mackett et al, *DNA Cloning*, Vol. II, ed. D. M. Glover, pp. 191–212, Oxford: IRL Press (1985); D. Panicali et al, *Proc. Natl. Acad. Sci. USA*, 88:5364–5368 (1982)]. Numerous viral antigens have been expressed using vaccinia virus vectors [E. Paoletti et al, *Proc. Natl. Acad. Sci. USA*, 81:193–197 (1984); A. Piccine et al, *BioEssays*, 5:248–252 (1986)] including, among others, HBsAg, rabies G protein and the gp120/gp41 of human immunodeficiency virus (HIV). Regulatory sequences from the spruce budworm EPV have been used previously with vaccinia [L. Yuen et al, *Virology*, 175:427–433 (1990)].

Additionally, studies with vaccinia virus have demonstrated that poxviruses have several advantageous features as vaccine vectors. These include the ability of poxvirus-based vaccines to stimulate both cell-mediated and humoral immunity, minimal cost to mass produce vaccine and the stability of the lyophilized vaccine without refrigeration, ease of administration under non-sterile condition, and the ability to insert at least 25,000 base pairs of foreign DNA into an infectious recombinant, thereby permitting the simultaneous expression of many antigens from one recombinant.

There exists a need in the art for additional viral compositions and methods for use in expressing heterologous genes in selected host cells, and in performing other research and production techniques associated therewith.

SUMMARY OF THE INVENTION

As one aspect, the invention provides an Entomopoxvirus polynucleotide sequence, free from other viral sequences with which it is associated in nature, which comprises a sequence encoding the Entomopoxvirus spheroidin gene and/or its regulatory sequences, an allelic variant, an analog or a fragment thereof. In a particular embodiment, the spheroidin DNA sequence is isolated from the *Amsacta moorei* Entomopoxvirus and is illustrated in FIG. 2 [SEQ ID NO:1].

Another aspect of the invention is the polynucleotide sequence encoding the Entomopoxvirus spheroidin promoter or an allelic variant, analog or fragment thereof. The spheroidin promoter sequence is characterized by the ability to direct the expression of a heterologous gene to which the sequence or fragment is operably linked in a selected host cell.

As another aspect, the present invention provides a recombinant polynucleotide sequence comprising a sequence encoding the Entomopoxvirus spheroidin protein and/or its regulatory sequences, an allelic variant, analog or fragment thereof, linked to a second polynucleotide sequence encoding a heterologous gene. One embodiment of this polynucleotide sequence provides the spheroidin promoter sequence operably linked to the heterologous gene to direct the expression of the heterologous gene in a selected host cell. Another embodiment provides the sequence encoding the spheroidin protein linked to the heterologous gene in a manner permitting expression of a fusion protein. Still another embodiment provides the heterologous gene inserted into a site in the spheroidin gene so that the heterologous gene is flanked on both termini by spheroidin sequences.

As yet a further aspect, the invention provides an Entomopoxvirus polynucleotide sequence free from other viral sequences with which it is associated in nature, comprising a sequence encoding the Entomopoxvirus thymidine kinase (tk) gene and/or its regulatory sequences, an allelic variant, an analog or a fragment thereof. In a particular embodiment, the sequence originates from the Amsacta moorei Entomopoxvirus and is illustrated in FIG. 3 [SEQ ID NO:8].

In still another aspect the sequence encodes the Entomopoxvirus tk promoter, allelic variant or a fragment thereof. The tk promoter sequence is characterized by the ability to direct the expression of a heterologous gene to which the sequence or fragment is operably linked in a selected host cell.

Yet a further aspect of the invention provides a recombinant polynucleotide sequence described above encoding the Entomopoxvirus tk gene and/or its regulatory sequences, an allelic variant, or a fragment thereof, linked to a heterologous gene. One embodiment of this polynucleotide sequence provides the tk promoter sequence operably linked to the heterologous gene to direct the expression of the heterologous gene in a selected host cell. Another embodiment provides the sequence encoding the tk protein linked to the heterologous gene in a manner permitting expression of a fusion protein. Still another embodiment provides the heterologous gene inserted into a site in the tk gene so that the heterologous gene is flanked on both termini by tk sequences.

Another aspect of the invention is an Entomopoxvirus spheroidin polypeptide, a fragment thereof, or an analog thereof, optionally fused to a heterologous protein or peptide. Also provided is an Entomopoxvirus tk polypeptide, a fragment thereof, or an analog thereof, optionally linked to a heterologous protein or peptide.

Yet another aspect of the invention is provided by recombinant polynucleotide molecules which comprise one or more of the polynucleotide sequences described above. This molecule may be an expression vector or shuttle vector. The molecule may also contain viral sequences originating from a virus other than the Entomopoxvirus which contributed the spheroidin or tk polynucleotide sequence, e.g., vaccinia.

In another aspect, the present invention provides a recombinant virus comprising a polynucleotide sequence as described above. Also provided are host cells infected with one or more of the described recombinant viruses.

The present invention also provides a method for producing a selected polypeptide comprising culturing a selected host cell infected with a recombinant virus, as described above, and recovering said polypeptide from the culture medium.

As a final aspect, the invention provides a method for screening recombinant host cells for insertion of heterologous genes comprising infecting the cells with a recombinant virus containing a polynucleotide molecule comprising the selected heterologous gene sequence linked to an incomplete spheroidin or tk polynucleotide sequence or inserted into and interrupting the coding sequences thereof so that the heterologous gene is flanked at each termini by an Entomopoxvirus spheroidin or tk polynucleotide sequence. The absence of occlusion bodies formed by the expression of the spheroidin protein in the spheroidin containing cell indicates the integration of the heterologous gene. Alternatively, the absence of the thymidine kinase function, i.e., resistance to methotrexate or a nucleotide analogue of methotrexate, formed by the integration of the inactive thymidine kinase sequence indicates the insertion of the heterologous gene.

Other aspects and advantages of the present invention are described further in the following detailed description of embodiments of the present invention.

BRIEF DESCRIPTION OF THE DRAWINGS

FIG. 2 provides the AmEPV DNA sequence of the Amsacta moorei Entomopoxvirus spheroidin gene and flanking sequences [SEQ ID NO:1], the deduced amino acid sequences of the spheroidin protein [SEQ ID NO:6], and five additional open reading frames (ORFs).

FIG. 3 provides the DNA sequence of the Amsacta moorei Entomopoxvirus thymidine kinase (tk) gene and flanking sequences [SEQ ID NO:8], the deduced amino acid sequences of the tk protein [SEQ ID NO:11], and two additional ORFs.

FIG. 4 provides the nucleotide sequences of the synthetic oligonucleotides designated RM58 [SEQ ID NO:12], RM82 [SEQ ID NO:13], RM83 [SEQ ID NO:14], RM92 [SEQ ID NO:15], RM118 [SEQ ID NO:16], RM165 [SEQ ID NO:17], RM03 [SEQ ID NO:18], RM04 [SEQ ID NO:19], and RM129 [SEQ ID NO:20].

DETAILED DESCRIPTION OF THE INVENTION

Figure 1:
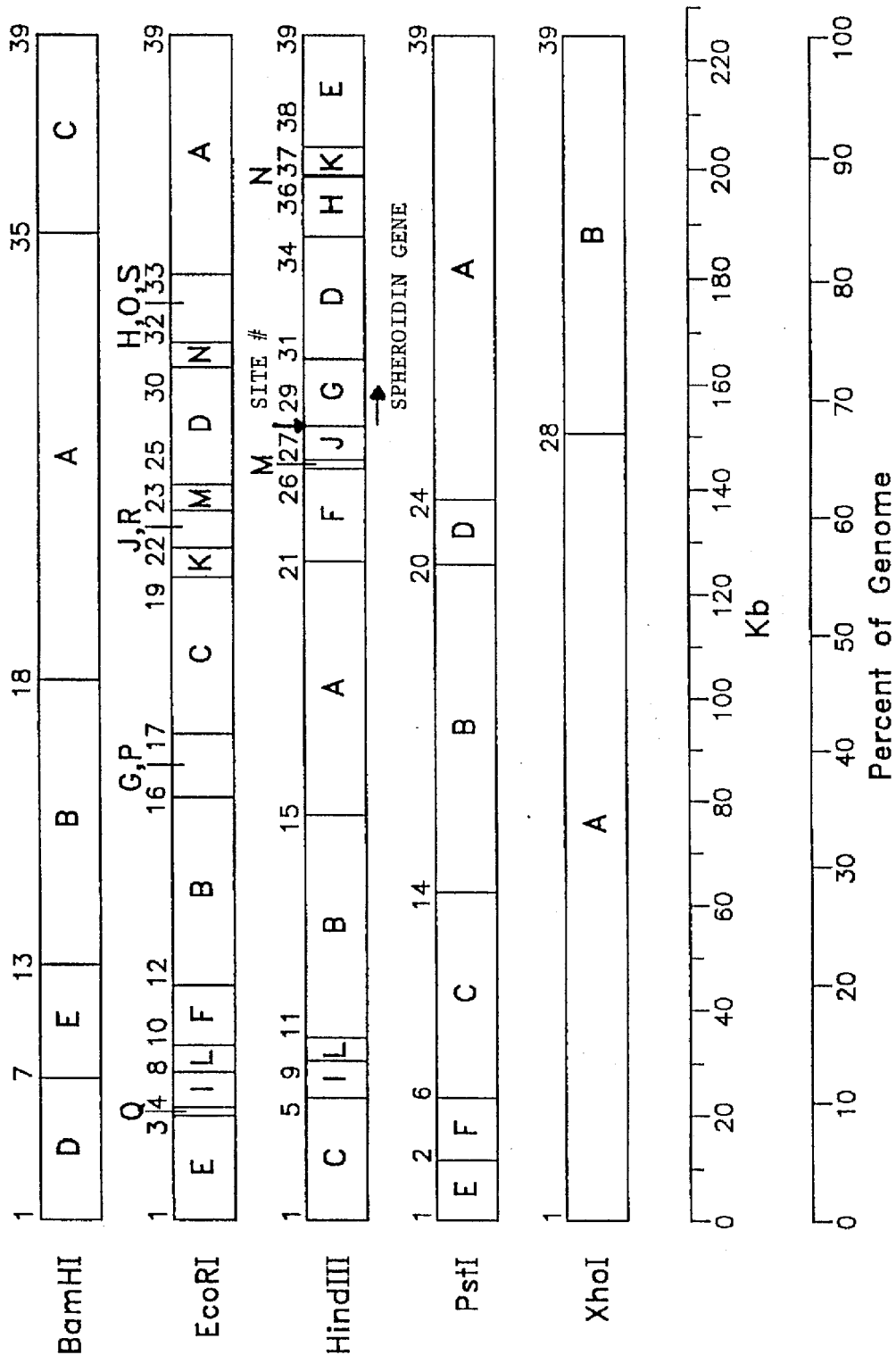
FIG. 1 is a physical map of AmEPV illustrating restriction fragments thereof and showing the spheroidin gene just to the right of site #29 in the HindIII-G fragment.
Figure 5:
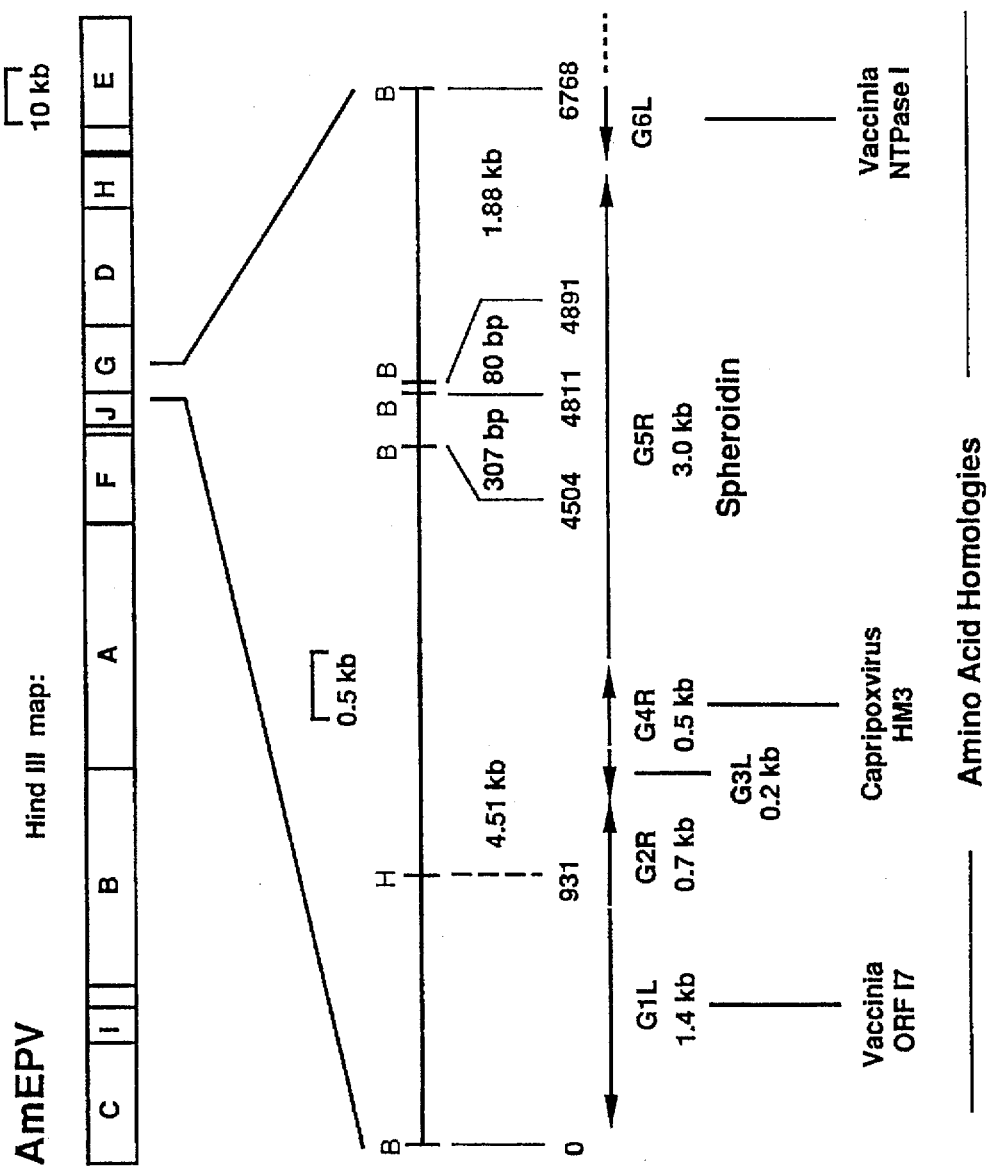
FIG. 5 is a schematic map of an AmEPV fragment illustrating the orientation of the spheroidin ORF on the physical map and indicating homologies.

The present invention provides novel Entomopoxvirus (EPV) polynucleotide sequences free from association with other viral sequences with which they are naturally associated. Recombinant polynucleotide vectors containing the sequences, recombinant viruses containing the sequences, and host cells infected with the recombinant viruses are also disclosed herein. These compositions are useful in methods of the invention for the expression of heterologous genes and production of selected proteins in both insect and mammalian host cells.

Novel polynucleotide sequences of the invention encode the EPV spheroidin gene and/or its flanking sequences, including sequences which provide regulatory signals for the expression of the gene. The invention also provides novel polynucleotide sequences encoding the EPV thymidine kinase (tk) gene and/or its flanking sequences. The polynucleotide sequences of this invention may be either RNA or DNA sequences. More preferably, the polynucleotide sequences of this invention are DNA sequences.

Specifically disclosed by the present invention are spheroidin and tk polynucleotide sequences obtained from the Amsacta moorei Entomopoxvirus (AmEPV). While this is the presently preferred species for practice of the methods and compositions of this invention, it is anticipated that, utilizing the techniques described herein, substantially homologous sequences may be obtained by one of skill in the art from other available Entomopoxvirus species.

The AmEPV spheroidin DNA sequence, including flanking and regulatory sequence, is reported in FIG. 2 as spanning nucleotides #1 through 6768 [SEQ ID NO:1]. Within this sequence, the spheroidin gene coding sequence spans nucleotides #3080 to #6091 [SEQ ID NO:21]. A fragment which is likely to contain the promoter sequences spans nucleotide #2781–3199 [SEQ ID NO:22]. Other regions of that sequence have also been identified as putative coding regions for other structural or regulatory genes associated with spheroidin. These other fragments of interest include the following sequences: nucleotide #1472 through 2151 [SEQ ID NO:23] encoding the G2R ORF [SEQ ID NO:3]; nucleotide #2502 through 2987 [SEQ ID NO:24] encoding the G4R ORF [SEQ ID NO:5]; and the following sequences transcribed left to right on FIG. 2: nucleotide #65 through 1459 [SEQ ID NO:25] encoding the G1L ORF [SEQ ID NO:2]; nucleotide #2239 through 2475 [SEQ ID NO:26] encoding the G3L ORF [SEQ ID NO:4]; and nucleotide #677 through 6768 [SEQ ID NO:27] encoding the G6L ORF [SEQ ID NO:7], These ORFs are identified in FIG. 2.

The AmEPV ORF G4R [SEQ ID NO:5] which is immediately upstream of the spheroidin gene has significant homology to the capripoxvirus HM30RF. A homolog of the HM30RF is found in vaccinia virus just upstream of a truncated version of the cowpox virus ATI gene. Therefore, the microenvironments in this region are similar in the two viruses. Two other ORFs relate to counterparts in vaccinia virus. These ORFs include the I7 ORF of the vaccinia virus HindIII-I fragment (I7) [J. F. C. Schmitt et al, *J. Virol.*, 62:1889–1897 (1988)]which relates to the AmEPV G1L ORF [SEQ ID NO:2] and the NTPase I (NPH I) ORF of the HindIII-D fragment which relates to the AmEPV G6L ORF [SEQ ID NO:7] [S. S. Broyles et al, *J. Virol.*, 61:1738–1742 (1987); and J. F. Rodriguez et al, *Proc. Natl. Acad., Sci. USA*, 83:9566–9570 (1986)]. The genomic location of the AmEPV ORFs compared with that of the vaccinia virus ORFs suggests that the arrangement of essential "core genes", which are centrally located and colinear in many, if not all, of the vertebrate poxviruses on a more macroscopic scale, is quite different in the insect virus.

As set out in detail in the accompanying examples below, the spheroidin gene of AmEPV was identified through direct microsequencing of the protein, and the results were used for the design of oligonucleotide probes. Transcription of the spheroidin gene is inhibited by cycloheximide, suggesting it is a late gene. Consistent with this prediction are the observations that spheroidin transcripts were initiated within a TAATG motif (See FIG. 2, nucleotide #3077–3082) and that there was a 5' poly(A) sequence, both characteristic of late transcripts.

The AmEPV tk DNA sequence, including flanking and regulatory sequence, is reported in FIG. 3, as spanning nucleotides #1 through 1511 [SEQ ID NO:8]. Within this sequence, the tk gene coding sequence spans nucleotides #234 to 782 [SEQ ID NO:28] (transcribed right to left on FIG. 3). Another fragment of interest may include nucleotides #783 through #851 [SEQ ID NO:29] of that sequence or fragments thereof. A fragment likely to contain the promoter regions spans nucleotide #750–890 [SEQ ID NO:30]. Other regions of that sequence have also been identified as putative coding regions for other structural or regulatory genes associated with tk. These other fragments of interest include the following sequences (transcribed left to right on FIG. 3: nucleotide #18 through 218 [SEQ ID NO:31] encoding ORF Q1 [SEQ ID NO:10]); and nucleotide #852 through 1511 [SEQ ID NO:32] encoding ORF Q3 [SEQ ID NO:10].

The location of the AmEPV tk gene maps in the EcoRI-Q fragment near the left end of the physical map of the AmEPV genome (FIG. 1) [see, also, R. L. Hall et al, *Arch. Virol.*, 110:77–90 (1990), incorporated by reference herein]. Because of the orientation of the gene within the AmEPV genome, transcription of the gene is likely to occur toward the terminus. There are believed to be similar tk genes, or variations thereof, in other systems, including mammalian systems. As set out in detail in the examples below, the tk gene of AmEPV was identified through direct microsequencing of the protein, and the results were used for the design of oligonucleotide probes.

The term "polynucleotide sequences" when used with reference to the invention can include the entire EPV spheroidin or tk genes with regulatory sequences flanking the coding sequences. The illustrated AmEPV sequences are also encompassed by that term. Also included in the definition are fragments of the coding sequences with flanking regulatory sequences. The definition also encompasses the regulatory sequences only, e.g., the promoter sequences, transcription sites, termination sequences, and other regulatory sequences.

Sequences of the invention may also include all or portions of the spheroidin or tk genes linked in frame to a heterologous gene sequence. Additionally, polynucleotide sequences of the invention may include sequences of the spheroidin or tk genes into which have been inserted a foreign or heterologous gene sequence, so that the EPV sequences flank the heterologous gene sequence.

Polynucleotide sequences of this invention also include sequences which are capable of hybridizing to the sequences of FIGS. 2 and 3, under stringent conditions, which sequences retain the same biological or regulatory activities as those of the figures. Also sequences capable of hybridizing to the sequences of FIGS. 2 and 3 under non-stringent conditions may fall within this definition providing that the biological or regulatory characteristics of the sequences of FIGS. 2 and 3, respectively, are retained. Examples of stringent and non-stringent conditions of hybridization are conventional [See, e.g., Sambrook et al, *Molecular Cloning A Laboratory Manual*, 2d edition, Cold Spring Harbor Laboratory, Cold Spring Harbor, N.Y. (1989)].

Similarly, polynucleotide sequences of this invention also include allelic variations (naturally-occurring base changes in the EPV species population which may or may not result in an amino acid change) of DNA sequences encoding the spheroidin or tk protein sequences or DNA sequences encoding the other ORFs or regulatory sequences illustrated in FIGS. 2 and 3. Similarly, DNA sequences which encode spheroidin or tk proteins of the invention but which differ in codon sequence due to the degeneracies of the genetic code or variations in the DNA sequences which are caused by point mutations or by induced modifications to enhance a biological property or the usefulness of a desired polynucleotide sequence encoded thereby are also encompassed in the invention.

Utilizing the sequence data in FIGS. 2 or 3, as well as the denoted characteristics of spheroidin or thymidine kinase, it is within the skill of the art to obtain other DNA sequences encoding these polypeptides. For example, the structural gene may be manipulated by varying individual nucleotides, while retaining the correct amino acid(s), or varying the nucleotides, so as to modify the amino acids, without loss of enzymatic activity. Nucleotides may be substituted, inserted, or deleted by known techniques, including, for example, in vitro mutagenesis and primer repair.

The structural gene may be truncated at its 3'-terminus and/or its 5'-terminus while retaining its biological activity. It may also be desirable to ligate a portion of the polypeptide sequence to a heterologous coding sequence, and thus to create a fusion peptide.

The polynucleotide sequences of the present invention may be prepared synthetically or can be derived from viral RNA or from available cDNA-containing plasmids by chemical and genetic engineering techniques or combinations thereof which are standard in the art.

The AmEPV proteins, spheroidin, thymidine kinase and their respective regulatory sequences, as described herein, may be encoded by polynucleotide sequences that differ in sequence from the sequences of FIGS. 2 and 3 due to natural allelic or species variations. Thus, the terms spheroidin or tk polypeptides also refer to any of the naturally occurring sequences and various analogs, e.g., processed or truncated sequences or fragments, including the mature spheroidin or tk polypeptides and mutant or modified polypeptides or fragments that retain the same biological activity and preferably have a homology to FIG. 2 or 3, respectively, of at least 80%, more preferably 90%, and most preferably 95%.

Another aspect of the present invention is provided by the proteins encoded by the EPV spheroidin and tk polynucleotide sequences. Putative amino acid sequences of the two EPV proteins as well as additional putative proteins encoded by the ORFs of these sequences which are identified in FIGS. 2 and 3, respectively. EPV spheroidin has no significant amino acid homology to any previously reported protein, including the polyhedrin protein of baculovirus. Both spheroidin and tk are nonessential proteins, which makes them desirable as sites for insertion of exogenous DNA.

Comparison of the AmEPV tk amino acid sequence with other tk genes reveals that the AmEPV tk gene is not highly related to any of the vertebrate poxvirus tk genes (43.4 to 45.7%). The relatedness of the vertebrate tk proteins to AmEPV is still lower (39.3 to 41.0%), while African Swine Fever (ASF) showed the least homology of all the tk proteins tested (31.4%). Although ASF has many similarities to poxviruses, and both ASF and AmEPV infect vertebrate hosts, the tk genes indicate little commonality and/or indication of common origin stemming from invertebrate hosts.

The spheroidin and thymidine kinase polypeptide sequences may include isolated naturally-occurring spheroidin or tk amino acid sequences identified herein or deliberately modified sequences which maintain the biological or regulatory functions of the AmEPV polypeptides, respectively identified in FIGS. 2 and 3. Therefore, provided that the biological activities of these polypeptides are retained in whole or part despite such modifications, this invention encompasses the use of all amino acid sequences disclosed herein as well as analogs thereof retaining spheroidin or tk biological activity. Typically, such analogs differ by only 1, 2, 3, or 4 codon changes. Similarly, proteins or functions encoded by the other spheroidin or tk ORFs may include sequences containing minor amino acid modifications but which retain their regulatory or other biological functions.

Examples of such modifications include polypeptides with minor amino acid variations from the natural amino acid sequence of Entomopoxvirus spheroidin or thymidine kinase; in particular, conservative amino acid replacements.

Conservative replacements are those that take place within a family of amino acids that are related in their side chains. Genetically encoded amino acids are generally divided into four families: (1) acidic=aspartate, glutamate; (2) basic= lysine, arginine, histidine; (3) non-polar=alanine, valine, leucine, isoleucine, proline, phenylalanine, methionine, tryptophan; and (4) uncharged polar=glycine, asparagine, glutamine, cystins, serine, threonine, tyrosine. Phenylalanine, tryptophan, and tyrosine are sometimes classified jointly as aromatic amino acids. For example, it is reasonable to expect that an isolated replacement of a leucine with an isoleucine or valine, an aspartate with a glutamate, a threonine with a serine, or a similar conservative replacement of an amino acid with a structurally related amino acid will not have a major effect on biological activity, especially if the replacement does not involve an amino acid at an active site of the polypeptides.

As used herein, the term "polypeptide" refers to a polymer of amino acids and does not refer to a specific length of the product; thus, peptides, oligopeptides, and proteins are included within the definition of polypeptide. This term also does not refer to or exclude post-expression modifications of the polypeptide, for example, glycosylations, acetylations, phosphorylations and the like. Included within the definition are, for example, polypeptides containing one or more analogs of an amino acid (including, for example, unnatural amino acids, etc.), polypeptides with substituted linkages, as well as other modifications known in the art, both naturally occurring and non-naturally occurring.

The proteins or polypeptides of the present invention may be expressed in host cells and purified from the cells or media by conventional means [Sambrook et al, *Molecular Cloning. A Laboratory Manual*, 2d edition, Cold Spring Harbor Laboratory, Cold Spring Harbor, N.Y. (1989)].

This invention also relates to novel viral recombinant polynucleotide molecules or vectors, which permit the expression of heterologous genes in a selected host cell. Such a polynucleotide vector of the invention comprises the polynucleotide sequence encoding all or a portion of the spheroidin or tk gene, the RNA polymerase from a selected poxvirus, and the polynucleotide sequence encoding a desired heterologous gene. Preferably, the sequence includes the regulatory region, and most preferably, the promoter region, of either the EMV spheroidin or tk gene. In addition, the source of the polymerase is not limited to EMV; rather, any poxvirus RNA polymerase may be utilized.

Therefore, the viral vectors may contain other viral elements contributed by another poxvirus, either vertebrate or invertebrate, with the only EPV sequences being provided by the presence of the EPV spheroidin or tk gene sequences, or fragments thereof. Numerous conventional expression viral vectors and expression systems are known in the art. Particularly desirable vectors systems are those of vertebrate or invertebrate poxviruses. The Entomopoxvirus spheroidin and tk gene regulatory sequences may be used in other virus vector systems which contain a poxvirus RNA polymerase to enhance the performance of those systems, e.g., in vaccinia vectors. Methods for the construction of expression systems, in general, and the components thereof, including expression vectors and transformed host cells, are within the art. See, generally, methods described in standard texts, such as Sambrook et al, supra. The present invention is therefore not limited to any particular viral expression system or vector into which a polynucleotide sequence of this invention may be inserted, provided that the vector or system contains a poxvirus RNA polymerase.

The vectors of the invention provide a helper independent vector system, that is, the presence or absence of a functional spheroidin or tk gene in a poxvirus contributing elements to the vector, e.g., contributing the RNA polymerase, does not affect the usefulness of the resulting recombinant viral vector. Because both spheroidin and tk are non-essential genes, the viral vectors of this invention do not require the presence of any other viral proteins, which in helper-dependent systems are contributed by additional viruses to coinfect the selected host cell.

Selected host cells Which, upon infection by the viral vectors will permit expression of the heterologous gene, include insect and mammalian cells. Specifically, if the viral vector comprises the EPV spheroidin or tk gene sequences of the invention inserted into any member of the family Entomopoxvirinae, e.g., EPVs of any species, the host cell will be limited to cells of insects normally infected by EPVs. If the viral vector comprises the EPV spheroidin or tk gene sequences of the invention inserted into a vertebrate poxvirus, such as vaccinia or swinepox, the host cells may be selected from among the mammalian species normally infected by the wild-type vertebrate poxvirus. Most desirably, such mammalian cells may include human cells, rodent cells and primate cells, all known and available to one of skill in the art.

According to one aspect of the subject invention, therefore, vectors of the present invention may utilize a fragment of the polynucleotide sequence of EPV spheroidin, particularly the promoter and ancillary regulatory sequences which are responsible for the naturally high levels of expression of the gene. Desirably, spheroidin sequences may be found within the sequence of FIG. 2 [SEQ ID NO:1], more particularly within the region of nucleotides #2781 through 3199 [SEQ ID NO:22]. Smaller fragments within that region may also provide useful regulatory sequences. The desired spheroidin promoter sequence can be utilized to produce large quantities of a desired protein by placing it in operative association with a selected heterologous gene in viral expression vectors capable of functioning in either a vertebrate or invertebrate host cell.

As used herein, the term "operative association" defines the relationship between a regulatory sequence and a selected protein gene, such that the regulatory sequence is capable of directing the replication and expression of the protein in the appropriate host cell. One of skill in the art is capable of operatively associating such sequences by resort to conventional techniques.

Where the spheroidin polynucleotide sequence in the vector contains all or a portion of the spheroidin coding sequence in association with, or linked to, the heterologous gene, the resulting protein expressed in the host cell may be a fusion protein consisting of all or a portion of the spheroidin protein and the heterologous protein. Where the spheroidin polynucleotide sequence in the vector does not contain sufficient coding sequence for the expression of a spheroidin protein or peptide fragment, the heterologous protein may be produced alone.

In an analogous manner, the promoter and regulatory sequences of tk (FIG. 3 SEQ ID NO:8) may be employed in the construction of an expression vector to drive expression of a heterologous protein, or a fusion protein, in a selected known expression system. These tk regulatory sequences are desirably obtained from the sequence of FIG. 3 [SEQ ID NO:8], particularly in the fragment occurring between nucleotide #750 through 890 [SEQ ID NO:30]. Smaller fragments within that region may also provide useful regulatory sequences.

An advantage of the use of the novel EPV spheroidin or tk promoter sequences of this invention is that these regulatory sequences are capable of operating in a vertebrate poxvirus (e.g., vaccinia)-mammalian cell expression vector system. For example, the strong spheroidin promoter can be incorporated into the vaccinia virus system through homologous recombination. Unlike the promoter for the baculovirus polyhedrin gene, the promoter for the EPV spheroidin gene can be utilized directly in the vaccinia or swinepox virus expression vector.

To construct a vector according to the present invention, the spheroidin or tk polynucleotide sequence may be isolated and purified from a selected Entomopoxvirus, e.g., AmEPV, and digested with appropriate restriction endonuclease enzymes to produce a fragment comprising all or part of the spheroidin or tk gene. Alternatively such a fragment may be chemically synthesized.

Still alternatively, the desired AmEPV sequences may be obtained from bacterial cultures containing the plasmids pRH512, pMEGtk-1 or pRH7. The construction of the plasmid pRH512 is described in the examples below. This plasmid contains the 4.51 kb BglII fragment AmEPV DNA sequence inserted into a BamHI site in the conventional vector pUC9. The plasmid pRH7 was constructed by digesting AmEPV genomic DNA, obtained as described in Example 1, with Bsp1286I, and the resulting fragments with HaeII. T4 DNA polymerase is employed to blunt end the AmEPV DNA and the fragment containing the spheroidin gene is ligated to the large fragment of a SmaI digested pUC9 fragment. This fragment contains the entire spheroidin open reading frame and some flanking sequence, included within the nucleotide sequence spanning #2274–6182 [SEQ ID NO:33] of FIG. 2. The construction of plasmid pMEGtk-1 comprising the regulatory sequences of the tk gene as well as the structural gene is described below in the Example 8. It was constructed by inserting the EcoRI-Q fragment of AmEPV into the conventional vector pUC18.

Bacterial cultures containing plasmids pRH512, pMEG tk-1, and pRH7 have been deposited in the American Type Culture Collection, 12301 Parklawn Drive, Rockville, Md., USA. The deposited cultures are as follows:

| Culture | Accession No. | Deposit Date |
|---|---|---|
| *E. coli* SURE strain (Stratagene) pMEG-tk1 | ATCC 68532 | 26 Feb 91 |
| *E. coli* SURE strain (Stratagene) pRH512 | ATCC 68533 | 26 Feb 91 |
| *E. coli* SURE strain (Stratagene) pRH7 | ATCC | |

The plasmids can be obtained from the deposited bacterial cultures by use of standard procedures, for example, using cleared lysate-isopycnic density gradient procedures, and the like.

These ATCC deposits were made under conditions that assure that access to the cultures will be available during the pendency of this patent application to one determined by the Commissioner of Patents and Trademark to be entitled thereto under 37 CFR1.14 and 35 USC 122. The deposits will be available as required by foreign patent laws in countries wherein counterparts of the subject application, or its progeny, are filed. However, it should be understood that the availability of a deposit does not constitute a license to practice the subject invention in derogation of patent rights granted by government action.

Further, the subject culture deposit will be stored and made available to the public in accord with the provisions of the Budapest Treaty for the Deposit of Microorganisms, i.e., it will be stored with all the care necessary to keep it viable and uncontaminated for a period of at least five years after the most recent request for the furnishing of a sample of the deposit, and in any case, for a period of at least 30 (thirty) years after the date of deposit or for the enforceable life of any patent which may issue disclosing the culture. The depositor acknowledges the duty to replace the deposit should the depository be unable to furnish a sample when requested, due to the condition of the deposit. All restrictions on the availability to the public of the subject culture deposit will be irrevocably removed upon the granting of a patent disclosing it.

The molecular biology procedures referred to herein in describing construction of the vectors of this invention are standard, well-known procedures. The various methods employed in the preparation of the plasmid vectors and transformation or infection of host organisms are well-known in the art. These procedures are all described in, for example, Sambrook et al, cited above. Thus, it is within the skill of those in the genetic engineering art to extract DNA from microbial cells, perform restriction enzyme digestions, electrophorese DNA fragments, tail and anneal plasmid and insert DNA, ligate DNA, transform cells, prepare plasmid DNA, electrophorese proteins, and sequence DNA.

Because the AmEPV genome has no known unique restriction sites into which selected genes may be effectively introduced in a site-specific manner so as to be under the control of the spheroidin or tk promoter sequences, such restriction sites must be introduced into desired sites in the selected EPV polynucleotide sequence. For example, the unique BstB1 site located at nucleotide #3172 downstream from the start of the spheroidin gene is the closest site to genetically engineer a usable insertion sequence for cloning. Therefore, restriction sites closer to the initiating Met of the spheroidin gene must be deliberately inserted.

Methods for the insertion of restriction sites are known to those of skill in the art and include, the use of an intermediate shuttle vector, e.g., by cloning the EPV sequence into the site of an appropriate cloning vehicle. It will be recognized by those skilled in the art that any suitable cloning vehicle may be utilized provided that the spheroidin or tk gene and flanking viral DNA may be functionally incorporated.

A spheroidin shuttle vector may be constructed to include elements of the spheroidin structural gene, a cloning site located or introduced in the gene to enable the selected heterologous gene to be properly inserted into the viral genome adjacent to, and under the control of, the spheroidin promoter, and flanking viral DNA linked to either side of the spheroidin gene to facilitate insertion of the spheroidin-foreign gene-flanking sequence into another expression vector. The presence of flanking viral DNA also facilitates recombination with the wild type Entomopoxvirus, allowing the transfer of a selected gene into a replicating viral genome.

The shuttle vectors may thereafter be modified for insertion of a selected gene by deleting some or all of the sequences encoding for spheroidin or tk synthesis near the respective transcriptional start sites. Examples of such sites in spheroidin are nucleotides #3077 and 3080 and in tk includes nucleotide #809. Conventional procedures are available to delete spheroidin or tk coding sequences.

As an alternative to or in addition to the restriction site, a variety of synthetic or natural oligonucleotide linker sequences may be inserted at the site of the deletion. A polynucleotide linker sequence, which may be either a natural or synthetic oligonucleotide, may be inserted at the site of the deletion to allow the coupling of DNA segments at that site. One such linker sequence may provide an appropriate space between the two linked sequences, e.g., between the promoter sequence and the gene to be expressed. Alternatively, this linker sequence may encode, if desired, a polypeptide which is selectively cleavable or digestible by conventional chemical or enzymatic methods. For example, the selected cleavage site may be an enzymatic cleavage site, including sites for cleavage by a proteolytic enzyme, such as enterokinase, factor Xa, trypsin, collegenase and thrombin. Alternatively, the cleavage site in the linker may be a site capable of being cleaved upon exposure to a selected chemical, e.g. cyanogen bromide or hydroxylamine. The cleavage site, if inserted into a linker useful in the sequences of this invention, does not limit this invention. Any desired cleavage site, of which many are known in the art, may be used for this purpose. In another alternative, the linker sequence may encode one or a series of restriction sites.

It will be recognized by those skilled in the art who have the benefit of this disclosure that linker sequences bearing an appropriate restriction site need not be inserted in place of all or a portion of the spheroidin structural sequence, and that it would be possible to insert a linker in locations in the Entomopoxvirus genome such that both the sequence coding for the selected polypeptide and the spheroidin structural sequence would be expressed. For instance, the sequence coding for the selected polypeptide could be inserted into the tk gene in place of all or a portion of the tk structural sequence and under the transcriptional control of the tk promoter.

Polymerase chain reaction (PCR) techniques can also be used to introduce convenient restriction sites into the EPV DNA, as well as to amplify specific regions of the EPV DNA. These techniques are well known to those skilled in this art. See, for example, *PCR Protocols: A Guide to Methods and Applications*, M. A. Innis, D. H. Gelfand, J. J. Shinsky, and T. J. White, (1990).

By use of these techniques, a variety of alternative modified shuttle vectors into which a selected gene or portion thereof may be incorporated may be suitably utilized in the present invention.

As one embodiment of the invention, therefore, the polynucleotide sequence, described above, may be used as a shuttle vector to transfer a selected heterologous gene to a selected virus. In this embodiment, the polynucleotide sequence encoding the EMV spheroidin gene or EMV tk gene, or a fragment thereof, is linked to a heterologous gene. The polynucleotide sequence further contains a flanking region on either side of the spheroidin-heterologous gene or tk-heterologous gene to enable ready transfer into a selected virus. This resulting construct is termed a cassette. Such a flanking region may be derived from EPV, or alternatively, may be complementary to the target virus. For example, if it is desirable to insert a selected heterologous gene into a vaccinia virus to create a recombinant virus, one would utilize flanking regions complementary to the targeted vaccinia virus. Similarly if the heterologous gene is inserted within the EPV spheroidin or tk gene, so that the selected EPV regulatory sequence and heterologous gene are flanked by the EPV gene's own sequences, this cassette may be used for transfer into a wild type EPV having homologous sequences to the flanking sequences.

The insertion or linkage of the foreign gene into the tk or spheroidin sequences of the present invention or the linkage of flanking sequences foreign to the spheroidin or tk genes may be accomplished as described above. The vectors of the subject invention may use cDNA clones of foreign genes, because poxvirus genes contain no introns, presumably as a consequence of a totally cytoplasmic site of infection.

In accordance with standard cloning techniques, any selected gene may be inserted into the vector at an available restriction site to produce a recombinant shuttle vector. Virtually any gene of interest could be inserted into the vectors described herein in order to obtain high expression of the desired protein. Restriction sites in the fragment may thereafter be removed so as to produce a preferred spheroidin or tk shuttle vector, having one or more cleavage or cloning sites located in the 3' direction downstream from the spheroidin promoter sequence. Thus, the present invention is not limited by the selection of the heterologous gene.

Alternatively, a vector of this invention may comprise a heterologous gene which is inserted into all or a portion of the EMV spheroidin or tk protein encoding sequence to interrupt the protein's natural processing. However, when the vector is transferred to another virus which contains a wild-type spheroidin or tk gene, expression of the inserted heterologous gene is obtained. Thus, the Entomopoxvirus spheroidin gene (FIG. 2 SEQ ID NO:1) and/or the tk gene (FIG. 3 SEQ ID NO:8) can be used as the location for the insertion of exogenous or heterologous DNA in any of the above-mentioned expression systems. A shuttle vector so constructed may be useful as a marker for research and production techniques for identifying the presence of successfully integrated heterologous genes into the selected expression system.

The tk gene is a particularly desirable site for insertion of a selected heterologous gene. Unlike spheroidin, tk is produced early in infection and in lesser quantities. Additionally, many poxviruses possess tk genes which may be sufficiently homologous to the EPV tk to provide easy recombination. For example, in vaccinia virus expression. systems for mammalian cells, the vaccinia tk gene is a common insertion site. Therefore, the use of this gene is particularly desirable for construction of a shuttle vector to shuttle selected genes directly between vector systems. More specifically, a foreign gene may be desirably inserted into the EPV tk gene sequence between nucleotide #460 and #560 (See FIG. 3).

Insertion of cassettes containing foreign genes into wild-type poxviruses can be accomplished by homologous recombination. The homologous recombination techniques used to insert the genes of interest into the viruses of the invention are well known to those skilled in the art. The shuttle vectors, when co-infected into host cells with a wild-type virus, transfer the cassette containing the selected gene into the virus by homologous recombination, thereby creating recombinant virus vectors.

Expression of a selected gene is accomplished by infecting susceptible host insect cells with the recombinant viral vector of this invention in an appropriate medium for growth. An EPV expression vector propagated is propagated in insect cells or insects through replication and assembly of infectious virus particles. These infectious vectors can be used to produce the selected gene in suitable insect cells, thus facilitating the efficient expression of the selected DNA sequence in the infected cell. If the EPV spheroidin gene (or tk gene)—heterologous gene fragment is inserted into a vertebrate poxvirus by the same methods as described above, the recombinant virus may be used to infect mammalian cells and produce the heterologous protein in the mammalian cells.

For example, a gene inserted into the tk site of a vaccinia virus system could be transferred directly to the tk locus of an, Entomopoxvirus vector of the subject invention or vice versa. This shuttling could be accomplished, for example, using homologous recombination. Similarly insertion of a selected gene into the spheroidin gene or tk gene in a viral vector permits the gene to be shuttled into other viruses having homologous spheroidin or tk sequences, respectively.

The following description illustrates an exemplary vector of this invention, employing the gene coding for human β-interferon (IFN-β) synthesis as the heterologous gene. A DNA fragment containing the IFN-β gene is prepared conventionally with restriction enzyme digested or blunt ended termini and cloned into a suitable site in the AmEPV spheroidin gene, into which a restriction site has been engineered by the methods described above.

The insertion of the IFN-β gene produces a hybrid or fused spheroidin-IFN-β gene capable of producing a fused polypeptide product if only a portion of the spheroidin gene was deleted as described above. If the entire spheroidin structural sequence was deleted, only interferon will be produced. Further, the hybrid gene may comprise the spheroidin promoter, the IFN-β protein coding sequences, and sequences encoding a portion of the polypeptide sequence of the spheroidin protein, provided all such coding sequences are not deleted from the particular shuttle vector utilized.

The resulting shuttle vector contains the AmEPV spheroidin gene sequence coupled to the IFN-β gene. The hybrid spheroidin-IFN-β gene of the recombinant shuttle vector is thereafter transferred into the genome of an appropriate Entomopoxvirus, such as the preferred Entomopoxvirus AmEPV, to produce a recombinant viral expression vector capable of expressing the gene encoding for β-interferon in a host insect cell. Transfer of the hybrid gene to a wild-type virus is accomplished by processes which are well known;to those skilled in the art. For example, appropriate insect cells may be infected with the wild type Entomopoxvirus. These infected cells are then transfected with the shuttle vector of the subject invention. These procedures are described, for example, in *DNA Cloning: A Practical Approach*, Vol. II, Edited by D. M. Glover, Chapter 7, 1985. A person skilled in the art could choose appropriate insect cells to be used according to the subject invention. By way of example, salt marsh caterpillars and cultured gypsy moth cells can be used.

During replication of the AmEPV DNA after transfection, the hybrid gene is transferred to the wild-type AmEPV by homologous recombination between the recombinant shuttle vector and AmEPV DNA. Accordingly, a mixture is produced comprising wild-type, nonrecombinant EPVs and recombinant EPVs capable of expressing the IFN-β gene.

While transfection is the preferred process for transfer of the hybrid gene into the EPV genome, it will be understood by those skilled in the art that other procedures may be suitably utilized so as to effect the insertion of the gene into the EPV genome and that recombination may be accomplished between the recombinant shuttle vector and other strains of EPV (or other poxviruses) so long as there is sufficient homology between the sequence of the hybrid gene and the corresponding sequence of the other strain to allow recombination to occur.

The preferred recombinant AmEPV expression vector, comprising a hybrid spheroidin-IFN-β gene incorporated into the AmEPV genome, can thereafter be selected from the mixture of nonrecombinant and recombinant Entomopoxviruses. The preferred, but by no means only, method of selection is by screening for plaques formed by host insect cells infected with viruses that do not produce viral occlusions. Selection may be performed in this manner because recombinant EPV viruses which contain the spheroidin or tk protein coding sequences interrupted by the heterologous gene are defective in the production of viral occlusions due to the insertional inactivation of the spheroidin gene.

Also, the selection procedure may involve the use of the β-galactosidase gene to facilitate color selection. This procedure involves the incorporation of the *E. coli* β-galactosidase gene into the shuttle vector and is well known to those skilled in the art. This technique may be of particular value if the exogenous DNA is inserted into the tk gene so that the spheroidin gene is still expressed. It will be recognized by those skilled in the art that alternative selection procedures may also be utilized in accordance with the present invention.

Accordingly, the DNA from a recombinant virus is thereafter purified and may be analyzed with appropriate restriction enzymes, or PCR technology, to confirm that the recombinant AmEPV vector has an insertion of the selected gene in the proper location.

The vectors and methods provided by the present invention are characterized by several advantages over known vectors and vector systems. Advantageously, such EPV viral vectors of the present invention are not oncogenic or tumorigenic in mammals. Also, the regulatory signals governing *Amsacta moorei* Entomopoxvirus (AmEPV) gene expressions are similar to those of vaccinia. Therefore, it is possible to transfer the strongly expressed spheroidin gene, or the thymidine kinase gene, as an expression cassette, not only in insect cells, but for use in vertebrate poxviruses such as vaccinia and swinepox virus.

Based on reported data with vaccinia, herpes and baculovirus vector systems, which suggest that up to 30 kb can be transferred without disrupting the vector viability, the normal limitation on the amount of exogenous DNA which can be packaged into a virus is not anticipated to be encountered when using the novel EPV vectors and methods of the subject invention.

Another advantage is that for the novel vectors of the subject invention, the transcription and translation of foreign proteins is totally cytoplasmic. Still another advantage lies in the expression power of the EPV spheroidin regulatory sequences, which when in operative association with a heterologous gene in a vector of this invention, should produce high levels of heterologous protein expression in the selected host cell.

The EPV vectors of this invention and methods for employing them to express selected heterologous proteins in insect or mammalian cells, as described above, are characterized by the advantage of replication in insect cells, which avoids the use of mammalian viruses, thereby decreasing the possibility of contamination of the product with mammalian virus. The expression system of this invention is also a helper independent virus expression vector system. These two characteristics are shared by known baculovirus expression systems. However, as shown in Table 1, the EPV expression vector system (EEVS) using the vectors of this invention has some important distinguishing features compared to the baculovirus expression systems (BEVS).

TABLE 1

Differences between EEVs and BEVS

| | EEVs | BEVS |
|---|---|---|
| Site of replication: | cytoplasm | nucleus |
| Virus family: | Poxviridae | Baculoviridae |
| Sites for insertion of foreign genes | spheroidin & thymidine kinase (tk) | polyhedrin & p10 |
| Shuttle possibilities between vertebrate and insect systems: | yes (Orthopoxviruses) (Leporipoxviruses) (Suipoxviruses) (Avipoxviruses) | No mammalian counterparts. Baculovirus is not known to contain a tk gene. Polyhedrin is not found in mammalian systems. |

The present invention also provides a method for screening recombinant host cells for insertion of heterologous genes is provided by use of the recombinant viral polynucleotide molecules of this invention. The viral molecules containing the selected heterologous gene sequence linked to the polynucleotide sequence encoding less than all of the Entomopoxvirus spheroidin protein. The heterologous gene may be linked to the spheroidin or tk regulatory sequences in the absence of the complete coding sequences, or it may be inserted into the spheroidin or tk gene coding sequences, thus disrupting the coding sequence. The cell infected with the recombinant vector is cultured under conditions suitable for expression of the heterologous protein, either unfused or as a fusion protein with a portion of the spheroidin sequence. The absence of occlusion bodies which would ordinarily be formed by the expression of the intact spheroidin protein indicates the integration of the heterologous gene.

If the viral vector similarly contained either incomplete or interrupted EPV tk encoding sequence, the absence of thymidine kinase function (e.g., resistance to methotrexate or an analogue thereof) formed by the integration of the inactive thymidine kinase sequence indicates the insertion of the heterologous gene.

Alternatively, if a parent virus is deleted of part of its tk or spheroidin gene, and is thereafter mixed with a viral vector containing intact tk or spheroidin fused to the foreign gene, recombinants would express the methotrexate resistance or produce occlusion bodies, respectively, thus indicating integration of the active tk or spheroidin genes and the foreign gene.

The above-described selection procedures provide effective and convenient means for selection of recombinant Entomopoxvirus expression vectors.

Another embodiment of the present invention involves using novel EPV expression systems of the subject invention for insect control. Control of insect pests can be accomplished by employing the vectors and methods of the invention as described above. For example, a gene coding for an selected insect toxin may be inserted into the viral expression vector under the control of the spheroidin or tk regulatory sequences or within either of the two genes for purposes of recombination into a selected virus having homologous flanking regions.

Genes which code for insect toxins are well known to those skilled in the art. An exemplary toxin gene isolated from *Bacillus thuringiensis* (B.t.) can be used according to the subject invention. B.t. genes are described, for example, in U.S. Pat. Nos. 4,775,131 and 4,865,981. Other known insect toxins may also be employed in this method.

The resulting EPV vector containing the toxin gene is applied to the target pest or its surroundings. Advantageously, the viral vector will infect the target pest, and large quantities of the toxin will be produced, thus resulting in the control of the pest. Particularly large quantities of the toxin protein can be produced if the regulatory sequences of the Entomopoxvirus spheroidin gene are used to express the toxin.

Alternatively, the spheroidin gene can be left intact and the toxin gene inserted into a different Entomopoxvirus gene such as the tk gene. In this construct, the toxin will be produced by the system and then effectively coated or encapsulated by the natural viral production of spheroidin. This system thus produces a toxin which will advantageously persist in the environment to prolong the availability to the target pest.

In addition to the novel Entomopoxvirus expression vectors and methods for their use described herein, the subject invention pertains to the use of novel regulatory elements from Entomopoxvirus to construct novel chimeric vaccinia and swinepox vaccines and expression systems which are functional across genera of mammalian poxviruses. The polynucleotide sequences of the invention can also be used with viral vaccines, e.g., known vaccinia virus vaccines, to enhance the effectiveness of these vaccines. Such vaccines have been described for use in controlling rabies and other infectious diseases in mammals. Specifically, it is anticipated that the introduction of the EPV spheroidin promoter sequences into known viral vectors which are used to express selected proteins in a mammalian host in vivo may enable the powerful spheroidin promoter to increase expression of the protein in the viral vaccine. This aspect of the invention provides a significant improvement over other expression systems, including the baculovirus expression system (BEVS).

The following examples illustrate the compositions and procedures, including the best mode, for practicing the invention. These examples, should not be construed as limiting. All percentages are by weight and all solvent mixture proportions are by volume unless otherwise noted. The restriction enzymes disclosed herein can be purchased from Bethesda Research Laboratories, Gaithersburg, Md, or New England Biolabs, Beverly, Mass. The enzymes are used according to the instructions provided by the supplier. Klenow fragment of DNA polymerase, T4 polynucleotide kinase, and T4 DNA ligase were obtained from New England Biolabs and Promega.

EXAMPLE 1

PREPARATION OF AmEPV DNA

The replication of AmEPV has been described previously [R. H. Goodwin et al, *J. Invertebr. Pathol.*, 56:190–205 (1990)]. The gypsy moth (*Lymantria dispar*) cell line IPLB-LD-652 [Insect Pathology Laboratory, Agricultural Research Service, U.S. Department of Agriculture, Beltsville, Md.] is maintained at 26° to 28° C. in EX-CELL 400 [JRH Biosciences, Lenexa, Kans.] supplemented with 10% fetal bovine serum, 100 U of penicillin, and 100 µg of streptomycin per ml. Other insect cell lines are well known to those skilled in the art and can be used according to the subject invention.

The AmEPV inoculum for cell culturing was from an AmEPV-infected, freeze-dried *E. acrea* larva stored at −70° C. [R. L. Hall et al, *Arch. Virol.*, 110:77–90 (1990)]. The larva was crushed and macerated in 5 ml of EX-CELL 400 (with penicillin and streptomycin but without fetal bovine serum) to which 0.003 g of cysteine-HCl had been added to prevent melanization. The debris was pelleted at 200×g for 5 minutes, and the supernatant was passed through a 0.45-µm-pore-size filter.

The gypsy moth cells were infected with AmEPV by addition of the inoculum to a preconfluent monolayer of cells (about 0.1 to 1 PFU per cell), with occasional agitation of the dish during the first day. Infected cells were harvested 5 to 6 days postinfection.

AmEPV DNA was prepared from the infected cells by one of two methods. The first method involved in situ digestion of infected cells embedded within agarose plugs, after which the released cellular and viral DNAs were separated by pulsed-field electrophoresis [Bio-Rad CHEF-II-DR system]. IPLB-LD-652 cells were infected with first-cell-culture-passage AmEPV. Infected cells were harvested 6 days postinfection by centrifugation at 200×g for 5 minutes, rinsed, and resuspended in modified Hank's phosphate-buffered saline (PBS), which contained 15 g of glucose per liter, but no $Ca^{2+}$ or $Mg^{2+}$.

For embedding of the infected cells in agarose plugs, 1% SeaPlaque GTG agarose (prepared in modified Hank's PBS and equilibrated at 37° C.) was mixed 1:1 with infected cells to yield $5 \times 10^6$ cells per ml in 0.5% agarose. Digestion to release DNA was done by gentle shaking of the inserts in 1% Sarkosyl-0.5M EDTA-1 mg of proteinase K per ml at 50° C. for 2 days [C. L. Smith et al, *Methods Enzymol.*, 151:461–489 (1987)]. The CHEF-II-DR parameters for DNA separation were 180 V, a pulse ratio of 1, 50 initial and 90 second final pulse times, and a run time of 20 to 25 hours at 4° C. The separating gel was 1% SeaKem GTG agarose in 0.5× TBE buffer [Sambrook et al, supra]. Viral DNA bands were visualized by ethidium bromide staining and electroeluted [W. B. Allington et al, *Anal. Biochem.*, 85:188–196 (1978)]. The recovered DNA was used for plasmid cloning following ethanol precipitation.

The second method of viral DNA preparation used the extracellular virus found in the infected-cell-culture supernatant. The supernatant from 10-day-postinfection cell cultures was clarified by centrifugation at 200×g for 5 minutes. Virus was collected from the supernatant by centrifugation at 12,000×g. Viral pellets were resuspended in 6 ml of 1× TE. DNase I and RNase A (10 and 20 µg/ml final concentrations, respectively) were added, and the mixture was incubated at 37° C. for 30 minutes. The mixture was heated to 50° C. for 15 minutes. SDS and proteinase K (1% and 200 µg/ml, respectively) were then added. The sample was incubated to 50° C. overnight and extracted three times with buffer-saturated phenol and once with SEVAG [Sambrook et al, supra]. The DNA was ethanol precipitated and resuspended in 1× TE (pH 8).

For routine virus quantitation, 1 ml of an appropriate virus dilution (prepared in unsupplemented EX-CELL 400) was added to a preconfluent monolayer of cells in a 60 mm culture dish, with intermittent agitation over a 5 hour adsorption period at 26° to 28° C. The virus inoculum was removed, and 5 ml of a 0.75% SeaPlaque agarose [FMC BioProducts, Rockland, Me.] overlay prepared with 2× EX-CELL 400 and equilibrated at 37° C. was added to the monolayer. Plaques were visualized after 5 days of incubation at 26° C. by inspection with a stereomicroscope.

The DNA prepared according to either method was then cut with a variety of restriction endonuclease enzymes, e.g., Bam HI, EcoRI, HindIII, PstI and XhoI, generating the various fragments which appear on the physical map of FIG. 1. Hereafter, reference to each restriction fragment will refer to the enzyme and the applicable letter, e.g., BamHI-A through BamHI-E, EcoRI-A through EcoRI-S, etc.

EXAMPLE 2

ISOLATION OF THE SPHEROIDIN GENE

To localize the spheroidin gene, a purified preparation of occlusion bodies (OBs) from infected caterpillars was solubilized and subjected to sodium dodecyl sulfate-polyacrylamide gel electrophoresis (SDS-PAGE) [J. K. Laemmli, *Nature* (London), 227:680–685 (1970)] with a 4% acrylamide stacking gel and a 7.5% separating gel. The acrylamide used to prepare spheroidin for protein microsequencing was deionized with AG501X8 resin [Bio-Rad, Richmond, Calif.]. The gels were polymerized overnight at 4° C. For sample preparation, 2× Laemmli sample buffer consisting of 125 mM Tris-HCl (pH 6.8), 4% SDS (w/v), 10% β-mercaptoethanol (v/v), and 20% glycerol (v/v) was used.

OB suspension samples were diluted 1:1 with 2× Laemmli sample buffer and boiled for 5 minutes. Several lanes of an OB protein preparation were separated electrophoretically. The spheroidin protein (113 kDa) was the predominant protein of the purified OBs. Spheroidin within SDS-polyacrylamide gels was tested for glycosylation by periodic acid-Schiff staining [R. M. Zacharius et al, *Anal. Biochem.*, 30:149–152 (1969)].

Following electrophoretic separation, several lanes in the unstained gel were transferred to an Immobilon polyvinylidene difluoride (PVDF) membrane with a Bio-Rad TransBlot apparatus at 90 V for 2 hours in a buffer consisting of 10 mM morpholinepropanesulfonic acid (pH 6.0) and 20% methanol. Spheroidin was visualized on the PVDF membrane by Coomassie blue staining.

The region of the PVDF membrane containing spheroidin was excised from the membrane, and direct protein microsequencing was done with an Applied Biosystems gas-phase sequencer. Microsequencing of the intact protein was unsuccessful, presumably because the N terminus of the protein was blocked.

Cyanogen bromide cleavage was performed on samples of spheroidin eluted from the PVDF membrane to generate internal peptide fragments for sequencing. Major polypeptides of 15, 9, 8, and 6.2 kDa were produced.

EXAMPLE 3

SEQUENCING, HYBRIDIZATIONS

All DNA sequencing was done by the dideoxy chain termination method [F. Sanger et al, *Proc. Natl. Acad. Sci. USA*, 74:5463–5467 (1977)] with [α-$^{35}$S]dATP and Sequenase [US Biochemical, Cleveland, Ohio]. Standard sequencing reactions with Sequenase were carried out in accordance with the instructions of the supplier, US Biochemical.

A reliable amino acid sequence was obtained from the 9, 8, and 6.2 kDa polypeptides produced as described in Example 3. The 8 and 9 kDa polypeptides represented overlapping partial CNBr cleavage products which together yielded the longest continuous amino acid sequence: Met-Ala-(Asn or Arg)-Asp-Leu-Val-Ser-Leu-Leu-Phe-Met-(Asn or Arg)-(?)-Tyr-Val-(Asn?)-Ile-Glu-Ile-Asn-Glu-Ala-Val-(?)-(Glu?) [SEQ ID NO:34]. The amino acid sequence obtained from the 6.2 kDa fragment was Met-Lys-Ile-Thr-Ser-Ser-Thr-Glu-Val-Asp-Pro-Glu-Tyr-Val-(Thr or Ile)-Ser-(Asn?) [SEQ ID NO:35]. A partial sequence for the 15 kDa fragment was also obtained: (Asn?)-Ala-Leu-Phe-(Phe?) (Asn?)-Val-Phe [SEQ ID NO:36]. The question marks in the above sequences indicated undetermined or unconfirmed amino acids. All sequences were ultimately located within the spheroidin gene sequence.

EXAMPLE 4

PLASMID DRH512

A BglII AmEPV DNA library was prepared by digesting the genomic AmEPV DNA with BglII according to manufacturer's instructions. Plasmid PUC9 [GIBCO; Bethesda Research Labs] was BamHI-digested and phosphatase-treated. The genomic BglII cut AmEPV was shotgun cloned into the BamHI site of pUC9. *Escherichia coli* SURE [Stratagene, La Jolla, Calif.] was transformed by electroporation with a Bio-Rad Gene Pulser following the instructions provided by the manufacturer with the shotgun ligation, containing a variety of recombinant plasmids. Mini-preparations of plasmids were made by a conventional alkaline lysis procedure [Sambrook et al, Supra]. These plasmids were cut with EcoRI-SalI to release the insert and run on a gel. The resulting plasmid DNA was southern blotted to a nylon membrane, producing a number of clones.

Among the fragments produced from the restriction enzyme digestions of the genomic DNA was a 4.4 BglII fragment and an EcoRI-D fragment. In order to locate a desirable clone from among those produced above, the sequence derived from the 6.2 kDa CNBr fragment was used to design a degenerate oligonucleotide for use as a hybridization probe to locate the spheroidin gene in a clone. The nucleotide sequence of this probe called RM58 [SEQ ID NO:12] was GA5GT7GA6CC7GA5TA6GT, where 5 represents A or G, 6 represents C or T, and 7 represents A, G, C, or T. The peptide sequence of the probe was: Glu-Val-Asp-Pro-Glu-Tyr-Val [SEQ ID NO:37].

The DNA probe was radiolabeled either with [α-$^{32}$P] dCTP by the random oligonucleotide extension method [A. P. Feinberg et al, *Anal. Biochem.*, 132:6–13 (1983)] or with [γ-$^{32}$P]ATP and T4 polynucleotide kinase [Sambrook et al, supra]. These same procedures were used for all other oligonucleotide probes described below. Both types of probes were purified by passage through spun columns of Sephadex G-50.

Southern transfer was done with Hybond-N [Amersham]; the transferred DNA was fixed to the membrane by UV cross-linking. Southern hybridization was performed both with transferred DNA including the restriction fragments described above, as well as the BglII library of AmEPV DNA cloned into BamHI-digested plasmid pUC9 as described above. Hybridization with the oligonucleotide probe was done at 37° or 45° C. with BLOTTO [Sambrook et al, supra] and was followed by two washes at room temperature with 0.3M NaCl-0.06M Tris (pH 8)-2 mM EDTA for 5 minutes.

The RM58 probe [SEQ ID NO:12] hybridized to the 4.4 kb BglII fragment and the EcoRI-D fragment of AmEPV DNA [See FIG. 1]. A plasmid produced by the shotgun cloning, recombinant pRH512 (a BglII 4.56 kb fragment into the BamHI site of pUC9 which contains about 1.5 kb of the 5' end of the spheroidin gene) was also identified by this hybridization with the RM58 oligonucleotide [SEQ ID NO:12].

The 4.51 kb pRH512 BglII insert was isolated, radiolabeled as described above, and hybridized back to various AmEPV genomic digests as follows. The DNA-DNA hybridization was done at 65° C. with BLOTTO [Sambrook et al, supra] and was followed by two washes at room temperature with 0.3M NaCl-0.06M Tris (pH 8)-2 mM EDTA for 5 minutes, two washes for 15 minutes each at 65° C. but with 0.4% SDS added, and two washes at room temperature with 0.03M NaCl-0.06M Tris (pH 8)-0.2 mM EDTA. Hybridization was observed to the BamHI-A, EcoRI-D, HindIII-G and -J, PstI-A, and XhoI-B fragments of AmEPV DNA. The results of these hybridizations indicated that the 4.51 kb fragment in pRH512 was substantially identical to the 4.4 kb fragment produced by BglII digestion of genomic DNA.

The 4.51 kb BglII insert of pRH512 was thereafter sequenced by two procedures. One is the double-stranded plasmid sequencing method [M. Hattori et al, Anal. Biochem., 152:232–238 (1986)] performed with "miniprep" [Sambrook et al, supra] DNA and 1 pmol of universal, reverse, or custom-designed oligonucleotide primer in each sequencing reaction. Nested exonuclease II deletions [S. Henikoff, Methods Enzymol., 155:156–165 (1987)] were used to sequence plasmid pRH512 according to this method. Deletions were made from the universal primer end. For making these deletions, the DNA was cut with EcoRI, filled in with α-thiophosphate dNTPs [S. D. Puthey et al, Proc. Natl. Acad. Sci. USA, 78:7350–7354 (1981)] by use of the Klenow fragment of E. coli DNA polymerase, cut with SmaI, and treated with exonuclease III. Samples were removed every 30 seconds, re-ligated, and used to transform E. coli SURE cells by electroporation. Sequencing reactions were carried out with the universal primer.

When a primer complementary to that sequence was prepared and used to sequence back through the RM58 binding site (bases 3983 to 4002), the generated sequence, when translated, yielded the amino acid sequence generated from microsequencing the 6.2 kDa CNBr polypeptide fragment.

A second sequencing method was performed using a combination of M12 shotgun sequencing with standard and universal and reverse M13 primers into M13 phage to permit single-stranded sequencing as follows. Plasmid pRH512 was sonicated to produce random fragments, repaired with bacteriophage T4 DNA polymerase, and these fragments were shotgun cloned into SmaI-cut M13 mp19 [GIBCO]. Plaque lifts were screened with a radiolabeled probe prepared from the 4.5 kb insert found in pRH512 to identify appropriate clones for shotgun single stranded sequencing [see, e.g., Sambrook et al, supra]. Sequencing of the BglII insert of pRH512 isolated it to nucleotides #0 to 4505, thus extending the sequence 5' and 3' to the spheroidin gene (FIG. 2).

EXAMPLE 5

OBTAINING ADDITIONAL AmEPV SEQUENCE

A DraI AmEPV DNA library was prepared by digesting genomic DNA with DraI. These DraI fragments were shotgun cloned into SmaI-digested, phosphatase-treated vector M13mp19. Preparations of M13 virus and DNA were made by standard procedures [J. Sambrook et al, supra]. Ligation and heat shock transformation procedures were performed conventionally [Sambrook et al, supra.], resulting in the shotgun cloned fragments being transformed into the bacterial strain, E. coli UT481 [University of Tennessee] or the SURE strain.

Standard PCR [Innis et al, supra] with 400 ng of genomic AmEPV DNA as a template was used to prepare a probe to identify a 586 bp DraI clone from nitrocellulose filter replicas (plaque lifts) [Micron Separations, Inc.] of the M13 shotgun library of DraI-cut AmEPV fragments. This was done to isolate a clone spanning a central unsequenced region of the spheroidin gene. The standard PCR primers used for this reaction were RM92 [SEQ ID NO:15] (GCCTGGTTGGGTAACACCTC) and RM118 [SEQ ID NO: 16] (CTGCTAGATTATCTACTCCG). This sequencing revealed that there was a single HindIII site at base 931 and that the 2' end of the spheroidin open reading frame (ORF) was truncated (FIG. 2).

The technique of inverse polymerase chain reaction (PCR) [M. A. Innis et al, PCR protocol, a guide to methods and applications, Academic Press, Inc. San Diego, Calif. (1990)] was used with ClaI-digested AmEPV DNA fragments which were ligated into a circle, to prepare a probe to identify clones containing a flanking sequence or to verify the absence of an intervening sequence between adjacent clones. The primers used in inverse PCR were RM82 and RM83, which were taken from the pRH512 sequence. The sequence of RM82 [SEQ ID NO:13] was TTTCAAAT-TAACTGGCAACC and that of RM83 [SEQ ID NO:14] was GGGATGGATTTTAGATTGCG.

The specific PCR reaction conditions for 34 cycles were as follows: 30 seconds at 94° C. for denaturation, 30 seconds at 37° C. for annealing, and 1.5 minutes at 72° C. for extension. Finally, the samples were incubated at 72° C. to 8.5 minutes to complete extensions. The concentration of each primer was 1 μM.

The resulting 2.2 kb inverse PCR product was digested with ClaI, and a 1.7 kb fragment was gel purified. The 1.7 kb PCR fragment was sequenced with RM83 as a primer. Additional PCR primers were made to the new sequence as it was identified. The sequencing process employed Sequenase, 5 pmol of each primer, and 10 to 50 ng of template. Prior to being sequenced, the PCR products were chloroform extracted and purified on spun columns [Sambrook et al, supra] of Sephacryl S-400. The DNA sequence was assembled and aligned, and consensus sequence was produced [R. Staden, Nucleic Acids Res., 10:4731–4751 (1982)]. Both strands were completely sequenced; the PCR product sequence was verified by conventional sequence.

The relevant ClaI sites of the 1.7 kb PCR fragment are at positions 3485 to 6165. This fragment was radiolabeled and used as a probe to locate additional clones, i.e., pRH827 (307 bp), pRH85 (1.88 kb), and pRH87 (1.88 kb) from the BglII fragment library. Plasmids pRH85 and pRH87 were sequenced using the same nested exonuclease II deletions and sequencing procedure, as described above for pRH512. Sequencing of the inverse PCR products with custom-designed primers confirmed that plasmids pRH85 and pRH87 represented the same 1.88 kb BglII DNA insert in opposite orientations, but also revealed a missing 80 bp between pRH827 and pRH85. This 80 bp. DNA fragment was identified in the Drai fragment, as extending from bases 4543 to 5128 cloned into M13.

The orientation of the spheroidin ORF on the physical map is shown in FIG. 1. It is interesting to note that the 1.7 kb inverse PCR fragment only hybridized to the AmEPV HindIII-G fragment. The amino acid sequence derived from the 8 and 9 kDa overlapping CnBr-generated polypeptides is found from nucleotide positions 4883 to 4957 [SEQ ID NO:38]. That derived from the 6.2 kDa polypeptide is found from nucleotides 3962 to 4012 [SEQ ID NO:39], and that derived from the 15 kDa polypeptide is found from nucleotides 4628 to 4651 [SEQ ID NO:40]. Therefore, all sequences obtained from protein microsequencing were ultimately found to lie within the spheroidin ORF.

EXAMPLE 6

SPHEROIDIN GENE TRANSCRIPTION

The start site for spheroidin gene transcription was determined. A primer complementary to the spheroidin gene sequence beginning 65 bp downstream of the predicted initiating methionine was prepared and used for a series of primer extensions.

A. Preparation of RNA and primer extension reactions.

Six 150 mm dishes of subconfluent cells were prepared. The culture media were aspirated, and 2 ml of viral inoculum was added to each dish. The virus concentration was about 0.1 to 1 PFU per cell. The dishes were occasionally agitated during a 3 hour adsorption period. At the end of this period, the cells were rinsed with 5 ml of modified PBS. The media were replaced, and the infected cells were incubated for 72 hours at 27° C. Total RNA from the infected cells was isolated by the guanidinium thiocyanate-cesium chloride procedure [J. M. Chirgwin et al, *Biochemistry*, 18:5294–5299 (1979)].

Primer extension reactions were carried out with primer RM165 [SEQ ID NO:17], a 35-base oligonucleotide (GTTCGAAACAAGTATTTTCATCTTTTAAATAAATC) beginning and ending 100 and 65 bp downstream, respectively, of the initiating methionine codon found in the TAAATG motif. The primer was end labeled with [$\gamma$-$^{32}$P] ATP and T4 polynucleotide kinase and purified on a "spun column" [Sambrook et al, supra]. For annealing, 40 µg of total infected-cell RNA and $10^6$ cpm of radiolabeled primer were coprecipitated with ethanol. The pellet was resuspended in 25 µl of hybridization buffer [80% formamide, 40 mM piperazine-N,N'-bis(2-ethanesulfonic acid) (pH 6.4), 400 mM NaCl, 1 mM EDTA (pH 8.0)], denatured at 72° C. for 15 minutes, and incubated at 30° C. for 18 hours.

For primer extension, the RNA-primer hybrids were ethanol precipitated, resuspended, and used for five individual reactions. Each reaction contained 8 µg of total infected-cell RNA, 50mM Tris-HCl, (pH 8.3), 50mM KCl, 10 mM dithiothreitol, 10 mM MgCl$_2$, 4 U of avian myeloblastosis virus reverse transcriptase (Life Sciences), 8 U of RNasin (Promega), 0.25 mM each deoxynucleoside triphosphate (dNTP), and the appropriate dideoxynucleoside triphosphate (ddNTP), except for a control reaction, which contained no ddNTP. The dNTP/ddNTP ratios were 4:1, 5:1, 5:1, and 2:1, for the C, T, A, and G reactions, respectively. The reactions were carried out at 42° C. for 30 minutes.

One microliter of chase buffer (4 µl of 5 mM dNTP mixture and 1 µl of 20-U/µl reverse transcriptase) was added to each reaction mixture, which was then incubated for an additional 30 minutes at 42° C. Reaction products were separated on a sequencing gel (8% acrylamide containing 7M Urea) and visualized by autoradiography. Complementarity was observed until the AAA of the upstream TAAATG motif, indicating that transcription of the gene initiates within the TAAATG element of the proposed late promoter element. Immediately upstream is a 5' tract of noncoded poly(A) on the transcripts. The average length of the poly(A) is greater than 6 bp.

EXAMPLE 7

ANALYSIS OF SPHEROIDIN SEQUENCE

The spheroidin ORF (G5R) was initially identified by sequencing back through the RM58 oligonucleotide primer binding region as described above. Examination of the AmEPV spheroidin gene sequence (ORF G5R) revealed a potential ORF of 3.0 kb capable of encoding 1,003 amino acids or a protein of about 115 kDa. The ORF consists of 29% G+C, in contrast to the 18.5% reported for the entire AmEPV genome [Langridge, W. H. R., R. F. Bozarth, D. W. Roberts [1977] Virology 76:616–620]. Inspection of the 92 bases upstream of the initiating ATG revealed only 7 G or C residues. Also detected was the presence of known vertebrate poxvirus regulatory sequences within the 92 bp 5' of the spheroidin ORF. Included are three TTTT TNT early gene termination signals and TAAATG, which presumably represents a late transcription start signal used to initiate transcription and translation of the spheroidin gene. Several adjacent translation termination codone are also present within the 92 bp upstream of the spheroidin ORF.

Analysis of the sequence upstream of the spheroidin gene revealed four additional potential ORFs, G1L [SEQ ID NO:25], G2R [SEQ ID NO:23], G3L [SEQ ID NO:26], and G4R [SEQ ID NO:24], discussed above. The putative amino acid sequences of these ORFs are reported in FIG. 2 [SEQ ID NO: 2, 3; 4 and 5, respectively]. No significant homologies were found for the small potential polypeptides encoded by ORF G2R [SEQ ID NO23] or G3L [SEQ ID NO:26]. ORF G1L [SEQ ID NO:25], however, exhibited a significant degree of homology to ORF 17 found within the HindIII-I fragment of vaccinia virus, whose function is unknown. ORF G4R [SEQ ID NO:24] showed homology to ORF HM3 of capripoxvirus. In vaccinia virus, the ORF HM3 homolog was found very near the site of an incomplete ATI gene. The partial G6L ORF [SEQ ID NO:27] to the right of the spheroidin gene exhibited good homology to vaccinia virus NTPase I. Much better homology (78.4% identity over 162 amino acids) was found between the partial G6L ORF [SEQ ID NO:27] and NPH I of CbEPV [Yuen, L. et al, *Virol.*, 182:403–406 (1991)], another insect poxvirus.

EXAMPLE 8

Isolation and Sequencing of the AmEPV EcoRI-O Fragment Containing the tk Gene Sequencing of the EcoRI-Q fragment of genomic AmEPV of Example 1 was performed using techniques described above for spheroidin. The sequencing showed 1511 bp containing two complete and one partial ORF. Analysis of the DNA sequence of ORF Q2 [SEQ ID NO:28] indicates the sites where the identifying degenerate oligonucleotides (RM03 SEQ ID NO:18 and RM04 SEQ ID NO:19) might hybridize. Two oligonucleotides, RM03 and RM04, based on different but strongly conserved regions of the tk genes of several poxviruses and vertebrates [C. Upton et al, *J. Virol.*,60:920–927 (1986); D. B. Boyle et al, *Virology*, 156:35–365 (1987)] were prepared by the methods referred to above. RM03 was the 32-fold degenerate oligonucleotide [SEQ ID NO: 18] GA(T/C)GA(G/A)GG(G/A)GG(G/A)CA (G/A) TT(C/T)TT corresponding to the amino acid residues in the vaccinia tk protein from the aspartic acid at position 82 to the phenylalanine at position 87. RM04 [SEQ ID NO:19] was (GGNCCCATGTT(C/T)TCNGG with 32-fold degeneracy and corresponded to the region from the glycine at position 11 to the glycine at position 16 in vaccinia. These probes were radiolabeled as described above for the RH58 probe.

The AmEPV thymidine kinase (tk) gene was identified by hybridization with the degenerate oligonucleotide probes RM03 and RM04 to a Southern blot of the EcoRI-digested EPV DNA. The EcoRI band of interest (EcoRI-Q) was isolated, purified, and ligated into a pUC18 vector (GIBCO), previously digested with EcoRI and treated with calf intestinal alkaline phosphatase. Recombinant clones were identified by the size of the insert and by hybridization to the radioactive labeled oligonucleotide probes.

One such clone was called pMEGtk-1. The recombinant clones containing the EcoRI-Q fragment oriented in both directions relative to the pUC18 vector sequences were used for sequencing. Sequential nested deletions were generated by the method of Henikoff, cited above, as described for pRH512. These clones were used for sequencing the entire EcoRI-Q fragment.

Subsequently, these oligonucleotides and another, RM129 is a non-degenerate oligonucleotide GGTGCAAAATCT-GATATTTC [SEQ ID NO:20] prepared from the ORF Q1, were employed as sequencing primers to confirm their positioning as indicated in ORF Q2 [SEQ ID NO:28]. ORF Q2 potentially encodes for a protein of 182 amino acids (21.2 kDa) [SEQ ID NO:10]. ORF Q3 potentially encodes a polypeptide of at least 68 amino acids but is incomplete and is transcribed in the opposite direction from ORF Q2. ORF Q1 [SEQ ID NO:31] potentially encodes a small peptide of 66 amino acids (7.75 kDa) [SEQ ID NO:9].

Further analysis of the EcoRI-Q fragment reveals several other points. First, the A+T content is very high (80%). For ORF Q2, the 100 nucleotides upstream of the start codon for translation are 90% A+T. Some potential poxvirus transcription signals were found between ORFs Q1 and Q2. The five bases immediately preceding the start codon for ORF Q1 are TAAATG which comprise a consensus late poxvirus promoter. A potential poxvirus early transcription termination signal sequence (TTTTTAT) is located 2 nt past the translation stop codon of Q2.

The deduced amino acid sequence for the tk encoded by the ORF Q2 of the EcoRI-Q fragment can be compared to the tk genes for the poxviruses swine pox [W. M. Schnitzlein et al, Virol., 181:727–732 (1991); J. A. Feller et al, Virol., 183:578–585 (1991)]; fowlpox [Boyle et al., supra; M. M. Binns et al, J. Gen. Virol., 69:1275–1283 (1988)]; vaccinia [J. P. Weir et al, J. Virol., 46:530–537 (1983); D. E. Hruby et al, Proc. Natl. Acad. Sci. USA, 80:3411–3415 (1983)]; variola and monkeypox [J. J. Esposito et al, Virol., 135:561–567 (1984)]; capripoxvirus [P. D. Gershon et al, J. Gen. Virol., 70:525–533 (1989)]; Shope fibroma virus [Upton et al., supra]; the cellular thymidine kinases of humans [H. D. Bradshaw et al, Mol. Cell. Biol., 4:2316–2320 (1984); E. Flemington et al, Gene, 52:267–277 (1987)]; the tk of mouse [P. F. Lin et al, Mol Cell. Biol., 5:3149–3156 (1985)]; the tk of chicken [T. J. Kwoh et al, Nucl. Acids Res., 12:3959–3971 (1984)]; ASF [R. Blasco et al, Virol., 178:301–304 (1990); A.M. Martin Hernandez et al, J. Virol., 65:1046–1052 (1991)].

EXAMPLE 9

EXPRESSION OF THE AmEPV tk GENE IN A VACCINIA VIRUS

The AmEPV tk, gene was tested functionally by cloning the gene into a vaccinia virus strain tk⁻ mutant, as follows.

The EcoRI-Q fragment of AmEPV, described above, was inserted in both possible orientations into shuttle plasmid pHGN3.1 [D. D. Bloom et al, J. Virol., 65:1530–1542 (1991)] which had been isolated from bacterial cells by the alkaline lysis method. This EcoRI-Q DNA fragment contains the AmEPV tk open reading frame (ORF). The cloning was performed conventionally. The resulting plasmid was designated pHGN3.1/EcoRI-Q.

The plasmid was transfected by Lipofectin [GIBCO] as described specifically below into mammalian cells infected with vaccinia virus. The cells were either rat tk⁻, human 143 tk⁻, or CV-1 cell lines onto which the vaccinia virus VSC8 was propagated. These cells were maintained in Eagle's Minimal Essential Medium with Earle's salts [Massung et al, Virol., 180:347–354 (1991) incorporated by reference herein].

The VSC8 vaccinia strain [Dr. Bernard Moss] contains the $\beta$-galactosidase gene driven by the vaccinia $P_{11}$ promoter ($P_{11}$-Lac Z cassette) inserted into the viral tk gene. While VSC8 contains an inactive tk gene due to the insertion of the $\beta$-galactosidase, portions of the vaccinia tk sequence remain. VSC8 is thus tk- and, upon staining with X-Gal (5-bromo-4-chloro-3-indoyl-$\beta$-D-galactopyranoside), will form blue plaques ($\beta$-galactosidase positive).

Cells were grown to 80% confluence ($4 \times 10^6$ per 60 mm dish). Lipofectin solution (20 µg of Lipofectin in 50 µl of $dH_2O$) was added to 10 µg plasmid DNA (pHGN3.1/AmEPV EcoRI-Q) in 50 µl of $dH_2O$ and incubated for 15 minutes at room temperature. After a 2 hour period of viral adsorption (m.o.i. of 2, 37° C.), the monolayers were washed three times with serum-free OptiMEM. Three milliliters of serum-free OptiMEM was then added to each 60 mm dish. The Lipofectin/DNA mixture was slowly added dropwise with gentle swirling and incubated an additional 12 to 18 hours at 37° C. Fetal bovine serum was then added (10% final) and the infected cells were harvested at 48 hours postinfection.

Recombinant viruses, containing the EcoRI-Q fragment inserted into the hemagglutinin (HA) gene of vaccinia, were identified by hybridization of AmEPV EcoRI-Q fragments, radioactively labeled by procedures described above, to replicas of nitrocellulose "lifts" of virus plaques from the infected monolayer. Potential recombinants were isolated from replica filters and plaque-purified several times before testing.

The tk of AmEPV exhibits some degree of homology with the tk of vaccinia. To confirm that insertion of the AmEPV tk gene was within the HA gene of vaccinia rather than within residual tk sequences remaining in VSC8, the recombinants were examined by a series of Southern hybridizations to HindIII digests of the various viruses. When DNA from wild-type virus was hybridized to a vaccinia virus tk probe, hybridization was observed exclusively within the ≈5 kb HindIII-J fragment of AmEPV.

When either VSC8 or either of the AmEPV tk containing recombinants was examined using the vaccinia tk probe, hybridization occurred instead to an ≈8 kb fragment consistent with polymerase in the presence of radiolabeled substrates. Extension will terminate at the end of the PstI-F fragment.

The radiolabeled product was then hybridized to an EcoRI digest of AmEPV DNA. If orientation of the gene is such that the tk ORF reads toward the end of the genome, hybridization would be expected to the EcoRI-E fragment; whereas if the gene is read toward the center of the genome, hybridization would be expected to the EcoRI-I fragment.

The results indicate hybridization not only to the EcoRI-E fragment, but also to the EcoRI-A fragment. These results infer that the orientation of the tk gene is with reading toward the left end of the genome. Hybridization of the run-off extension product also to the EcoRI-A fragment is consistent with the presence of an inverted terminal repetition, common in poxviruses, with identical sequences residing in both the EcoRI-A and the EcoRI-E fragments.

The optimal growth temperature for AmEPV in the laboratory is 28° C., whereas that of the vertebrate poxviruses is 37° C. As described herein, when the AmEPV DNA fragment containing the entire tk gene was cloned into the tk⁻ strain of vaccinia virus, the recombinant virus was capable of growing at 37° C. in the presence of methotrexate [Sigma], indicative of a tk+ phenotype. This example demonstrates that the Entomopoxvirus tk gene can be successfully transferred into mammalian expression systems, and that AmEPV tk is functionally active over a considerable temperature range.

It should be understood that the examples and embodiments described herein are for illustrative purposes only. Various modifications or changes in light thereof will be suggested to persons skilled in the art by this specification. The subject invention encompasses recombinant polynucleotide sequences, plasmids, vectors, and transformed hosts which are equivalent to those which are specifically exemplified herein in that the characteristic expression features are retained in said equivalent constructs even if inconsequential modifications to the DNA sequence have been made. For example, it is within the skill of a person trained in the art to use a fragment of the spheroidin gene's non-coding region which is upstream of the structural gene in order to achieve the desired level of expression. Such fragments of the regulatory sequences fall within the scope of the current invention, so long as the desired level of expression which is characteristic of this system is retained. Furthermore, inconsequential changes to the nucleotide sequences can be made without affecting the disclosed functions of these sequences. Such modifications also fall within the scope of the current invention and are to be included within the spirit and purview of this application and the scope of the appended claims.

We claim:

1. An Entomopoxvirus spheroidin gene polynucleotide sequence free from association with other viral nucleotide sequences with which it is associated in nature, provided that in nature, said polynucleotide sequence encodes a spheroidin gene product of about 115 kilodaltons.

2. The sequence according to claim 1 wherein said polynucleotide sequence is a DNA sequence.

3. The sequence according to claim 1 wherein said sequence is derived from the *Amsacta moorei* Entomopoxvirus.

4. An Entomopoxvirus thymidine kinase gene polynucleotide sequence free from association with other viral nucleotide sequences with which it is associated in nature.

5. The sequence according to claim 4 wherein said polynucleotide sequence is a DNA sequence.

6. The sequence according to claim 4 wherein said sequence is derived from the *Amsacta moorei* Entomopoxvirus.

* * * * *

UNITED STATES PATENT AND TRADEMARK OFFICE
CERTIFICATE OF CORRECTION

PATENT NO. : 5,721,352
DATED : Feb. 24, 1998
INVENTOR(S) : Richard W. Moyer, et al It is certified that error appears in the above-identified patent and that said Letters Patent is hereby corrected as shown below:

Column 5, line 26: "HM30RF" should read --HM3 ORF--; and line 27: "HM30RF" should read --HM3 ORF--.

Column 8, line 8: "cystins" should read --cystine--.

Column 10, lines 40-50: should read

| Culture | Accession No. | Deposit Date |
|---|---|---|
| *E. coli* SURE strain (Stratagene) pMEG-tk1 | ATCC 68532 | 26 Feb 91 |
| *E. coli* SURE strain (Stratagene) pRH512 | ATCC 68533 | 26 Feb 91 |
| *E. coli* SURE strain (Stratagene) pRH7 | ATCC 68902 | 28 Jan 92 |

UNITED STATES PATENT AND TRADEMARK OFFICE
CERTIFICATE OF CORRECTION

PATENT NO.  : 5,721,352
DATED       : Feb. 24, 1998
INVENTOR(S) : Richard W. Moyer, et al It is certified that error appears in the above-identified patent and that said Letters Patent is hereby corrected as shown below:

Column 12, line 40: "Shinsky" should read --Sninsky--.

Column 13, line 57: "vector propagated is propagated" should read --vector is propagated--.

Column 14, line 3: "an, Entomopoxvirus" should read --an Entomopoxvirus--; and line 36: "known; to" should read --known to--.

Column 20, line 10: "PLASMID DRH512" should read --PLASMID pRH512--.

Column 21, line 25: "Puthey" should read --Putney--.

Column 22, line 46: "3485 to 6165." should read --3485 and 6165.--;

line 55: "80 bp. DNA" should read --80 bp DNA--; and line 56: "Drai" should read --*Dra*I--.

Column 24, line 15: "codone" should read --codons--;

line 22: "2, 3; 4 and 5," should read --2, 3, 4 and 5,--;

UNITED STATES PATENT AND TRADEMARK OFFICE
CERTIFICATE OF CORRECTION

PATENT NO. : 5,721,352
DATED : Feb. 24, 1998
INVENTOR(S) : Richard W. Moyer, et al It is certified that error appears in the above-identified patent and that said Letters Patent is hereby corrected as shown below:

Column 24, line 24: "[SEQ ID NO23]" should read --[SEQ ID NO:23]--;

line 39: "EcoRI-O" should read --EcoRI-Q--; and line 53: "35-365" should read --355-365--.

Column 25, line 22: "66amino" should read --66 amino--; and line 56: "tk, gene" should read --tk gene--.

Signed and Sealed this

Third Day of November, 1998

*Attest:*

BRUCE LEHMAN

*Attesting Officer*   Commissioner of Patents and Trademarks

SEQUENCE LISTING ( 1 ) GENERAL INFORMATION:

( i i i ) NUMBER OF SEQUENCES: 40

( 2 ) INFORMATION FOR SEQ ID NO:1:

( i ) SEQUENCE CHARACTERISTICS:
        ( A ) LENGTH: 6768 base pairs
        ( B ) TYPE: nucleic acid
        ( C ) STRANDEDNESS: double
        ( D ) TOPOLOGY: unknown ( i i ) MOLECULE TYPE: DNA (genomic)

( v i ) ORIGINAL SOURCE:
        ( A ) ORGANISM: Amsacta moorei entomopoxvirus ( i x ) FEATURE:
        ( A ) NAME/KEY: CDS
        ( B ) LOCATION: complement (65..1459)

( i x ) FEATURE:
        ( A ) NAME/KEY: CDS
        ( B ) LOCATION: 1474..2151

( i x ) FEATURE:
        ( A ) NAME/KEY: CDS
        ( B ) LOCATION: complement (2239..2475)

( i x ) FEATURE:
        ( A ) NAME/KEY: CDS
        ( B ) LOCATION: 2502..2987

( i x ) FEATURE:
        ( A ) NAME/KEY: CDS
        ( B ) LOCATION: 3080..6091

( i x ) FEATURE:
        ( A ) NAME/KEY: CDS
        ( B ) LOCATION: complement (6277..6768)

( x i ) SEQUENCE DESCRIPTION: SEQ ID NO:1:

```
AGATCTGATG   TTCTATATAT   AGTACAAATT   TGTATGATTA   ATTGATATTT   TAAAATTCAA        60

GATATTAAAT   ATTAGATTCT   AAACTATTCT   TCTCATTATC   AATATAACTA   TCATAATCAT       120

TTTTTATTTT   ACTACATACA   TTCATAATTC   TATTACTATT   TTTTTATAC    ATATCTATTA       180

ATTCCATAAA   CTTTTTATTT   TTTATATTAA   ATATTTCTAA   TGTATTTTTA   AATTCGTCAA       240

TACTATTAAT   ATCATATCTA   GAAATAAATA   ATGCACCTCT   ATAACTACTA   GCCAATAAAT       300

CACCAATAAA   ACTCATAGAA   TAATATAATT   TTTAAATTC    AAATTTAGAT   TTTATGTTGA       360

AATAAACTAT   ATAATATAAA   AATATTATAT   TAAACATACC   ACAATCGGGA   CTATCATATT       420
```

| | | | | | | |
|---|---|---|---|---|---|---|
| GTAATTCAAA | AGTATTAAAA | AAGTAATAAT | TTACATTTTT | AAATATATCA | TTTAAATATT | 480 |
| CTGATAGTAC | ATCAATGTAT | AAATAAGCAT | AATTAGTATT | AGGAGTACTA | TTGTAGTGTT | 540 |
| TATGGCTTTT | TATAGTCATA | TCAGATTCAA | TAAACATATA | TTTTTATTT | TGTTTTATAA | 600 |
| GTTCTGGTAT | ATAACCACTA | CTATTAAAAA | AGTATGCAGC | TTTTTATCT | TTATCAAAGT | 660 |
| GTTTATCTAT | TACGCAACAA | GTAAATGAT | CATTATAAAT | TATAGGAAAC | ATAAAAAATC | 720 |
| TTTTTTATC | ATTCATTAAA | AAAAATTTTA | CTCTATCTTC | AAGTTTATAG | CATCTCATAG | 780 |
| ATGAAGCTAC | TGTAGCAATA | TTTTTATCAG | TTTTTCAAA | TAAAATCAAA | TGAAAATAAT | 840 |
| CATAATCTGT | ATTAATCATA | GTTAATGGAT | ATATACAATT | ATATATATCT | CCCGAACTTA | 900 |
| ACCATGTAGA | TTTATCATGT | TTTCTTGGGT | AAGCTTAGG | TTTAGGATTA | AATCCCAAAG | 960 |
| GCGGTATTCC | TATTTGAGCA | TCCAAATCAT | CATAAATTGT | GGCAAATGTA | GAAAAATCTC | 1020 |
| TTGTTTTGGA | TAATTCTGAT | TTTAGAAAAG | ACTTTCTCAT | ATATACTAAT | GGAATGCCTT | 1080 |
| TATATTTTTT | AGATGTAATA | AAAGTATTAA | TATTTATATT | TTTATCTTGT | AAATATTTTT | 1140 |
| TTATAGTCCA | AAATAGAAAA | AATTTCTTT | TAATATTATT | TTCAAAATTA | ATATTATTAA | 1200 |
| TATGATTTGG | ATCTAAAACT | AATTCATTAT | ATAATATTTC | CAAGTATTTT | ATAGGTATAA | 1260 |
| ATGTTACTTT | ACCTCTTGTT | TCATCATCAT | CATCTATTTT | TTCTAATATA | GCTATATTTG | 1320 |
| CATTAGTATT | ATATTTAATA | GGATTTATAA | AATATACCAT | ATTATCTATT | TTACTAAAAA | 1380 |
| ATAACATAGA | CATAAAATTA | ATACCAGATT | CTGGCATTTT | TAAATTTTTA | TTTGGAAATC | 1440 |
| TTCTAATTTT | ATTATTCATT | ATTTATTTAA | TAA ATG TTT CTA GTT TAT TTC AAT | | | 1494 |
| | | | Met Phe Leu Val Tyr Phe Asn | | | |
| | | | 1                    5 | | | |

```
ACA TTT TTA ATA ATA ATT TTA TTA TTT GGT ATT ATA GGT ATT TAT ATA      1542
Thr Phe Leu Ile Ile Ile Leu Leu Phe Gly Ile Ile Gly Ile Tyr Ile
         10                  15                  20

TTA ACA TTT GTG TTT AAT ATA GAT TTT TTA ATA AAT AAT AAT AAA ATA      1590
Leu Thr Phe Val Phe Asn Ile Asp Phe Leu Ile Asn Asn Asn Lys Ile
     25                  30                  35

TAT ATA TTA TCA TAT AAC GCA ACT AAT ATA AAC AAT ATA AAT AAT TTA      1638
Tyr Ile Leu Ser Tyr Asn Ala Thr Asn Ile Asn Asn Ile Asn Asn Leu
 40                  45                  50                  55

AAT TTA TAC GAT TAT TCA GAT ATT ATA TTT TTG ACA AAT TTT AAC ATA      1686
Asn Leu Tyr Asp Tyr Ser Asp Ile Ile Phe Leu Thr Asn Phe Asn Ile
                 60                  65                  70

AAT AAT AAT CTT TTA GTA ACA CAA GCT AAT AAT TTA CAA GAT ATA CCA      1734
Asn Asn Asn Leu Leu Val Thr Gln Ala Asn Asn Leu Gln Asp Ile Pro
             75                  80                  85

ATA TTT AAT GTA AAT AAT ATT ATA TCT AAT CAA TAT AAT TTT TAT TCA      1782
Ile Phe Asn Val Asn Asn Ile Ile Ser Asn Gln Tyr Asn Phe Tyr Ser
         90                  95                 100

GCG TCT AGT AAT AAT GTA AAT ATA TTA TTA GGA TTA AGA AAA ACA TTA      1830
Ala Ser Ser Asn Asn Val Asn Ile Leu Leu Gly Leu Arg Lys Thr Leu
     105                 110                 115

AAT ATA AAT AGA AAT CCA TTT TTA TTA TTT AGA AAT ACA TCT CTA GCT      1878
Asn Ile Asn Arg Asn Pro Phe Leu Leu Phe Arg Asn Thr Ser Leu Ala
120                 125                 130                 135

ATA GTT TTC AAT AAT AAT GAA ACT TTT CAC TGT TAT ATA AGT TCA AAT      1926
Ile Val Phe Asn Asn Asn Glu Thr Phe His Cys Tyr Ile Ser Ser Asn
                 140                 145                 150

CAA AAT AGT GAT GTA TTA GAT ATA GTA TCA CAT ATA GAA TTT ATG AAA      1974
Gln Asn Ser Asp Val Leu Asp Ile Val Ser His Ile Glu Phe Met Lys
             155                 160                 165

TCT AGA TAT AAT AAA TAT GTA ATT ATA GGA GAA ATA CCC GTA AAT AAT      2022
Ser Arg Tyr Asn Lys Tyr Val Ile Ile Gly Glu Ile Pro Val Asn Asn
```

|   |   |   |   |   |   | 170 |   |   |   |   | 175 |   |   |   |   | 180 |   |   |      |
|---|---|---|---|---|---|---|---|---|---|---|---|---|---|---|---|---|---|---|------|

```
AAT ATA TCT ATT AAT AAT ATA TTA AAT AAT TTT GCT ATT ATA ACT AAT                 2070
Asn Ile Ser Ile Asn Asn Ile Leu Asn Asn Phe Ala Ile Ile Thr Asn
    185             190             195

GTG AGA TTA ATA GAT AAA TAT AAC TCT ATA ATA TCA TTT TTA AAT ATC                 2118
Val Arg Leu Ile Asp Lys Tyr Asn Ser Ile Ile Ser Phe Leu Asn Ile
200             205             210                 215

AAC GTA GGA ACA CTT TTT GTC ATA AAT CCA TAATATTTAG TAATAATCAC                   2168
Asn Val Gly Thr Leu Phe Val Ile Asn Pro
                220             225

TAACATATTT TTTATTAAAA TGAATAAAAT ATATATTGTT ATTGTCAATA TTTTATATCA               2228

TTTTACAGTC TTATTTTTTT TTTTGCTTT TAGGTATAAT TTTACCTTCT AAACGTTTAT                2288

CTCCCCAAAC ATCTACAGTA GATGGTTTAT TAGATTCTGT GTTATACACA TCTGCTGGAT               2348

TTGCGGCATT TGTATCCAAA CCATAATATC CAGGTCTATA ATTATCTTTA AAAACTGGG                2408

ATTGAGATAC TTCTTCAGTT TTTAAATTAT TAAAATATCC AAGATTATTT TTTTTGATG                2468

AAGACATAAT TGATATTATA ATACTTTATA GAT ATG TCA ATA TTT ATC TAC TAT                2522
                                    Met Ser Ile Phe Ile Tyr Tyr
                                      1                 5

ATT TTC AAC AAT AGA TTT TAT ATA TAT AAA AGA ATG AAT ACT GTA CAA                 2570
Ile Phe Asn Asn Arg Phe Tyr Ile Tyr Lys Arg Met Asn Thr Val Gln
        10              15              20

ATT TTA GTT GTC ATA TTA ATA ACA ACA GCA TTA TCT TTT CTA GTT TTT                 2618
Ile Leu Val Val Ile Leu Ile Thr Thr Ala Leu Ser Phe Leu Val Phe
    25              30              35

CAA TTA TGG TAT TAT GCC GAA AAT TAC GAA TAT ATA TTA AGA TAT AAT                 2666
Gln Leu Trp Tyr Tyr Ala Glu Asn Tyr Glu Tyr Ile Leu Arg Tyr Asn
40              45              50              55

GAT ACA TAT TCA AAT TTA CAA TTT GCG AGA AGC GCA AAT ATA AAT TTT                 2714
Asp Thr Tyr Ser Asn Leu Gln Phe Ala Arg Ser Ala Asn Ile Asn Phe
            60              65              70

GAT GAT TTA ACT GTT TTT GAT CCC AAC GAT AAT GTT TTT AAT GTT GAA                 2762
Asp Asp Leu Thr Val Phe Asp Pro Asn Asp Asn Val Phe Asn Val Glu
        75              80              85

GAA AAA TGG CGC TGT GCT TCA ACT AAT AAT AAT ATA TTT TAT GCA GTT                 2810
Glu Lys Trp Arg Cys Ala Ser Thr Asn Asn Asn Ile Phe Tyr Ala Val
    90              95              100

TCA ACT TTT GGA TTT TTA AGT ACA GAA AGT ACT GGT ATT AAT TTA ACA                 2858
Ser Thr Phe Gly Phe Leu Ser Thr Glu Ser Thr Gly Ile Asn Leu Thr
105             110             115

TAT ACA AAT TCT AGA GAT TGT ATT ATA GAT TTA TTT TCT AGA ATT ATA                 2906
Tyr Thr Asn Ser Arg Asp Cys Ile Ile Asp Leu Phe Ser Arg Ile Ile
120             125             130             135

AAA ATA GTA TAT GAT CCT TGT ACT GTC GAA ACA TCT AAC GAT TGT AGA                 2954
Lys Ile Val Tyr Asp Pro Cys Thr Val Glu Thr Ser Asn Asp Cys Arg
            140             145             150

TTA TTA AGA TTA TTG ATG GCC AAT ACA TCA TAAATACATT ATAATATTAT                   3004
Leu Leu Arg Leu Leu Met Ala Asn Thr Ser
        155             160

TATAATATCA ATCATAATTT TTATATATAT TTATCTAAA AGGACTTTTT ATTTTTATA                 3064

TATTAATAAT AATAA ATG AGT AAC GTA CCT TTA GCA ACC AAA ACA ATA AGA                3115
             Met Ser Asn Val Pro Leu Ala Thr Lys Thr Ile Arg
               1               5                 10

AAA TTA TCA AAT CGA AAA TAT GAA ATA AAG ATT TAT TTA AAA GAT GAA                 3163
Lys Leu Ser Asn Arg Lys Tyr Glu Ile Lys Ile Tyr Leu Lys Asp Glu
        15              20              25

AAT ACT TGT TTC GAA CGT GTA GTA GAT ATG GTA GTT CCA TTA TAT GAT                 3211
Asn Thr Cys Phe Glu Arg Val Val Asp Met Val Val Pro Leu Tyr Asp
```

|  |  |  |  |  |  |  |  |  |  |  |  |  |  |  |  |
|---|---|---|---|---|---|---|---|---|---|---|---|---|---|---|---|
|  |  |  | 30 |  |  |  |  | 35 |  |  |  |  | 40 |  |  |
| GTG | TGT | AAT | GAA | ACT | TCT | GGT | GTT | ACT | TTA | GAA | TCA | TGT | AGT | CCA | AAT | 3259 |
| Val | Cys | Asn | Glu | Thr | Ser | Gly | Val | Thr | Leu | Glu | Ser | Cys | Ser | Pro | Asn |
| 45 |  |  |  |  | 50 |  |  |  |  | 55 |  |  |  |  | 60 |
| ATA | GAA | GTA | ATT | GAA | TTA | GAC | AAT | ACT | CAT | GTT | AGA | ATC | AAA | GTT | CAC | 3307 |
| Ile | Glu | Val | Ile | Glu | Leu | Asp | Asn | Thr | His | Val | Arg | Ile | Lys | Val | His |
|  |  |  |  | 65 |  |  |  |  | 70 |  |  |  |  | 75 |  |
| GGC | GAT | ACA | TTA | AAA | GAA | ATG | TGT | TTT | GAA | TTA | TTG | TTC | CCG | TGT | AAT | 3355 |
| Gly | Asp | Thr | Leu | Lys | Glu | Met | Cys | Phe | Glu | Leu | Leu | Phe | Pro | Cys | Asn |
|  |  |  | 80 |  |  |  |  | 85 |  |  |  |  | 90 |  |  |
| GTA | AAC | GAA | GCC | CAA | GTA | TGG | AAA | TAT | GTA | AGT | CGA | TTA | TTG | CTA | GAT | 3403 |
| Val | Asn | Glu | Ala | Gln | Val | Trp | Lys | Tyr | Val | Ser | Arg | Leu | Leu | Leu | Asp |
|  |  | 95 |  |  |  |  | 100 |  |  |  |  | 105 |  |  |  |
| AAT | GTA | TCA | CAT | AAT | GAC | GTA | AAA | TAT | AAA | TTA | GCT | AAT | TTT | AGA | CTG | 3451 |
| Asn | Val | Ser | His | Asn | Asp | Val | Lys | Tyr | Lys | Leu | Ala | Asn | Phe | Arg | Leu |
| 110 |  |  |  |  | 115 |  |  |  |  | 120 |  |  |  |  |  |
| ACT | CTT | AAT | GGA | AAA | CAT | TTA | AAA | TTA | AAA | GAA | ATC | GAT | CAA | CCG | CTA | 3499 |
| Thr | Leu | Asn | Gly | Lys | His | Leu | Lys | Leu | Lys | Glu | Ile | Asp | Gln | Pro | Leu |
| 125 |  |  |  |  | 130 |  |  |  |  | 135 |  |  |  |  | 140 |
| TTT | ATT | TAT | TTT | GTC | GAT | GAT | TTG | GGA | AAT | TAT | GGA | TTA | ATT | ACT | AAG | 3547 |
| Phe | Ile | Tyr | Phe | Val | Asp | Asp | Leu | Gly | Asn | Tyr | Gly | Leu | Ile | Thr | Lys |
|  |  |  |  | 145 |  |  |  |  | 150 |  |  |  |  | 155 |  |
| GAA | AAT | ATT | CAA | AAT | AAT | AAT | TTA | CAA | GTT | AAC | AAA | GAT | GCA | TCA | TTT | 3595 |
| Glu | Asn | Ile | Gln | Asn | Asn | Asn | Leu | Gln | Val | Asn | Lys | Asp | Ala | Ser | Phe |
|  |  |  | 160 |  |  |  |  | 165 |  |  |  |  | 170 |  |  |
| ATT | ACT | ATA | TTT | CCA | CAA | TAT | GCG | TAT | ATT | TGT | TTA | GGT | AGA | AAA | GTA | 3643 |
| Ile | Thr | Ile | Phe | Pro | Gln | Tyr | Ala | Tyr | Ile | Cys | Leu | Gly | Arg | Lys | Val |
|  |  | 175 |  |  |  |  | 180 |  |  |  |  | 185 |  |  |  |
| TAT | TTA | AAT | GAA | AAA | GTA | ACT | TTT | GAT | GTA | ACT | ACA | GAT | GCA | ACT | AAT | 3691 |
| Tyr | Leu | Asn | Glu | Lys | Val | Thr | Phe | Asp | Val | Thr | Thr | Asp | Ala | Thr | Asn |
|  | 190 |  |  |  |  | 195 |  |  |  |  | 200 |  |  |  |  |
| ATT | ACT | TTA | GAT | TTT | AAT | AAA | TCT | GTT | AAT | ATC | GCA | GTA | TCA | TTC | CTT | 3739 |
| Ile | Thr | Leu | Asp | Phe | Asn | Lys | Ser | Val | Asn | Ile | Ala | Val | Ser | Phe | Leu |
| 205 |  |  |  |  | 210 |  |  |  |  | 215 |  |  |  |  | 220 |
| GAT | ATA | TAT | TAC | GAA | GTT | AAT | AAT | AAT | GAA | CAA | AAA | GAT | TTA | TTA | AAA | 3787 |
| Asp | Ile | Tyr | Tyr | Glu | Val | Asn | Asn | Asn | Glu | Gln | Lys | Asp | Leu | Leu | Lys |
|  |  |  |  | 225 |  |  |  |  | 230 |  |  |  |  | 235 |  |
| GAT | TTA | CTT | AAG | AGA | TAC | GGT | GAA | TTT | GAA | GTC | TAT | AAC | GCA | GAT | ACT | 3835 |
| Asp | Leu | Leu | Lys | Arg | Tyr | Gly | Glu | Phe | Glu | Val | Tyr | Asn | Ala | Asp | Thr |
|  |  |  | 240 |  |  |  |  | 245 |  |  |  |  | 250 |  |  |
| GGA | TTA | ATT | TAT | GCT | AAA | AAT | CTA | AGT | ATT | AAA | AAT | TAT | GAT | ACT | GTG | 3883 |
| Gly | Leu | Ile | Tyr | Ala | Lys | Asn | Leu | Ser | Ile | Lys | Asn | Tyr | Asp | Thr | Val |
|  |  | 255 |  |  |  |  | 260 |  |  |  |  | 265 |  |  |  |
| ATT | CAA | GTA | GAA | AGG | TTG | CCA | GTT | AAT | TTG | AAA | GTT | AGA | GCA | TAT | ACT | 3931 |
| Ile | Gln | Val | Glu | Arg | Leu | Pro | Val | Asn | Leu | Lys | Val | Arg | Ala | Tyr | Thr |
|  | 270 |  |  |  |  | 275 |  |  |  |  | 280 |  |  |  |  |
| AAG | GAT | GAA | AAT | GGT | CGC | AAT | CTA | TGT | TTG | ATG | AAA | ATA | ACA | TCT | AGT | 3979 |
| Lys | Asp | Glu | Asn | Gly | Arg | Asn | Leu | Cys | Leu | Met | Lys | Ile | Thr | Ser | Ser |
| 285 |  |  |  |  | 290 |  |  |  |  | 295 |  |  |  |  | 300 |
| ACA | GAA | GTA | GAC | CCC | GAG | TAT | GTA | ACT | AGT | AAT | AAT | GCT | TTA | TTG | GGT | 4027 |
| Thr | Glu | Val | Asp | Pro | Glu | Tyr | Val | Thr | Ser | Asn | Asn | Ala | Leu | Leu | Gly |
|  |  |  |  | 305 |  |  |  |  | 310 |  |  |  |  | 315 |  |
| ACG | CTC | AGA | GTA | TAT | AAA | AAG | TTT | GAT | AAA | TCT | CAT | TTA | AAA | ATT | GTA | 4075 |
| Thr | Leu | Arg | Val | Tyr | Lys | Lys | Phe | Asp | Lys | Ser | His | Leu | Lys | Ile | Val |
|  |  |  | 320 |  |  |  |  | 325 |  |  |  |  | 330 |  |  |
| ATG | CAT | AAC | AGA | GGA | AGT | GGT | AAT | GTA | TTT | CCA | TTA | AGA | TCA | TTA | TAT | 4123 |
| Met | His | Asn | Arg | Gly | Ser | Gly | Asn | Val | Phe | Pro | Leu | Arg | Ser | Leu | Tyr |
|  |  | 335 |  |  |  |  | 340 |  |  |  |  | 345 |  |  |  |
| CTG | GAA | TTG | TCT | AAT | GTA | AAA | GGA | TAT | CCA | GTT | AAA | GCA | TCT | GAT | ACT | 4171 |
| Leu | Glu | Leu | Ser | Asn | Val | Lys | Gly | Tyr | Pro | Val | Lys | Ala | Ser | Asp | Thr |

-continued

|     |     |     | 350 |     |     |     |     | 355 |     |     |     |     | 360 |     |     |     |
|-----|-----|-----|-----|-----|-----|-----|-----|-----|-----|-----|-----|-----|-----|-----|-----|-----|

```
TCG AGA TTA GAT GTT GGT ATT TAC AAA TTA AAT AAA ATT TAT GTA GAT          4219
Ser Arg Leu Asp Val Gly Ile Tyr Lys Leu Asn Lys Ile Tyr Val Asp
365             370             375             380

AAC GAC GAA AAT AAA ATT ATA TTG GAA GAA ATT GAA GCA GAA TAT AGA          4267
Asn Asp Glu Asn Lys Ile Ile Leu Glu Glu Ile Glu Ala Glu Tyr Arg
                    385             390             395

TGC GGA AGA CAA GTA TTC CAC GAA CGT GTA AAA CTT AAT AAA CAC CAA          4315
Cys Gly Arg Gln Val Phe His Glu Arg Val Lys Leu Asn Lys His Gln
                400             405             410

TGT AAA TAT ACT CCC AAA TGT CCA TTC CAA TTT GTT GTA AAC AGC CCA          4363
Cys Lys Tyr Thr Pro Lys Cys Pro Phe Gln Phe Val Val Asn Ser Pro
            415             420             425

GAT ACT ACG ATT CAC TTA TAT GGT ATT TCT AAT GTT TGT TTA AAA CCT          4411
Asp Thr Thr Ile His Leu Tyr Gly Ile Ser Asn Val Cys Leu Lys Pro
        430             435             440

AAA GTA CCC AAA AAT TTA AGA CTT TGG GGA TGG ATT TTA GAT TGC GAT          4459
Lys Val Pro Lys Asn Leu Arg Leu Trp Gly Trp Ile Leu Asp Cys Asp
445             450             455             460

ACT TCT AGA TTT ATT AAA CAT ATG GCT GAT GGA TCT GAT GAT TTA GAT          4507
Thr Ser Arg Phe Ile Lys His Met Ala Asp Gly Ser Asp Asp Leu Asp
                465             470             475

CTT GAC GTT AGG CTT AAT AGA AAT GAT ATA TGT TTA AAA CAA GCC ATA          4555
Leu Asp Val Arg Leu Asn Arg Asn Asp Ile Cys Leu Lys Gln Ala Ile
                480             485             490

AAA CAA CAT TAT ACT AAT GTA ATT ATA TTA GAG TAC GCA AAT ACA TAT          4603
Lys Gln His Tyr Thr Asn Val Ile Ile Leu Glu Tyr Ala Asn Thr Tyr
            495             500             505

CCA AAT TGC ACA TTA TCA TTG GGT AAT AAT AGA TTT AAT AAT GTA TTT          4651
Pro Asn Cys Thr Leu Ser Leu Gly Asn Asn Arg Phe Asn Asn Val Phe
510             515             520

GAT ATG AAT GAT AAC AAA ACT ATA TCT GAG TAT ACT AAC TTT ACA AAA          4699
Asp Met Asn Asp Asn Lys Thr Ile Ser Glu Tyr Thr Asn Phe Thr Lys
525             530             535             540

AGT AGA CAA GAC CTT AAT AAC ATG TCA TGT ATA TTA GGA ATA AAC ATA          4747
Ser Arg Gln Asp Leu Asn Asn Met Ser Cys Ile Leu Gly Ile Asn Ile
                545             550             555

GGT AAT TCC GTA AAT ATT AGT AGT TTG CCT GGT TGG GTA ACA CCT CAC          4795
Gly Asn Ser Val Asn Ile Ser Ser Leu Pro Gly Trp Val Thr Pro His
                560             565             570

GAA GCT AAA ATT CTA AGA TCT GGT TGT GCT AGA GTT AGA GAA TTT TGT          4843
Glu Ala Lys Ile Leu Arg Ser Gly Cys Ala Arg Val Arg Glu Phe Cys
            575             580             585

AAA TCA TTC TGT GAT CTT TCT AAT AAG AGA TTC TAT GCT ATG GCT AGA          4891
Lys Ser Phe Cys Asp Leu Ser Asn Lys Arg Phe Tyr Ala Met Ala Arg
590             595             600

GAT CTC GTA AGT TTA CTA TTT ATG TGT AAC TAT GTT AAT ATT GAA ATT          4939
Asp Leu Val Ser Leu Leu Phe Met Cys Asn Tyr Val Asn Ile Glu Ile
605             610             615             620

AAC GAA GCA GTA TGC GAA TAT CCT GGA TAT GTC ATA TTA TTC GCA AGA          4987
Asn Glu Ala Val Cys Glu Tyr Pro Gly Tyr Val Ile Leu Phe Ala Arg
                625             630             635

GCT ATT AAA GTA ATT AAT GAT TTA TTA TTA ATT AAC GGA GTA GAT AAT          5035
Ala Ile Lys Val Ile Asn Asp Leu Leu Leu Ile Asn Gly Val Asp Asn
            640             645             650

CTA GCA GGA TAT TCA ATT TCC TTA CCT ATA CAT TAT GGA TCT ACT GAA          5083
Leu Ala Gly Tyr Ser Ile Ser Leu Pro Ile His Tyr Gly Ser Thr Glu
        655             660             665

AAG ACT CTA CCA AAT GAA AAG TAT GGT GGT GTT GAT AAG AAA TTT AAA          5131
Lys Thr Leu Pro Asn Glu Lys Tyr Gly Gly Val Asp Lys Lys Phe Lys
```

|  |  |  |  |  |  |  |  |  |  |  |  |  |  |  |  |  |
|---|---|---|---|---|---|---|---|---|---|---|---|---|---|---|---|---|
| | 670 | | | | | 675 | | | | | | 680 | | | | |
| TAT | CTA | TTC | TTA | AAG | AAT | AAA | CTA | AAA | GAT | TTA | ATG | CGT | GAT | GCT | GAT | 5179 |
| Tyr | Leu | Phe | Leu | Lys | Asn | Lys | Leu | Lys | Asp | Leu | Met | Arg | Asp | Ala | Asp | |
| 685 | | | | | 690 | | | | | 695 | | | | | 700 | |
| TTT | GTC | CAA | CCT | CCA | TTA | TAT | ATT | TCT | ACT | TAC | TTT | AGA | ACT | TTA | TTG | 5227 |
| Phe | Val | Gln | Pro | Pro | Leu | Tyr | Ile | Ser | Thr | Tyr | Phe | Arg | Thr | Leu | Leu | |
| | | | | | 705 | | | | | 710 | | | | | 715 | |
| GAT | GCT | CCA | CCA | ACT | GAT | AAT | TAT | GAA | AAA | TAT | TTG | GTT | GAT | TCG | TCC | 5275 |
| Asp | Ala | Pro | Pro | Thr | Asp | Asn | Tyr | Glu | Lys | Tyr | Leu | Val | Asp | Ser | Ser | |
| | | | | 720 | | | | | 725 | | | | | 730 | | |
| GTA | CAA | TCA | CAA | GAT | GTT | CTA | CAG | GGT | CTG | TTG | AAT | ACA | TGT | AAT | ACT | 5323 |
| Val | Gln | Ser | Gln | Asp | Val | Leu | Gln | Gly | Leu | Leu | Asn | Thr | Cys | Asn | Thr | |
| | | | 735 | | | | | 740 | | | | | 745 | | | |
| ATT | GAT | ACT | AAT | GCT | AGA | GTT | GCA | TCA | AGT | GTT | ATT | GGA | TAT | GTT | TAT | 5371 |
| Ile | Asp | Thr | Asn | Ala | Arg | Val | Ala | Ser | Ser | Val | Ile | Gly | Tyr | Val | Tyr | |
| | | | 750 | | | | | 755 | | | | | 760 | | | |
| GAA | CCA | TGC | GGA | ACA | TCA | GAA | CAT | AAA | ATT | GGT | TCA | GAA | GCA | TTG | TGT | 5419 |
| Glu | Pro | Cys | Gly | Thr | Ser | Glu | His | Lys | Ile | Gly | Ser | Glu | Ala | Leu | Cys | |
| 765 | | | | | 770 | | | | | 775 | | | | | 780 | |
| AAA | ATG | GCT | AAA | GAA | GCA | TCT | AGA | TTA | GGA | AAT | CTA | GGT | TTA | GTA | AAT | 5467 |
| Lys | Met | Ala | Lys | Glu | Ala | Ser | Arg | Leu | Gly | Asn | Leu | Gly | Leu | Val | Asn | |
| | | | | 785 | | | | | 790 | | | | | 795 | | |
| CGT | ATT | AAT | GAA | AGT | AAT | TAC | AAC | AAA | TGT | AAT | AAA | TAT | GGT | TAT | AGA | 5515 |
| Arg | Ile | Asn | Glu | Ser | Asn | Tyr | Asn | Lys | Cys | Asn | Lys | Tyr | Gly | Tyr | Arg | |
| | | | 800 | | | | | 805 | | | | | 810 | | | |
| GGA | GTA | TAC | GAA | AAT | AAC | AAA | CTA | AAA | ACA | AAA | TAT | TAT | AGA | GAA | ATA | 5563 |
| Gly | Val | Tyr | Glu | Asn | Asn | Lys | Leu | Lys | Thr | Lys | Tyr | Tyr | Arg | Glu | Ile | |
| | | | 815 | | | | | 820 | | | | | 825 | | | |
| TTT | GAT | TGT | AAT | CCT | AAT | AAT | AAT | AAT | GAA | TTA | ATA | TCC | AGA | TAT | GGA | 5611 |
| Phe | Asp | Cys | Asn | Pro | Asn | Asn | Asn | Asn | Glu | Leu | Ile | Ser | Arg | Tyr | Gly | |
| | | 830 | | | | | 835 | | | | | 840 | | | | |
| TAT | AGA | ATA | ATG | GAT | TTA | CAT | AAA | ATT | GGA | GAA | ATT | TTT | GCA | AAT | TAC | 5659 |
| Tyr | Arg | Ile | Met | Asp | Leu | His | Lys | Ile | Gly | Glu | Ile | Phe | Ala | Asn | Tyr | |
| 845 | | | | | 850 | | | | | 855 | | | | | 860 | |
| GAT | GAA | AGT | GAA | TCT | CCT | TGC | GAA | CGA | AGA | TGT | CAT | TAC | TTG | GAA | GAT | 5707 |
| Asp | Glu | Ser | Glu | Ser | Pro | Cys | Glu | Arg | Arg | Cys | His | Tyr | Leu | Glu | Asp | |
| | | | | 865 | | | | | 870 | | | | | 875 | | |
| AGA | GGT | CTT | TTA | TAT | GGT | CCT | GAA | TAT | GTA | CAT | CAC | AGA | TAT | CAA | GAA | 5755 |
| Arg | Gly | Leu | Leu | Tyr | Gly | Pro | Glu | Tyr | Val | His | His | Arg | Tyr | Gln | Glu | |
| | | | 880 | | | | | 885 | | | | | 890 | | | |
| TCA | TGT | ACG | CCT | AAT | ACG | TTT | GGA | AAT | AAC | ACA | AAT | TGT | GTA | ACA | AGA | 5803 |
| Ser | Cys | Thr | Pro | Asn | Thr | Phe | Gly | Asn | Asn | Thr | Asn | Cys | Val | Thr | Arg | |
| | | 895 | | | | | 900 | | | | | 905 | | | | |
| AAT | GGT | GAA | CAA | CAC | GTA | TAC | GAA | AAT | AGT | TGT | GGA | GAT | AAT | GCA | ACA | 5851 |
| Asn | Gly | Glu | Gln | His | Val | Tyr | Glu | Asn | Ser | Cys | Gly | Asp | Asn | Ala | Thr | |
| | 910 | | | | | 915 | | | | | 920 | | | | | |
| TGT | GGA | AGA | AGA | ACA | GGA | TAT | GGA | AGA | AGA | AGT | AGG | GAT | GAA | TGG | AAT | 5899 |
| Cys | Gly | Arg | Arg | Thr | Gly | Tyr | Gly | Arg | Arg | Ser | Arg | Asp | Glu | Trp | Asn | |
| 925 | | | | | 930 | | | | | 935 | | | | | 940 | |
| GAC | TAT | AGA | AAA | CCC | CAC | GTT | TAT | GAC | AAT | TGT | GCC | GAT | GCA | AAT | AGT | 5947 |
| Asp | Tyr | Arg | Lys | Pro | His | Val | Tyr | Asp | Asn | Cys | Ala | Asp | Ala | Asn | Ser | |
| | | | | 945 | | | | | 950 | | | | | 955 | | |
| TCA | TCT | TCA | GAT | AGC | TGT | TCA | GAC | AGT | AGT | AGT | AGT | GAA | TCT | GAA | | 5995 |
| Ser | Ser | Ser | Asp | Ser | Cys | Ser | Asp | Ser | Ser | Ser | Ser | Glu | Ser | Glu | | |
| | | | 960 | | | | | 965 | | | | | 970 | | | |
| TCT | GAT | TCA | GAT | GGA | TGT | TGC | GAC | ACA | GAT | GCT | AGT | TTA | GAT | TCT | GAT | 6043 |
| Ser | Asp | Ser | Asp | Gly | Cys | Cys | Asp | Thr | Asp | Ala | Ser | Leu | Asp | Ser | Asp | |
| | | 975 | | | | | 980 | | | | | 985 | | | | |
| ATT | GAA | AAT | TGT | TAT | CAA | AAT | CCA | TCA | AAA | TGT | GAT | GCA | GGA | TGC | TAAATGAA | 6098 |
| Ile | Glu | Asn | Cys | Tyr | Gln | Asn | Pro | Ser | Lys | Cys | Asp | Ala | Gly | Cys | | |

```
       990              995              1000
TTAATATTAT ATAATATTAA CTTACAAGTT ATAAAAATCA TTAAAATGAT TTTTTAAAAT  6158

GATATTATCG ATAGTTGTGA TAATGTGCTC TTTTATTTTA TTAATTGCGA TGATTATAAT  6218

ATTATCTTTT AGATATATTT AATATTAATT ATAAATCGAC TGACAATAAT ATTTATTCCT  6278

ATTCATAATA ATCATCTGCT ATATATATTA ATGTATCATT CTCTATTATA AATATAGGTA  6338

TATTGTCTTT ATCAATCATT AATTTTGCTA CAGCTGTATT ATCTTTATAT ACTATATTTG  6398

TGTCTTTGTT TAATAAACCT TTAATATAG TGGCTCTATC ATAATCTTTA CAATATGATA   6458

TGGGATATAA TTTTATATTA ATAATAACAT TAGATACGTT CATTTCTTTC ATTCTAGTTT  6518

TACGTATTGT GTCAAAAATT ATTTCATTTT CTGCTGGTTC TATATATTTA TATGTGTTAT  6578

GAATAGATTC GATAGATGAT GATTTTAATA AATCAAATAT AACATTATT TTACCTTGTT   6638

TATCTTTTAT AATATCTAAT ATTTCTTTAT CTACAGATTT TCTGTTGTTG GTATATGATA  6698

TTAAAAAATG AACGTTAACA TATCTATATT CTTGTGGTAA ATCTTTATGA GAATTTAATC  6758

TTATAGATCT                                                        6768
```

( 2 ) INFORMATION FOR SEQ ID NO:2:

( i ) SEQUENCE CHARACTERISTICS:
        ( A ) LENGTH: 464 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Asn Asn Lys Ile Arg Arg Phe Pro Asn Lys Asn Leu Lys Met Pro
 1               5                  10                  15

Glu Ser Gly Ile Asn Phe Met Ser Met Leu Phe Phe Ser Lys Ile Asp
                20                  25                  30

Asn Met Val Tyr Phe Ile Asn Pro Ile Lys Tyr Asn Thr Asn Ala Asn
            35                  40                  45

Ile Ala Ile Leu Glu Lys Ile Asp Asp Asp Glu Thr Arg Gly Lys
        50                  55                  60

Val Thr Phe Ile Pro Ile Lys Tyr Leu Glu Ile Leu Tyr Asn Glu Leu
65                  70                  75                  80

Val Leu Asp Pro Asn His Ile Asn Asn Ile Asn Phe Glu Asn Asn Ile
                85                  90                  95

Lys Arg Lys Phe Phe Leu Phe Trp Thr Ile Lys Lys Tyr Leu Gln Asp
            100                 105                 110

Lys Asn Ile Asn Ile Asn Thr Phe Ile Thr Ser Lys Lys Tyr Lys Gly
        115                 120                 125

Ile Pro Leu Val Tyr Met Arg Lys Ser Phe Leu Lys Ser Glu Leu Ser
130                 135                 140

Lys Thr Arg Asp Phe Ser Thr Phe Ala Thr Ile Tyr Asp Asp Leu Asp
145                 150                 155                 160

Ala Gln Ile Gly Ile Pro Pro Leu Gly Phe Asn Pro Lys Pro Lys Ala
                165                 170                 175

Tyr Pro Arg Lys His Asp Lys Ser Thr Trp Leu Ser Ser Gly Asp Ile
            180                 185                 190

Tyr Asn Cys Ile Tyr Pro Leu Thr Met Ile Asn Thr Asp Tyr Asp Tyr
        195                 200                 205

Phe His Leu Ile Leu Phe Glu Lys Thr Asp Lys Asn Ile Ala Thr Val
210                 215                 220
```

| | | | | | | | | | | | | | | |
|---|---|---|---|---|---|---|---|---|---|---|---|---|---|---|
| Ala 225 | Ser | Ser | Met | Arg 230 | Cys | Tyr | Lys | Leu | Glu 235 | Asp | Arg | Val | Lys | Phe 240 |
| Leu | Met | Asn | Asp | Lys 245 | Lys | Arg | Phe | Phe | Met 250 | Phe | Pro | Ile | Ile | Tyr 255 | Asn |
| Asp | His | Phe | Thr 260 | Cys | Cys | Val | Ile | Asp 265 | Lys | His | Phe | Asp | Lys 270 | Asp | Lys |
| Lys | Ala | Ala 275 | Tyr | Phe | Phe | Asn | Ser 280 | Ser | Gly | Tyr | Ile | Pro 285 | Glu | Leu | Ile |
| Lys | Gln 290 | Asn | Lys | Lys | Tyr | Met 295 | Phe | Ile | Glu | Ser | Asp 300 | Met | Thr | Ile | Lys |
| Ser 305 | His | Lys | His | Tyr | Asn 310 | Ser | Thr | Pro | Asn | Thr 315 | Asn | Tyr | Ala | Tyr | Leu 320 |
| Tyr | Ile | Asp | Val | Leu 325 | Ser | Glu | Tyr | Leu | Asn 330 | Asp | Ile | Phe | Lys | Asn 335 | Val |
| Asn | Tyr | Tyr | Phe 340 | Phe | Asn | Thr | Phe | Glu 345 | Leu | Gln | Tyr | Asp | Ser 350 | Pro | Asp |
| Cys | Gly | Met 355 | Phe | Asn | Ile | Ile | Phe 360 | Leu | Tyr | Tyr | Ile | Val 365 | Tyr | Phe | Asn |
| Ile | Lys 370 | Ser | Lys | Phe | Glu | Phe 375 | Lys | Lys | Leu | Tyr | Tyr 380 | Ser | Met | Ser | Phe |
| Ile 385 | Gly | Asp | Leu | Leu | Ala 390 | Ser | Ser | Tyr | Arg | Gly 395 | Ala | Leu | Phe | Ile | Ser 400 |
| Arg | Tyr | Asp | Ile | Asn 405 | Ser | Ile | Asp | Glu | Phe 410 | Lys | Asn | Thr | Leu | Glu 415 | Ile |
| Phe | Asn | Ile | Lys 420 | Asn | Lys | Lys | Phe | Met 425 | Glu | Leu | Ile | Asp | Met 430 | Tyr | Lys |
| Lys | Asn | Ser 435 | Asn | Arg | Ile | Met | Asn 440 | Val | Cys | Ser | Lys | Ile 445 | Lys | Asn | Asp |
| Tyr 450 | Asp | Ser | Tyr | Ile | Asp 455 | Asn | Glu | Lys | Asn | Ser 460 | Leu | Glu | Ser | Asn | Ile |

(2) INFORMATION FOR SEQ ID NO:3:

(i) SEQUENCE CHARACTERISTICS:
        (A) LENGTH: 225 amino acids
        (B) TYPE: amino acid
        (D) TOPOLOGY: linear (ii) MOLECULE TYPE: protein (xi) SEQUENCE DESCRIPTION: SEQ ID NO:3:

| | | | | | | | | | | | | | | |
|---|---|---|---|---|---|---|---|---|---|---|---|---|---|---|
| Met 1 | Phe | Leu | Val | Tyr 5 | Phe | Asn | Thr | Phe | Leu 10 | Ile | Ile | Leu | Leu 15 | Phe |
| Gly | Ile | Ile | Gly 20 | Ile | Tyr | Ile | Leu | Thr 25 | Phe | Val | Phe | Asn | Ile 30 | Asp | Phe |
| Leu | Ile | Asn 35 | Asn | Asn | Lys | Ile | Tyr 40 | Ile | Leu | Ser | Tyr | Asn 45 | Ala | Thr | Asn |
| Ile | Asn 50 | Asn | Ile | Asn | Asn | Leu 55 | Asn | Leu | Tyr | Asp | Tyr 60 | Ser | Asp | Ile | Ile |
| Phe 65 | Leu | Thr | Asn | Phe | Asn 70 | Ile | Asn | Asn | Asn | Leu 75 | Leu | Val | Thr | Gln | Ala 80 |
| Asn | Asn | Leu | Gln | Asp 85 | Ile | Pro | Ile | Phe | Asn 90 | Val | Asn | Asn | Ile | Ile 95 | Ser |
| Asn | Gln | Tyr | Asn 100 | Phe | Tyr | Ser | Ala | Ser 105 | Ser | Asn | Asn | Val | Asn 110 | Ile | Leu |
| Leu | Gly | Leu 115 | Arg | Lys | Thr | Leu | Asn 120 | Ile | Asn | Arg | Asn | Pro 125 | Phe | Leu | Leu |

```
Phe  Arg  Asn  Thr  Ser  Leu  Ala  Ile  Val  Phe  Asn  Asn  Glu  Thr  Phe
     130                 135                      140

His  Cys  Tyr  Ile  Ser  Ser  Asn  Gln  Asn  Ser  Asp  Val  Leu  Asp  Ile  Val
145                      150                      155                           160

Ser  His  Ile  Glu  Phe  Met  Lys  Ser  Arg  Tyr  Asn  Lys  Tyr  Val  Ile  Ile
                    165                 170                      175

Gly  Glu  Ile  Pro  Val  Asn  Asn  Asn  Ile  Ser  Ile  Asn  Asn  Ile  Leu  Asn
               180                      185                      190

Asn  Phe  Ala  Ile  Ile  Thr  Asn  Val  Arg  Leu  Ile  Asp  Lys  Tyr  Asn  Ser
          195                      200                 205

Ile  Ile  Ser  Phe  Leu  Asn  Ile  Asn  Val  Gly  Thr  Leu  Phe  Val  Ile  Asn
     210                      215                      220

Pro

225
```

( 2 ) INFORMATION FOR SEQ ID NO:4:

( i ) SEQUENCE CHARACTERISTICS:
( A ) LENGTH: 78 amino acids
( B ) TYPE: amino acid
( D ) TOPOLOGY: linear ( i i ) MOLECULE TYPE: protein ( x i ) SEQUENCE DESCRIPTION: SEQ ID NO:4:

```
Met  Ser  Ser  Ser  Lys  Lys  Asn  Asn  Leu  Gly  Tyr  Phe  Asn  Asn  Leu  Lys
1                   5                        10                      15

Thr  Glu  Glu  Val  Ser  Gln  Ser  Gln  Val  Phe  Lys  Asp  Asn  Tyr  Arg  Pro
               20                  25                      30

Gly  Tyr  Tyr  Gly  Leu  Asp  Thr  Asn  Ala  Ala  Asn  Pro  Ala  Asp  Val  Tyr
          35                  40                      45

Asn  Thr  Glu  Ser  Asn  Lys  Pro  Ser  Thr  Val  Asp  Val  Trp  Gly  Asp  Lys
     50                  55                      60

Arg  Leu  Glu  Gly  Lys  Ile  Ile  Pro  Lys  Ser  Lys  Lys  Lys  Lys
65                       70                  75
```

( 2 ) INFORMATION FOR SEQ ID NO:5:

( i ) SEQUENCE CHARACTERISTICS:
( A ) LENGTH: 161 amino acids
( B ) TYPE: amino acid
( D ) TOPOLOGY: linear ( i i ) MOLECULE TYPE: protein ( x i ) SEQUENCE DESCRIPTION: SEQ ID NO:5:

```
Met  Ser  Ile  Phe  Ile  Tyr  Tyr  Ile  Phe  Asn  Asn  Arg  Phe  Tyr  Ile  Tyr
1                   5                        10                      15

Lys  Arg  Met  Asn  Thr  Val  Gln  Ile  Leu  Val  Val  Ile  Leu  Ile  Thr  Thr
               20                  25                      30

Ala  Leu  Ser  Phe  Leu  Val  Phe  Gln  Leu  Trp  Tyr  Tyr  Ala  Glu  Asn  Tyr
          35                  40                      45

Glu  Tyr  Ile  Leu  Arg  Tyr  Asn  Asp  Thr  Tyr  Ser  Asn  Leu  Gln  Phe  Ala
     50                  55                      60

Arg  Ser  Ala  Asn  Ile  Asn  Phe  Asp  Asp  Leu  Thr  Val  Phe  Asp  Pro  Asn
65                       70                  75                           80

Asp  Asn  Val  Phe  Asn  Val  Glu  Glu  Lys  Trp  Arg  Cys  Ala  Ser  Thr  Asn
                    85                      90                      95
```

| Asn | Asn | Ile | Phe | Tyr | Ala | Val | Ser | Thr | Phe | Gly | Phe | Leu | Ser | Thr | Glu |
|---|---|---|---|---|---|---|---|---|---|---|---|---|---|---|---|
| | | 100 | | | | | 105 | | | | | 110 | | | |

| Ser | Thr | Gly | Ile | Asn | Leu | Thr | Tyr | Thr | Asn | Ser | Arg | Asp | Cys | Ile | Ile |
|---|---|---|---|---|---|---|---|---|---|---|---|---|---|---|---|
| | | 115 | | | | | 120 | | | | | 125 | | | |

| Asp | Leu | Phe | Ser | Arg | Ile | Ile | Lys | Ile | Val | Tyr | Asp | Pro | Cys | Thr | Val |
|---|---|---|---|---|---|---|---|---|---|---|---|---|---|---|---|
| | 130 | | | | | 135 | | | | | 140 | | | | |

| Glu | Thr | Ser | Asn | Asp | Cys | Arg | Leu | Leu | Arg | Leu | Leu | Met | Ala | Asn | Thr |
|---|---|---|---|---|---|---|---|---|---|---|---|---|---|---|---|
| 145 | | | | | 150 | | | | | 155 | | | | | 160 |

Ser ( 2 ) INFORMATION FOR SEQ ID NO:6:

( i ) SEQUENCE CHARACTERISTICS:
        ( A ) LENGTH: 1003 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

| Met | Ser | Asn | Val | Pro | Leu | Ala | Thr | Lys | Thr | Ile | Arg | Lys | Leu | Ser | Asn |
|---|---|---|---|---|---|---|---|---|---|---|---|---|---|---|---|
| 1 | | | | 5 | | | | | 10 | | | | | 15 | |

| Arg | Lys | Tyr | Glu | Ile | Lys | Ile | Tyr | Leu | Lys | Asp | Glu | Asn | Thr | Cys | Phe |
|---|---|---|---|---|---|---|---|---|---|---|---|---|---|---|---|
| | | | 20 | | | | | 25 | | | | | 30 | | |

| Glu | Arg | Val | Val | Asp | Met | Val | Val | Pro | Leu | Tyr | Asp | Val | Cys | Asn | Glu |
|---|---|---|---|---|---|---|---|---|---|---|---|---|---|---|---|
| | | | 35 | | | | 40 | | | | | 45 | | | |

| Thr | Ser | Gly | Val | Thr | Leu | Glu | Ser | Cys | Ser | Pro | Asn | Ile | Glu | Val | Ile |
|---|---|---|---|---|---|---|---|---|---|---|---|---|---|---|---|
| | 50 | | | | | 55 | | | | | 60 | | | | |

| Glu | Leu | Asp | Asn | Thr | His | Val | Arg | Ile | Lys | Val | His | Gly | Asp | Thr | Leu |
|---|---|---|---|---|---|---|---|---|---|---|---|---|---|---|---|
| 65 | | | | | 70 | | | | | 75 | | | | | 80 |

| Lys | Glu | Met | Cys | Phe | Glu | Leu | Leu | Phe | Pro | Cys | Asn | Val | Asn | Glu | Ala |
|---|---|---|---|---|---|---|---|---|---|---|---|---|---|---|---|
| | | | | 85 | | | | | 90 | | | | | 95 | |

| Gln | Val | Trp | Lys | Tyr | Val | Ser | Arg | Leu | Leu | Leu | Asp | Asn | Val | Ser | His |
|---|---|---|---|---|---|---|---|---|---|---|---|---|---|---|---|
| | | | 100 | | | | | 105 | | | | | 110 | | |

| Asn | Asp | Val | Lys | Tyr | Lys | Leu | Ala | Asn | Phe | Arg | Leu | Thr | Leu | Asn | Gly |
|---|---|---|---|---|---|---|---|---|---|---|---|---|---|---|---|
| | | 115 | | | | | 120 | | | | | 125 | | | |

| Lys | His | Leu | Lys | Leu | Lys | Glu | Ile | Asp | Gln | Pro | Leu | Phe | Ile | Tyr | Phe |
|---|---|---|---|---|---|---|---|---|---|---|---|---|---|---|---|
| | 130 | | | | | 135 | | | | | 140 | | | | |

| Val | Asp | Asp | Leu | Gly | Asn | Tyr | Gly | Leu | Ile | Thr | Lys | Glu | Asn | Ile | Gln |
|---|---|---|---|---|---|---|---|---|---|---|---|---|---|---|---|
| 145 | | | | | 150 | | | | | 155 | | | | | 160 |

| Asn | Asn | Asn | Leu | Gln | Val | Asn | Lys | Asp | Ala | Ser | Phe | Ile | Thr | Ile | Phe |
|---|---|---|---|---|---|---|---|---|---|---|---|---|---|---|---|
| | | | | 165 | | | | | 170 | | | | | 175 | |

| Pro | Gln | Tyr | Ala | Tyr | Ile | Cys | Leu | Gly | Arg | Lys | Val | Tyr | Leu | Asn | Glu |
|---|---|---|---|---|---|---|---|---|---|---|---|---|---|---|---|
| | | | 180 | | | | | 185 | | | | | 190 | | |

| Lys | Val | Thr | Phe | Asp | Val | Thr | Thr | Asp | Ala | Thr | Asn | Ile | Thr | Leu | Asp |
|---|---|---|---|---|---|---|---|---|---|---|---|---|---|---|---|
| | | 195 | | | | | 200 | | | | | 205 | | | |

| Phe | Asn | Lys | Ser | Val | Asn | Ile | Ala | Val | Ser | Phe | Leu | Asp | Ile | Tyr | Tyr |
|---|---|---|---|---|---|---|---|---|---|---|---|---|---|---|---|
| | 210 | | | | | 215 | | | | | 220 | | | | |

| Glu | Val | Asn | Asn | Asn | Glu | Gln | Lys | Asp | Leu | Leu | Lys | Asp | Leu | Leu | Lys |
|---|---|---|---|---|---|---|---|---|---|---|---|---|---|---|---|
| 225 | | | | | 230 | | | | | 235 | | | | | 240 |

| Arg | Tyr | Gly | Glu | Phe | Glu | Val | Tyr | Asn | Ala | Asp | Thr | Gly | Leu | Ile | Tyr |
|---|---|---|---|---|---|---|---|---|---|---|---|---|---|---|---|
| | | | | 245 | | | | | 250 | | | | | 255 | |

| Ala | Lys | Asn | Leu | Ser | Ile | Lys | Asn | Tyr | Asp | Thr | Val | Ile | Gln | Val | Glu |
|---|---|---|---|---|---|---|---|---|---|---|---|---|---|---|---|
| | | | 260 | | | | | 265 | | | | | 270 | | |

| Arg | Leu | Pro | Val | Asn | Leu | Lys | Val | Arg | Ala | Tyr | Thr | Lys | Asp | Glu | Asn |
|---|---|---|---|---|---|---|---|---|---|---|---|---|---|---|---|
| | | 275 | | | | | 280 | | | | | 285 | | | |

```
Gly Arg Asn Leu Cys Leu Met Lys Ile Thr Ser Ser Thr Glu Val Asp
    290                 295                 300
Pro Glu Tyr Val Thr Ser Asn Asn Ala Leu Leu Gly Thr Leu Arg Val
305                 310                 315                 320
Tyr Lys Lys Phe Asp Lys Ser His Leu Lys Ile Val Met His Asn Arg
                325                 330                 335
Gly Ser Gly Asn Val Phe Pro Leu Arg Ser Leu Tyr Leu Glu Leu Ser
            340                 345                 350
Asn Val Lys Gly Tyr Pro Val Lys Ala Ser Asp Thr Ser Arg Leu Asp
        355                 360                 365
Val Gly Ile Tyr Lys Leu Asn Lys Ile Tyr Val Asp Asn Asp Glu Asn
    370                 375                 380
Lys Ile Ile Leu Glu Glu Ile Glu Ala Glu Tyr Arg Cys Gly Arg Gln
385                 390                 395                 400
Val Phe His Glu Arg Val Lys Leu Asn Lys His Gln Cys Lys Tyr Thr
                405                 410                 415
Pro Lys Cys Pro Phe Gln Phe Val Val Asn Ser Pro Asp Thr Thr Ile
            420                 425                 430
His Leu Tyr Gly Ile Ser Asn Val Cys Leu Lys Pro Lys Val Pro Lys
        435                 440                 445
Asn Leu Arg Leu Trp Gly Trp Ile Leu Asp Cys Asp Thr Ser Arg Phe
450                 455                 460
Ile Lys His Met Ala Asp Gly Ser Asp Asp Leu Asp Leu Asp Val Arg
465                 470                 475                 480
Leu Asn Arg Asn Asp Ile Cys Leu Lys Gln Ala Ile Lys Gln His Tyr
                485                 490                 495
Thr Asn Val Ile Ile Leu Glu Tyr Ala Asn Thr Tyr Pro Asn Cys Thr
            500                 505                 510
Leu Ser Leu Gly Asn Asn Arg Phe Asn Asn Val Phe Asp Met Asn Asp
        515                 520                 525
Asn Lys Thr Ile Ser Glu Tyr Thr Asn Phe Thr Lys Ser Arg Gln Asp
    530                 535                 540
Leu Asn Asn Met Ser Cys Ile Leu Gly Ile Asn Ile Gly Asn Ser Val
545                 550                 555                 560
Asn Ile Ser Ser Leu Pro Gly Trp Val Thr Pro His Glu Ala Lys Ile
                565                 570                 575
Leu Arg Ser Gly Cys Ala Arg Val Arg Glu Phe Cys Lys Ser Phe Cys
            580                 585                 590
Asp Leu Ser Asn Lys Arg Phe Tyr Ala Met Ala Arg Asp Leu Val Ser
        595                 600                 605
Leu Leu Phe Met Cys Asn Tyr Val Asn Ile Glu Ile Asn Glu Ala Val
    610                 615                 620
Cys Glu Tyr Pro Gly Tyr Val Ile Leu Phe Ala Arg Ala Ile Lys Val
625                 630                 635                 640
Ile Asn Asp Leu Leu Leu Ile Asn Gly Val Asp Asn Leu Ala Gly Tyr
                645                 650                 655
Ser Ile Ser Leu Pro Ile His Tyr Gly Ser Thr Glu Lys Thr Leu Pro
            660                 665                 670
Asn Glu Lys Tyr Gly Gly Val Asp Lys Lys Phe Lys Tyr Leu Phe Leu
        675                 680                 685
Lys Asn Lys Leu Lys Asp Leu Met Arg Asp Ala Asp Phe Val Gln Pro
    690                 695                 700
Pro Leu Tyr Ile Ser Thr Tyr Phe Arg Thr Leu Leu Asp Ala Pro Pro
705                 710                 715                 720
```

```
Thr  Asp  Asn  Tyr  Glu  Lys  Tyr  Leu  Val  Asp  Ser  Ser  Val  Gln  Ser  Gln
               725                730                          735

Asp  Val  Leu  Gln  Gly  Leu  Leu  Asn  Thr  Cys  Asn  Thr  Ile  Asp  Thr  Asn
               740                745                          750

Ala  Arg  Val  Ala  Ser  Ser  Val  Ile  Gly  Tyr  Val  Tyr  Glu  Pro  Cys  Gly
          755                     760                765

Thr  Ser  Glu  His  Lys  Ile  Gly  Ser  Glu  Ala  Leu  Cys  Lys  Met  Ala  Lys
     770                     775                     780

Glu  Ala  Ser  Arg  Leu  Gly  Asn  Leu  Gly  Leu  Val  Asn  Arg  Ile  Asn  Glu
785                      790                795                               800

Ser  Asn  Tyr  Asn  Lys  Cys  Asn  Lys  Tyr  Gly  Tyr  Arg  Gly  Val  Tyr  Glu
               805                     810                          815

Asn  Asn  Lys  Leu  Lys  Thr  Lys  Tyr  Tyr  Arg  Glu  Ile  Phe  Asp  Cys  Asn
               820                     825                          830

Pro  Asn  Asn  Asn  Asn  Glu  Leu  Ile  Ser  Arg  Tyr  Gly  Tyr  Arg  Ile  Met
          835                     840                     845

Asp  Leu  His  Lys  Ile  Gly  Glu  Ile  Phe  Ala  Asn  Tyr  Asp  Glu  Ser  Glu
     850                     855                     860

Ser  Pro  Cys  Glu  Arg  Arg  Cys  His  Tyr  Leu  Glu  Asp  Arg  Gly  Leu  Leu
865                      870                     875                          880

Tyr  Gly  Pro  Glu  Tyr  Val  His  His  Arg  Tyr  Gln  Glu  Ser  Cys  Thr  Pro
               885                     890                          895

Asn  Thr  Phe  Gly  Asn  Asn  Thr  Asn  Cys  Val  Thr  Arg  Asn  Gly  Glu  Gln
               900                     905                          910

His  Val  Tyr  Glu  Asn  Ser  Cys  Gly  Asp  Asn  Ala  Thr  Cys  Gly  Arg  Arg
          915                     920                     925

Thr  Gly  Tyr  Gly  Arg  Arg  Ser  Arg  Asp  Glu  Trp  Asn  Asp  Tyr  Arg  Lys
     930                     935                     940

Pro  His  Val  Tyr  Asp  Asn  Cys  Ala  Asp  Ala  Asn  Ser  Ser  Ser  Ser  Asp
945                      950                     955                          960

Ser  Cys  Ser  Asp  Ser  Ser  Ser  Ser  Glu  Ser  Glu  Ser  Asp  Ser  Ser  Asp
               965                     970                          975

Gly  Cys  Cys  Asp  Thr  Asp  Ala  Ser  Leu  Asp  Ser  Asp  Ile  Glu  Asn  Cys
               980                     985                          990

Tyr  Gln  Asn  Pro  Ser  Lys  Cys  Asp  Ala  Gly  Cys
               995                     1000
```

( 2 ) INFORMATION FOR SEQ ID NO:7:

( i ) SEQUENCE CHARACTERISTICS:
        ( A ) LENGTH: 163 amino acids
        ( B ) TYPE: amino acid
        ( D ) TOPOLOGY: linear ( i i ) MOLECULE TYPE: protein ( x i ) SEQUENCE DESCRIPTION: SEQ ID NO:7:

```
Arg  Ser  Ile  Arg  Leu  Asn  Ser  His  Lys  Asp  Leu  Pro  Gln  Glu  Tyr  Arg
1                    5                     10                          15

Tyr  Val  Asn  Val  His  Phe  Leu  Ile  Ser  Tyr  Thr  Asn  Asn  Arg  Lys  Ser
          20                     25                          30

Val  Asp  Lys  Glu  Ile  Leu  Asp  Ile  Ile  Lys  Asp  Lys  Gln  Gly  Lys  Ile
          35                     40                          45

Asn  Val  Ile  Phe  Asp  Leu  Leu  Lys  Ser  Ser  Ser  Ile  Glu  Ser  Ile  His
          50                     55                          60

Asn  Thr  Tyr  Lys  Tyr  Ile  Glu  Pro  Ala  Glu  Asn  Glu  Ile  Ile  Phe  Asp
```

```
                          65                          70                          75                           80
Thr   Ile   Arg   Lys   Thr   Arg   Met   Lys   Glu   Met   Asn   Val   Ser   Asn   Val   Ile
                         85                          90                                 95

Ile   Asn   Ile   Lys   Leu   Tyr   Pro   Ile   Ser   Tyr   Cys   Lys   Asp   Tyr   Asp   Arg
                  100                         105                         110

Ala   Thr   Ile   Leu   Lys   Gly   Leu   Leu   Asn   Lys   Asp   Thr   Asn   Ile   Val   Tyr
            115                         120                         125

Lys   Asp   Asn   Thr   Ala   Val   Ala   Lys   Leu   Met   Ile   Asp   Lys   Asp   Asn   Ile
      130                         135                         140

Pro   Ile   Phe   Ile   Ile   Glu   Asn   Asp   Thr   Leu   Ile   Tyr   Ile   Ala   Asp   Asp
145                           150                         155                         160

Tyr   Tyr   Glu
```

( 2 ) INFORMATION FOR SEQ ID NO:8:

( i ) SEQUENCE CHARACTERISTICS:
        ( A ) LENGTH: 1511 base pairs
        ( B ) TYPE: nucleic acid
        ( C ) STRANDEDNESS: double
        ( D ) TOPOLOGY: unknown ( i i ) MOLECULE TYPE: DNA (genomic)

( v i ) ORIGINAL SOURCE:
        ( A ) ORGANISM: Amsacta moorei entemopoxvirus ( i x ) FEATURE:
        ( A ) NAME/KEY: CDS
        ( B ) LOCATION: complement (18..218)

( i x ) FEATURE:
        ( A ) NAME/KEY: CDS
        ( B ) LOCATION: complement (234..782)

( i x ) FEATURE:
        ( A ) NAME/KEY: CDS
        ( B ) LOCATION: 852..1511

( x i ) SEQUENCE DESCRIPTION: SEQ ID NO:8:

```
GAATTCAAGT   TAAATATTTA   TAAACAACAA   TCATATTTTT   TTAAAGAATC   TAATAAATTT        60
TTTAACATTT   TATTATTATT   TGATAATTGT   TTATTTAATT   CGTTATTGAT   ATTAACAATA       120
TTATTTATCA   TTTTACCTAT   TTTTTTTTTT   CTATCTACTA   ACGAAATATC   AGATTTGCA        180
CCTTCAATAT   CAGAATAATA   ATTATCATTA   TTTTGCATTT   ATGAATAAAA   ATATTAATAT       240
GAATTATTAT   AACATAATCT   ACACACAGGA   ACATATAAAT   CTTGTCCACC   TATTTCAATT       300
ATTTGATTTT   TATTATGTTT   TTAATTGTA    AAAGAAGCAT   CTTATAACA    AAATTGACAT       360
ATAGCTTGTA   ATTTTTTTAT   TTTTCTACT    TTAGGAATTA   ATTTGATAT    AGAATTAAAT       420
ATATTTCTGT   TAAAGTCACA   ATTTAATCCA   GCAACAATAA   CTTTTTTTT    ATTATTAGCC       480
ATTTTATCAC   AAAATTGTTC   TAAATCATTT   TCTTCAAAAA   ATTGACACTC   ATCTATGCCA       540
ATAATATCAT   AATTATCTAC   GATATTGATT   TCATTAATTA   AATTATTGT    TTAATGTAT        600
AAATATTCTT   TATTTAATAT   ATTTCCGTCA   TGATTATTA    TATTTTATT    TATAAATCTA       660
TTATCTATAT   TATGAGTTAT   AATTACACAT   TTTGATTAG    ATAAATATA    TCTATTAATT       720
TTTCGCATCA   ATTCTGTTGT   TTTGCCAGAA   AACATAGGAC   CAATTATTAA   TTCTATCGAC       780
ATTTTTTTT    ATTATTGAT    ATATTTTTC    AAAAAAAAT    TAATCAATGA   AAAAAAATA        840
AAATTATCAA    A  ATG GAT  TTA CTA AAT  TCT GAT ATA  ATT TTA ATA  AAT ATT           890
                  Met Asp  Leu Leu Asn  Ser Asp Ile  Ile Leu Ile  Asn Ile
                   1           5                         10

TTA AAA TAT   TAT AAT  TTA AAA AAA  ATA ATA ATA  AAC AGA GAT  AAT GTT             938
```

| | | | | | | | | | | | | | | | | |
|---|---|---|---|---|---|---|---|---|---|---|---|---|---|---|---|---|
| Leu | Lys | Tyr | Tyr | Asn | Leu | Lys | Lys | Ile | Ile | Ile | Asn | Arg | Asp | Asn | Val | |
| | 15 | | | | | 20 | | | | 25 | | | | | | |
| ATT | AAT | ATT | AAT | ATA | TTA | AAA | AAA | TTA | GTT | AAT | TTA | GAA | GAA | TTG | CAT | 986 |
| Ile | Asn | Ile | Asn | Ile | Leu | Lys | Lys | Leu | Val | Asn | Leu | Glu | Glu | Leu | His | |
| 30 | | | | | 35 | | | | 40 | | | | | 45 | | |
| ATA | ATA | TAT | TAT | GAT | AAT | AAT | ATT | TTA | AAT | AAT | ATT | CCA | GAA | AAT | ATT | 1034 |
| Ile | Ile | Tyr | Tyr | Asp | Asn | Asn | Ile | Leu | Asn | Asn | Ile | Pro | Glu | Asn | Ile | |
| | | | | 50 | | | | 55 | | | | | 60 | | | |
| AAA | AGT | TTA | TAT | ATT | TCA | AAT | TTA | AAT | ATT | ATT | AAT | TTA | AAT | TTT | ATA | 1082 |
| Lys | Ser | Leu | Tyr | Ile | Ser | Asn | Leu | Asn | Ile | Ile | Asn | Leu | Asn | Phe | Ile | |
| | | | 65 | | | | | 70 | | | | | 75 | | | |
| ACA | AAA | TTA | AAA | AAT | ATA | ACA | TAT | TTA | GAT | ATA | TCT | TAT | AAC | AAA | AAT | 1130 |
| Thr | Lys | Leu | Lys | Asn | Ile | Thr | Tyr | Leu | Asp | Ile | Ser | Tyr | Asn | Lys | Asn | |
| | | 80 | | | | | 85 | | | | | 90 | | | | |
| AGC | AAT | ATA | AGT | AAT | ATT | ATA | CTA | CCA | CAT | TCT | ATA | GAA | TTT | TTA | AAT | 1178 |
| Ser | Asn | Ile | Ser | Asn | Ile | Ile | Leu | Pro | His | Ser | Ile | Glu | Phe | Leu | Asn | |
| | 95 | | | | | 100 | | | | | 105 | | | | | |
| TGT | GAA | TCA | TGT | AAT | ATA | AAT | GAC | TAT | AAT | TTT | ATT | AAT | AAT | TTA | GTA | 1226 |
| Cys | Glu | Ser | Cys | Asn | Ile | Asn | Asp | Tyr | Asn | Phe | Ile | Asn | Asn | Leu | Val | |
| 110 | | | | | 115 | | | | 120 | | | | | 125 | | |
| AAT | TTA | AAA | AAA | TTA | ATA | ATA | TCT | AAA | AAT | AAA | TTT | GGT | AAC | TTT | AAT | 1274 |
| Asn | Leu | Lys | Lys | Leu | Ile | Ile | Ser | Lys | Asn | Lys | Phe | Gly | Asn | Phe | Asn | |
| | | | | 130 | | | | 135 | | | | | 140 | | | |
| AAT | GTT | TTT | CCT | ATT | AGT | ATA | GTT | GAG | TTA | AAT | ATG | GAA | TCA | ATA | CAA | 1322 |
| Asn | Val | Phe | Pro | Ile | Ser | Ile | Val | Glu | Leu | Asn | Met | Glu | Ser | Ile | Gln | |
| | | | 145 | | | | | 150 | | | | | 155 | | | |
| ATA | AAA | GAT | TAT | AAA | TTT | ATA | GAA | AAA | TTA | ATT | AAT | TTA | AAA | AAA | TTA | 1370 |
| Ile | Lys | Asp | Tyr | Lys | Phe | Ile | Glu | Lys | Leu | Ile | Asn | Leu | Lys | Lys | Leu | |
| | | 160 | | | | | 165 | | | | | 170 | | | | |
| GAT | ATA | TCT | TTC | AAT | GTT | AAA | AAA | AAT | ATA | CAT | TTG | ATA | AAA | TTT | | 1418 |
| Asp | Ile | Ser | Phe | Asn | Val | Lys | Lys | Asn | Ile | His | Leu | Ile | Lys | Phe | | |
| | 175 | | | | | 180 | | | | | 185 | | | | | |
| CCA | AAA | AGT | ATA | ACT | CAT | TTA | TGT | GAT | TAT | CAA | TCA | TAT | AAA | GAA | AAT | 1466 |
| Pro | Lys | Ser | Ile | Thr | His | Leu | Cys | Asp | Tyr | Gln | Ser | Tyr | Lys | Glu | Asn | |
| 190 | | | | | 195 | | | | 200 | | | | | 205 | | |
| TAT | AAT | TAT | TTA | AAA | AAT | TTA | TCA | AAT | ATA | ATT | GAA | TAT | GAA | TTC | | 1511 |
| Tyr | Asn | Tyr | Leu | Lys | Asn | Leu | Ser | Asn | Ile | Ile | Glu | Tyr | Glu | Phe | | |
| | | | | 210 | | | | 215 | | | | | 220 | | | |

( 2 ) INFORMATION FOR SEQ ID NO:9:

( i ) SEQUENCE CHARACTERISTICS:
        ( A ) LENGTH: 66 amino acids
        ( B ) TYPE: amino acid
        ( D ) TOPOLOGY: linear ( i i ) MOLECULE TYPE: protein ( x i ) SEQUENCE DESCRIPTION: SEQ ID NO:9:

| | | | | | | | | | | | | | | |
|---|---|---|---|---|---|---|---|---|---|---|---|---|---|---|
| Met | Gln | Asn | Asn | Asp | Asn | Tyr | Tyr | Ser | Asp | Ile | Glu | Gly | Ala | Lys | Ser |
| 1 | | | | 5 | | | | | 10 | | | | | 15 | |
| Asp | Ile | Ser | Leu | Val | Asp | Arg | Lys | Lys | Lys | Ile | Gly | Lys | Met | Ile | Asn |
| | | | 20 | | | | | 25 | | | | | 30 | | |
| Asn | Ile | Val | Asn | Ile | Asn | Asn | Glu | Leu | Asn | Lys | Gln | Leu | Ser | Asn | Asn |
| | | 35 | | | | | 40 | | | | | 45 | | | |
| Asn | Lys | Met | Leu | Lys | Asn | Leu | Leu | Asp | Ser | Leu | Lys | Lys | Tyr | Asp | Cys |
| | 50 | | | | | 55 | | | | | 60 | | | | |
| Cys | Leu | | | | | | | | | | | | | | |
| 65 | | | | | | | | | | | | | | | |

( 2 ) INFORMATION FOR SEQ ID NO:10:

(i) SEQUENCE CHARACTERISTICS:
    (A) LENGTH: 182 amino acids
    (B) TYPE: amino acid
    (D) TOPOLOGY: linear (ii) MOLECULE TYPE: protein (xi) SEQUENCE DESCRIPTION: SEQ ID NO:10:

| Met | Ser | Ile | Glu | Leu | Ile | Ile | Gly | Pro | Met | Phe | Ser | Gly | Lys | Thr | Thr |
|---|---|---|---|---|---|---|---|---|---|---|---|---|---|---|---|
| 1 | | | | 5 | | | | | 10 | | | | | 15 | |
| Glu | Leu | Met | Arg | Lys | Ile | Asn | Arg | Tyr | Ile | Leu | Ser | Asn | Gln | Lys | Cys |
| | | | 20 | | | | | 25 | | | | | 30 | | |
| Val | Ile | Ile | Thr | His | Asn | Ile | Asp | Asn | Arg | Phe | Ile | Asn | Lys | Asn | Ile |
| | | | 35 | | | | 40 | | | | | 45 | | | |
| Ile | Asn | His | Asp | Gly | Asn | Ile | Leu | Asn | Lys | Glu | Tyr | Leu | Tyr | Ile | Lys |
| | 50 | | | | | 55 | | | | | 60 | | | | |
| Thr | Asn | Asn | Leu | Ile | Asn | Glu | Ile | Asn | Ile | Val | Asp | Asn | Tyr | Asp | Ile |
| 65 | | | | | 70 | | | | 75 | | | | | | 80 |
| Ile | Gly | Ile | Asp | Glu | Cys | Gln | Phe | Phe | Glu | Glu | Asn | Asp | Leu | Glu | Gln |
| | | | | 85 | | | | | 90 | | | | | 95 | |
| Phe | Cys | Asp | Lys | Met | Ala | Asn | Asn | Lys | Lys | Lys | Val | Ile | Val | Ala | Gly |
| | | | 100 | | | | | 105 | | | | | 110 | | |
| Leu | Asn | Cys | Asp | Phe | Asn | Arg | Asn | Ile | Phe | Asn | Ser | Ile | Ser | Lys | Leu |
| | | | 115 | | | | 120 | | | | | 125 | | | |
| Ile | Pro | Lys | Val | Glu | Lys | Ile | Lys | Lys | Leu | Gln | Ala | Ile | Cys | Gln | Phe |
| | | 130 | | | | | 135 | | | | | 140 | | | |
| Cys | Tyr | Lys | Asp | Ala | Ser | Phe | Thr | Ile | Lys | Lys | His | Asn | Lys | Asn | Gln |
| 145 | | | | | 150 | | | | | 155 | | | | | 160 |
| Ile | Ile | Glu | Ile | Gly | Gly | Gln | Asp | Leu | Tyr | Val | Pro | Val | Cys | Arg | Leu |
| | | | | 165 | | | | | 170 | | | | | 175 | |
| Cys | Tyr | Asn | Asn | Ser | Tyr |
| | | | | 180 | |

(2) INFORMATION FOR SEQ ID NO:11:

(i) SEQUENCE CHARACTERISTICS:
    (A) LENGTH: 220 amino acids
    (B) TYPE: amino acid
    (D) TOPOLOGY: linear (ii) MOLECULE TYPE: protein (xi) SEQUENCE DESCRIPTION: SEQ ID NO:11:

| Met | Asp | Leu | Leu | Asn | Ser | Asp | Ile | Ile | Leu | Ile | Asn | Ile | Leu | Lys | Tyr |
|---|---|---|---|---|---|---|---|---|---|---|---|---|---|---|---|
| 1 | | | | 5 | | | | | 10 | | | | | 15 | |
| Tyr | Asn | Leu | Lys | Lys | Ile | Ile | Ile | Asn | Arg | Asp | Asn | Val | Ile | Asn | Ile |
| | | | 20 | | | | | 25 | | | | | 30 | | |
| Asn | Ile | Leu | Lys | Lys | Leu | Val | Asn | Leu | Glu | Glu | Leu | His | Ile | Ile | Tyr |
| | | | 35 | | | | 40 | | | | | 45 | | | |
| Tyr | Asp | Asn | Asn | Ile | Leu | Asn | Asn | Ile | Pro | Glu | Asn | Ile | Lys | Ser | Leu |
| | 50 | | | | | 55 | | | | | 60 | | | | |
| Tyr | Ile | Ser | Asn | Leu | Asn | Ile | Ile | Asn | Leu | Asn | Phe | Ile | Thr | Lys | Leu |
| 65 | | | | | 70 | | | | | 75 | | | | | 80 |
| Lys | Asn | Ile | Thr | Tyr | Leu | Asp | Ile | Ser | Tyr | Asn | Lys | Asn | Ser | Asn | Ile |
| | | | | 85 | | | | | 90 | | | | | 95 | |
| Ser | Asn | Ile | Ile | Leu | Pro | His | Ser | Ile | Glu | Phe | Leu | Asn | Cys | Glu | Ser |
| | | | | 100 | | | | | 105 | | | | | 110 | |
| Cys | Asn | Ile | Asn | Asp | Tyr | Asn | Phe | Ile | Asn | Asn | Leu | Val | Asn | Leu | Lys |

|   |   |   | 115 |   |   |   |   | 120 |   |   |   | 125 |   |   |
|---|---|---|---|---|---|---|---|---|---|---|---|---|---|---|
| Lys | Leu | Ile | Ile | Ser | Lys | Asn | Lys | Phe | Gly | Asn | Phe | Asn | Asn | Val | Phe |
|   | 130 |   |   |   | 135 |   |   |   |   | 140 |   |   |   |   |

```
            115                         120                         125
Lys Leu Ile Ile Ser Lys Asn Lys Phe Gly Asn Phe Asn Asn Val Phe
        130                 135                 140

Pro Ile Ser Ile Val Glu Leu Asn Met Glu Ser Ile Gln Ile Lys Asp
145                 150                 155                     160

Tyr Lys Phe Ile Glu Lys Leu Ile Asn Leu Lys Lys Leu Asp Ile Ser
                165                 170                 175

Phe Asn Val Lys Lys Asn Asn Ile His Leu Ile Lys Phe Pro Lys Ser
            180                 185                 190

Ile Thr His Leu Cys Asp Tyr Gln Ser Tyr Lys Glu Asn Tyr Asn Tyr
        195                 200                 205

Leu Lys Asn Leu Ser Asn Ile Ile Glu Tyr Glu Phe
210                 215                 220
```

( 2 ) INFORMATION FOR SEQ ID NO:12:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:12:

GARGTNGAYC CNGARTAYGT                                                       20

( 2 ) INFORMATION FOR SEQ ID NO:13:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:13:

TTTCAAATTA ACTGGCAACC                                                       20

( 2 ) INFORMATION FOR SEQ ID NO:14:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:14:

GGGATGGATT TTAGATTGCG                                                       20

( 2 ) INFORMATION FOR SEQ ID NO:15:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:15:

GCCTGGTTGG GTAACACCTC                                                       20

( 2 ) INFORMATION FOR SEQ ID NO:16:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:16:

CTGCTAGATT ATCTACTCCG        20

( 2 ) INFORMATION FOR SEQ ID NO:17:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:17:

GTTCGAAACA AGTATTTTCA TCTTTTAAAT AAATC        35

( 2 ) INFORMATION FOR SEQ ID NO:18:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:18:

GA Y GARGGRG GRCARTT Y TT        20

( 2 ) INFORMATION FOR SEQ ID NO:19:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:19:

GGNCCCATGT T Y TCNGG        17

( 2 ) INFORMATION FOR SEQ ID NO:20:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:20:

GGTGCAAAAT CTGATATTTC        20

( 2 ) INFORMATION FOR SEQ ID NO:21:

( i ) SEQUENCE CHARACTERISTICS:
        ( A ) LENGTH: 3012 base pairs (B) TYPE: nucleic acid
(C) STRANDEDNESS: double
(D) TOPOLOGY: unknown (ii) MOLECULE TYPE: DNA (genomic)

(xi) SEQUENCE DESCRIPTION: SEQ ID NO:21:

| | | | | | | |
|---|---|---|---|---|---|---|
| ATGAGTAACG | TACCTTTAGC | AACCAAAACA | ATAAGAAAAT | TATCAAATCG | AAAATATGAA | 60 |
| ATAAAGATTT | ATTTAAAAGA | TGAAAATACT | TGTTTCGAAC | GTGTAGTAGA | TATGGTAGTT | 120 |
| CCATTATATG | ATGTGTGTAA | TGAAACTTCT | GGTGTTACTT | TAGAATCATG | TAGTCCAAAT | 180 |
| ATAGAAGTAA | TTGAATTAGA | CAATACTCAT | GTTAGAATCA | AAGTTCACGG | CGATACATTA | 240 |
| AAAGAAATGT | GTTTTGAATT | ATTGTTCCCG | TGTAATGTAA | ACGAAGCCCA | AGTATGGAAA | 300 |
| TATGTAAGTC | GATTATTGCT | AGATAATGTA | TCACATAATG | ACGTAAAATA | TAAATTAGCT | 360 |
| AATTTTAGAC | TGACTCTTAA | TGGAAAACAT | TTAAAATTAA | AAGAAATCGA | TCAACCGCTA | 420 |
| TTTATTTATT | TTGTCGATGA | TTTGGGAAAT | TATGGATTAA | TTACTAAGGA | AAATATTCAA | 480 |
| AATAATAATT | TACAAGTTAA | CAAAGATGCA | TCATTTATTA | CTATATTTCC | ACAATATGCG | 540 |
| TATATTTGTT | TAGGTAGAAA | AGTATATTTA | AATGAAAAAG | TAACTTTTGA | TGTAACTACA | 600 |
| GATGCAACTA | ATATTACTTT | AGATTTAAT | AAATCTGTTA | ATATCGCAGT | ATCATTCCTT | 660 |
| GATATATATT | ACGAAGTTAA | TAATAATGAA | CAAAAGATT | TATTAAAAGA | TTTACTTAAG | 720 |
| AGATACGGTG | AATTTGAAGT | CTATAACGCA | GATACTGGAT | TAATTTATGC | TAAAAATCTA | 780 |
| AGTATTAAAA | ATTATGATAC | TGTGATTCAA | GTAGAAAGGT | TGCCAGTTAA | TTTGAAAGTT | 840 |
| AGAGCATATA | CTAAGGATGA | AAATGGTCGC | AATCTATGTT | TGATGAAAAT | AACATCTAGT | 900 |
| ACAGAAGTAG | ACCCCGAGTA | TGTAACTAGT | AATAATGCTT | TATTGGGTAC | GCTCAGAGTA | 960 |
| TATAAAAAGT | TTGATAAATC | TCATTTAAAA | ATTGTAATGC | ATAACAGAGG | AAGTGGTAAT | 1020 |
| GTATTTCCAT | TAAGATCATT | ATATCTGGAA | TTGTCTAATG | TAAAAGGATA | TCCAGTTAAA | 1080 |
| GCATCTGATA | CTTCGAGATT | AGATGTTGGT | ATTTACAAAT | TAAATAAAAT | TTATGTAGAT | 1140 |
| AACGACGAAA | ATAAAATTAT | ATTGGAAGAA | ATTGAAGCAG | AATATAGATG | CGGAAGACAA | 1200 |
| GTATTCCACG | AACGTGTAAA | ACTTAATAAA | CACCAATGTA | AATATACTCC | CAAATGTCCA | 1260 |
| TTCCAATTTG | TTGTAAACAG | CCCAGATACT | ACGATTCACT | TATATGGTAT | TTCTAATGTT | 1320 |
| TGTTTAAAAC | CTAAAGTACC | CAAAAATTTA | AGACTTTGGG | GATGGATTTT | AGATTGCGAT | 1380 |
| ACTTCTAGAT | TTATTAAACA | TATGGCTGAT | GGATCTGATG | ATTTAGATCT | TGACGTTAGG | 1440 |
| CTTAATAGAA | ATGATATATG | TTTAAAACAA | GCCATAAAAC | AACATTATAC | TAATGTAATT | 1500 |
| ATATTAGAGT | ACGCAAATAC | ATATCCAAAT | TGCACATTAT | CATTGGGTAA | TAATAGATTT | 1560 |
| AATAATGTAT | TTGATATGAA | TGATAACAAA | ACTATATCTG | AGTATACTAA | CTTTACAAAA | 1620 |
| AGTAGACAAG | ACCTTAATAA | CATGTCATGT | ATATTAGGAA | TAAACATAGG | TAATTCCGTA | 1680 |
| AATATTAGTA | GTTTGCCTGG | TTGGGTAACA | CCTCACGAAG | CTAAAATTCT | AAGATCTGGT | 1740 |
| TGTGCTAGAG | TTAGAGAATT | TTGTAAATCA | TTCTGTGATC | TTTCTAATAA | GAGATTCTAT | 1800 |
| GCTATGGCTA | GAGATCTCGT | AAGTTTACTA | TTTATGTGTA | ACTATGTTAA | TATTGAAATT | 1860 |
| AACGAAGCAG | TATGCGAATA | TCCTGGATAT | GTCATATTAT | TCGCAAGAGC | TATTAAAGTA | 1920 |
| ATTAATGATT | TATTATTAAT | TAACGGAGTA | GATAATCTAG | CAGGATATTC | AATTTCCTTA | 1980 |
| CCTATACATT | ATGGATCTAC | TGAAAAGACT | CTACCAAATG | AAAAGTATGG | TGGTGTTGAT | 2040 |
| AAGAAATTTA | AATATCTATT | CTTAAAGAAT | AAACTAAAAG | ATTTAATGCG | TGATGCTGAT | 2100 |
| TTTGTCCAAC | CTCCATTATA | TATTTCTACT | TACTTTAGAA | CTTTATTGGA | TGCTCCACCA | 2160 |

| ACTGATAATT | ATGAAAAATA | TTTGGTTGAT | TCGTCCGTAC | AATCACAAGA | TGTTCTACAG | 2220 |
| --- | --- | --- | --- | --- | --- | --- |
| GGTCTGTTGA | ATACATGTAA | TACTATTGAT | ACTAATGCTA | GAGTTGCATC | AAGTGTTATT | 2280 |
| GGATATGTTT | ATGAACCATG | CGGAACATCA | GAACATAAAA | TTGGTTCAGA | AGCATTGTGT | 2340 |
| AAAATGGCTA | AAGAAGCATC | TAGATTAGGA | AATCTAGGTT | TAGTAAATCG | TATTAATGAA | 2400 |
| AGTAATTACA | ACAAATGTAA | TAAATATGGT | TATAGAGGAG | TATACGAAAA | TAACAAACTA | 2460 |
| AAAACAAAAT | ATTATAGAGA | AATATTTGAT | TGTAATCCTA | ATAATAATAA | TGAATTAATA | 2520 |
| TCCAGATATG | GATATAGAAT | AATGGATTTA | CATAAAATTG | GAGAAATTTT | TGCAAATTAC | 2580 |
| GATGAAAGTG | AATCTCCTTG | CGAACGAAGA | TGTCATTACT | TGGAAGATAG | AGGTCTTTTA | 2640 |
| TATGGTCCTG | AATATGTACA | TCACAGATAT | CAAGAATCAT | GTACGCCTAA | TACGTTTGGA | 2700 |
| AATAACACAA | ATTGTGTAAC | AAGAAATGGT | GAACAACACG | TATACGAAAA | TAGTTGTGGA | 2760 |
| GATAATGCAA | CATGTGGAAG | AAGAACAGGA | TATGGAAGAA | GAAGTAGGGA | TGAATGGAAT | 2820 |
| GACTATAGAA | AACCCCACGT | TTATGACAAT | TGTGCCGATG | CAAATAGTTC | ATCTTCAGAT | 2880 |
| AGCTGTTCAG | ACAGTAGTAG | TAGTAGTGAA | TCTGAATCTG | ATTCAGATGG | ATGTTGCGAC | 2940 |
| ACAGATGCTA | GTTAGATTC | TGATATTGAA | AATTGTTATC | AAAATCCATC | AAAATGTGAT | 3000 |
| GCAGGATGCT | AA | | | | | 3012 |

( 2 ) INFORMATION FOR SEQ ID NO:22:

( i ) SEQUENCE CHARACTERISTICS:
        ( A ) LENGTH: 419 base pairs
        ( B ) TYPE: nucleic acid
        ( C ) STRANDEDNESS: double
        ( D ) TOPOLOGY: unknown ( i i ) MOLECULE TYPE: DNA (genomic)

( x i ) SEQUENCE DESCRIPTION: SEQ ID NO:22:

| TCAACTAATA | ATAATATATT | TTATGCAGTT | TCAACTTTTG | GATTTTAAG | TACAGAAAGT | 60 |
| --- | --- | --- | --- | --- | --- | --- |
| ACTGGTATTA | ATTAACATA | TACAAATTCT | AGAGATTGTA | TTATAGATT | ATTTCTAGA | 120 |
| ATTATAAAAA | TAGTATATGA | TCCTTGTACT | GTCGAAACAT | CTAACGATTG | TAGATTATTA | 180 |
| AGATTATTGA | TGGCCAATAC | ATCATAAATA | CATTATAATA | TTATTATAAT | ATCAATCATA | 240 |
| ATTTTTATAT | ATATTTTATC | TAAAAGGACT | TTTTATTTTT | TATATATTAA | TAATAATAAA | 300 |
| TGAGTAACGT | ACCTTTAGCA | ACCAAAACAA | TAAGAAAATT | ATCAAATCGA | AAATATGAAA | 360 |
| TAAAGATTTA | TTTAAAAGAT | GAAAATACTT | GTTCGAACG | TGTAGTAGAT | ATGGTAGTT | 419 |

( 2 ) INFORMATION FOR SEQ ID NO:23:

( i ) SEQUENCE CHARACTERISTICS:
        ( A ) LENGTH: 678 base pairs
        ( B ) TYPE: nucleic acid
        ( C ) STRANDEDNESS: double
        ( D ) TOPOLOGY: unknown ( i i ) MOLECULE TYPE: DNA (genomic)

( x i ) SEQUENCE DESCRIPTION: SEQ ID NO:23:

| ATGTTTCTAG | TTTATTTCAA | TACATTTTTA | ATAATAATTT | TATTATTTGG | TATTATAGGT | 60 |
| --- | --- | --- | --- | --- | --- | --- |
| ATTTATATAT | TAACATTTGT | GTTAATATA | GATTTTTTAA | TAAATAATAA | TAAAATATAT | 120 |
| ATATTATCAT | ATAACGCAAC | TAATATAAAC | AATATAAATA | ATTTAAATTT | ATACGATTAT | 180 |
| TCAGATATTA | TATTTTTGAC | AAATTTTAAC | ATAAATAATA | ATCTTTTAGT | AACACAAGCT | 240 |
| AATAATTTAC | AAGATATACC | AATATTTAAT | GTAAATAATA | TTATATCTAA | TCAATATAAT | 300 |

```
TTTTATTCAG CGTCTAGTAA TAATGTAAAT ATATTATTAG GATTAAGAAA AACATTAAAT     360

ATAAATAGAA ATCCATTTTT ATTATTTAGA AATACATCTC TAGCTATAGT TTTCAATAAT     420

AATGAAACTT TTCACTGTTA TATAAGTTCA AATCAAAATA GTGATGTATT AGATATAGTA     480

TCACATATAG AATTTATGAA ATCTAGATAT AATAAATATG TAATTATAGG AGAAATACCC     540

GTAAATAATA ATATATCTAT TAATAATATA TTAAATAATT TTGCTATTAT AACTAATGTG     600

AGATTAATAG ATAAATATAA CTCTATAATA TCATTTTTAA ATATCAACGT AGGAACACTT     660

TTTGTCATAA ATCCATAA                                                  678
```

( 2 ) INFORMATION FOR SEQ ID NO:24:

( i ) SEQUENCE CHARACTERISTICS:
        ( A ) LENGTH: 486 base pairs
        ( B ) TYPE: nucleic acid
        ( C ) STRANDEDNESS: double
        ( D ) TOPOLOGY: unknown ( i i ) MOLECULE TYPE: DNA (genomic)

( x i ) SEQUENCE DESCRIPTION: SEQ ID NO:24:

```
ATGTCAATAT TTATCTACTA TATTTCAAC AATAGATTTT ATATATATAA AAGAATGAAT      60

ACTGTACAAA TTTTAGTTGT CATATTAATA ACAACAGCAT TATCTTTTCT AGTTTTTCAA    120

TTATGGTATT ATGCCGAAAA TTACGAATAT ATATTAAGAT ATAATGATAC ATATTCAAAT    180

TTACAATTTG CGAGAAGCGC AAATATAAAT TTTGATGATT TAACTGTTTT TGATCCCAAC    240

GATAATGTTT TAATGTTGA AGAAAAATGG CGCTGTGCTT CAACTAATAA TAATATATTT     300

TATGCAGTTT CAACTTTTGG ATTTTAAGT ACAGAAAGTA CTGGTATTAA TTAACATAT      360

ACAAATTCTA GAGATTGTAT TATAGATTTA TTTTCTAGAA TTATAAAAAT AGTATATGAT    420

CCTTGTACTG TCGAAACATC TAACGATTGT AGATTATTAA GATTATTGAT GGCCAATACA    480

TCATAA                                                               486
```

( 2 ) INFORMATION FOR SEQ ID NO:25:

( i ) SEQUENCE CHARACTERISTICS:
        ( A ) LENGTH: 1395 base pairs
        ( B ) TYPE: nucleic acid
        ( C ) STRANDEDNESS: double
        ( D ) TOPOLOGY: unknown ( i i ) MOLECULE TYPE: DNA (genomic)

( x i ) SEQUENCE DESCRIPTION: SEQ ID NO:25:

```
TTAAATATTA GATTCTAAAC TATTCTTCTC ATTATCAATA TAACTATCAT AATCATTTTT     60

TATTTTACTA CATACATTCA TAATTCTATT ACTATTTTT TTATACATAT CTATTAATTC    120

CATAAACTTT TTATTTTTA TATTAAATAT TTCTAATGTA TTTTTAAATT CGTCAATACT    180

ATTAATATCA TATCTAGAAA TAAATAATGC ACCTCTATAA CTACTAGCCA ATAAATCACC    240

AATAAAACTC ATAGAATAAT ATAATTTTTT AAATTCAAAT TTAGATTTTA TGTTGAAATA    300

AACTATATAA TATAAAAATA TTATATTAAA CATACCACAA TCGGGACTAT CATATTGTAA    360

TTCAAAAGTA TTAAAAAAGT AATAATTTAC ATTTTTAAAT ATATCATTTA AATATTCTGA    420

TAGTACATCA ATGTATAAAT AAGCATAATT AGTATTAGGA GTACTATTGT AGTGTTTATG    480

GCTTTTTATA GTCATATCAG ATTCAATAAA CATATATTTT TTATTTGTT TTATAAGTTC     540

TGGTATATAA CCACTACTAT TAAAAAGTA TGCAGCTTTT TTATCTTTAT CAAAGTGTTT     600

ATCTATTACG CAACAAGTAA AATGATCATT ATAAATTATA GGAAACATAA AAAATCTTTT    660
```

```
TTTATCATTC  ATTAAAAAAA  ATTTTACTCT  ATCTTCAAGT  TTATAGCATC  TCATAGATGA      720

AGCTACTGTA  GCAATATTTT  TATCAGTTTT  TTCAAATAAA  ATCAAATGAA  AATAATCATA      780

ATCTGTATTA  ATCATAGTTA  ATGGATATAT  ACAATTATAT  ATATCTCCCG  AACTTAACCA      840

TGTAGATTTA  TCATGTTTTC  TTGGGTAAGC  TTTAGGTTTA  GGATTAAATC  CCAAAGGCGG      900

TATTCCTATT  TGAGCATCCA  AATCATCATA  AATTGTGGCA  AATGTAGAAA  AATCTCTTGT      960

TTTGGATAAT  TCTGATTTTA  GAAAAGACTT  TCTCATATAT  ACTAATGGAA  TGCCTTTATA     1020

TTTTTTAGAT  GTAATAAAAG  TATTAATATT  TATATTTTA   TCTTGTAAAT  ATTTTTTAT     1080

AGTCCAAAAT  AGAAAAAATT  TTCTTTTAAT  ATTATTTTCA  AAATTAATAT  TATTAATATG     1140

ATTTGGATCT  AAAACTAATT  CATTATATAA  TATTTCCAAG  TATTTTATAG  GTATAAATGT     1200

TACTTTACCT  CTTGTTTCAT  CATCATCATC  TATTTTTTCT  AATATAGCTA  TATTTGCATT     1260

AGTATTATAT  TAATAGGAT   TTATAAAATA  TACCATATTA  TCTATTTTAC  TAAAAAATAA     1320

CATAGACATA  AAATTAATAC  CAGATTCTGG  CATTTTAAA   TTTTATTTG   GAAATCTTCT     1380

AATTTTATTA  TTCAT                                                          1395
```

( 2 ) INFORMATION FOR SEQ ID NO:26:

( i ) SEQUENCE CHARACTERISTICS:
        ( A ) LENGTH: 237 base pairs
        ( B ) TYPE: nucleic acid
        ( C ) STRANDEDNESS: double
        ( D ) TOPOLOGY: unknown ( i i ) MOLECULE TYPE: DNA (genomic)

( x i ) SEQUENCE DESCRIPTION: SEQ ID NO:26:

```
TTATTTTTTT  TTTTGCTTT   TAGGTATAAT  TTACCTTCT   AAACGTTTAT  CTCCCCAAAC       60

ATCTACAGTA  GATGGTTTAT  TAGATTCTGT  GTTATACACA  TCTGCTGGAT  TTGCGGCATT      120

TGTATCCAAA  CCATAATATC  CAGGTCTATA  ATTATCTTTA  AAAACTTGGG  ATTGAGATAC      180

TTCTTCAGTT  TTTAAATTAT  TAAAATATCC  AAGATTATTT  TTTTTGATG   AAGACAT         237
```

( 2 ) INFORMATION FOR SEQ ID NO:27:

( i ) SEQUENCE CHARACTERISTICS:
        ( A ) LENGTH: 492 base pairs
        ( B ) TYPE: nucleic acid
        ( C ) STRANDEDNESS: double
        ( D ) TOPOLOGY: unknown ( i i ) MOLECULE TYPE: DNA (genomic)

( x i ) SEQUENCE DESCRIPTION: SEQ ID NO:27:

```
CTATTCATAA  TAATCATCTG  CTATATATAT  TAATGTATCA  TTCTCTATTA  TAAATATAGG       60

TATATTGTCT  TTATCAATCA  TTAATTTTGC  TACAGCTGTA  TTATCTTTAT  ATACTATATT      120

TGTGTCTTTG  TTTAATAAAC  CTTTTAATAT  AGTGGCTCTA  TCATAATCTT  TACAATATGA      180

TATGGGATAT  AATTTATAT   TAATAATAAC  ATTAGATACG  TTCATTTCTT  TCATTCTAGT      240

TTTACGTATT  GTGTCAAAAA  TTATTTCATT  TTCTGCTGGT  TCTATATATT  TATATGTGTT      300

ATGAATAGAT  TCGATAGATG  ATGATTTAA   TAAATCAAAT  ATAACATTTA  TTTTACCTTG      360

TTTATCTTTT  ATAATATCTA  ATATTTCTTT  ATCTACAGAT  TTTCTGTTGT  TGGTATATGA      420

TATTAAAAAA  TGAACGTTAA  CATATCTATA  TTCTTGTGGT  AAATCTTTAT  GAGAATTTAA      480

TCTTATAGAT  CT                                                              492
```

( 2 ) INFORMATION FOR SEQ ID NO:28:

( i ) SEQUENCE CHARACTERISTICS:
 ( A ) LENGTH: 549 base pairs
 ( B ) TYPE: nucleic acid
 ( C ) STRANDEDNESS: double
 ( D ) TOPOLOGY: unknown ( i i ) MOLECULE TYPE: DNA (genomic)

( x i ) SEQUENCE DESCRIPTION: SEQ ID NO:28:

```
TTAATATGAA TTATTATAAC ATAATCTACA CACAGGAACA TATAAATCTT GTCCACCTAT    60
TTCAATTATT TGATTTTTAT TATGTTTTTT AATTGTAAAA GAAGCATCTT TATAACAAAA   120
TTGACATATA GCTTGTAATT TTTTATTTT TTCTACTTTA GGAATTAATT TGATATAGA    180
ATTAAATATA TTTCTGTTAA AGTCACAATT TAATCCAGCA ACAATAACTT TTTTTTATT    240
ATTAGCCATT TTATCACAAA ATTGTTCTAA ATCATTTCT TCAAAAAATT GACACTCATC    300
TATGCCAATA ATATCATAAT TATCTACGAT ATTGATTTCA TTAATTAAAT TATTTGTTTT   360
AATGTATAAA TATTCTTTAT TTAATATATT TCCGTCATGA TTTATTATAT TTTTATTTAT   420
AAATCTATTA TCTATATTAT GAGTTATAAT TACACATTTT TGATTAGATA AAATATATCT   480
ATTAATTTTT CGCATCAATT CTGTTGTTTT GCCAGAAAAC ATAGGACCAA TTATTAATTC   540
TATCGACAT                                                          549
```

( 2 ) INFORMATION FOR SEQ ID NO:29:

( i ) SEQUENCE CHARACTERISTICS:
 ( A ) LENGTH: 69 base pairs
 ( B ) TYPE: nucleic acid
 ( C ) STRANDEDNESS: double
 ( D ) TOPOLOGY: unknown ( i i ) MOLECULE TYPE: DNA (genomic)

( x i ) SEQUENCE DESCRIPTION: SEQ ID NO:29:

```
TTTTTTTAT TATTTGATAT ATTTTTTCAA AAAAAAATTA ATCAATGAAA AAAAAATAAA    60
ATTATCAAA                                                           69
```

( 2 ) INFORMATION FOR SEQ ID NO:30:

( i ) SEQUENCE CHARACTERISTICS:
 ( A ) LENGTH: 141 base pairs
 ( B ) TYPE: nucleic acid
 ( C ) STRANDEDNESS: double
 ( D ) TOPOLOGY: unknown ( i i ) MOLECULE TYPE: DNA (genomic)

( x i ) SEQUENCE DESCRIPTION: SEQ ID NO:30:

```
AAACATAGGA CCAATTATTA ATTCTATCGA CATTTTTTTT TATTATTTGA TATATTTTT    60
CAAAAAAAAA TTAATCAATG AAAAAAAAAT AAAATTATCA AAATGGATTT ACTAAATTCT   120
GATATAATTT TAATAAATAT T                                             141
```

( 2 ) INFORMATION FOR SEQ ID NO:31:

( i ) SEQUENCE CHARACTERISTICS:
 ( A ) LENGTH: 201 base pairs
 ( B ) TYPE: nucleic acid
 ( C ) STRANDEDNESS: double
 ( D ) TOPOLOGY: unknown ( i i ) MOLECULE TYPE: DNA (genomic)

( x i ) SEQUENCE DESCRIPTION: SEQ ID NO:31:

```
TTATAAACAA CAATCATATT TTTTTAAAGA ATCTAATAAA TTTTTTAACA TTTTATTATT      60
ATTTGATAAT TGTTTATTTA ATTCGTTATT GATATTAACA ATATTATTTA TCATTTTACC     120
TATTTTTTTT TTTCTATCTA CTAACGAAAT ATCAGATTTT GCACCTTCAA TATCAGAATA     180
ATAATTATCA TTATTTTGCA T                                               201
```

( 2 ) INFORMATION FOR SEQ ID NO:32:

( i ) SEQUENCE CHARACTERISTICS:
        ( A ) LENGTH: 660 base pairs
        ( B ) TYPE: nucleic acid
        ( C ) STRANDEDNESS: double
        ( D ) TOPOLOGY: unknown ( i i ) MOLECULE TYPE: DNA (genomic)

( x i ) SEQUENCE DESCRIPTION: SEQ ID NO:32:

```
ATGGATTTAC TAAATTCTGA TATAATTTTA ATAAATATTT TAAATATTA TAATTTAAAA      60
AAAATAATAA TAAACAGAGA TAATGTTATT AATATTAATA TATTAAAAAA ATTAGTTAAT    120
TTAGAAGAAT TGCATATAAT ATATTATGAT AATAATATTT TAAATAATAT TCCAGAAAAT    180
ATTAAAAGTT TATATATTTC AAATTTAAAT ATTATTAATT TAAATTTTAT AACAAAATTA    240
AAAAATATAA CATATTTAGA TATATCTTAT AACAAAAATA GCAATATAAG TAATATTATA    300
CTACCACATT CTATAGAATT TTTAAATTGT GAATCATGTA ATATAAATGA CTATAATTTT    360
ATTAATAATT TAGTAAATTT AAAAAAATTA ATAATATCTA AAAATAAATT TGGTAACTTT    420
AATAATGTTT TTCCTATTAG TATAGTTGAG TTAAATATGG AATCAATACA AATAAAAGAT    480
TATAAATTTA TAGAAAAATT AATTAATTTA AAAAAATTAG ATATATCTTT CAATGTTAAA    540
AAAAATAATA TACATTTGAT AAAATTTCCA AAAAGTATAA CTCATTTATG TGATTATCAA    600
TCATATAAAG AAAATTATAA TTATTTAAAA AATTTATCAA ATATAATTGA ATATGAATTC    660
```

( 2 ) INFORMATION FOR SEQ ID NO:33:

( i ) SEQUENCE CHARACTERISTICS:
        ( A ) LENGTH: 3907 base pairs
        ( B ) TYPE: nucleic acid
        ( C ) STRANDEDNESS: double
        ( D ) TOPOLOGY: unknown ( i i ) MOLECULE TYPE: DNA (genomic)

( x i ) SEQUENCE DESCRIPTION: SEQ ID NO:33:

```
TTCTAAACGT TTATCTCCCC AAACATCTAC AGTAGATGGT TTATTAGATT CTGTGTTATA      60
CACATCTGCT GGATTTGCGG CATTTGTATC CAAACCATAA TATCCAGGTC TATAATTATC    120
TTTAAAAACT TGGGATTGAG ATACTTCTTC AGTTTTTAAA TTATTAAAAT ATCCAAGATT    180
ATTTTTTTTT GATGAAGACA TAATTGATAT TATAATACTT TATAGATATG TCAATATTTA    240
TCTACTATAT TTTCAACAAT AGATTTTATA TATATAAAAG AATGAATACT GTACAAATTT    300
TAGTTGTCAT ATTAATAACA ACAGCATTAT CTTTTCTAGT TTTTCAATTA TGGTATTATG    360
CCGAAAATTA CGAATATATA TTAAGATATA ATGATACATA TTCAAATTTA CAATTTGCGA    420
GAAGCGCAAA TATAAATTTT GATGATTTAA CTGTTTTTGA TCCCAACGAT AATGTTTTA    480
ATGTTGAAGA AAAATGGCGC TGTGCTTCAA CTAATAATAA TATATTTTAT GCAGTTTCAA    540
CTTTTGGATT TTTAAGTACA GAAAGTACTG GTATTAATTT AACATATACA AATTCTAGAG    600
ATTGTATTAT AGATTTATTT CTAGAATTA TAAAAATAGT ATATGATCCT TGTACTGTCG    660
AAACATCTAA CGATTGTAGA TTATTAAGAT TATTGATGGC CAATACATCA TAAATACATT    720
```

```
ATAATATTAT  TATAATATCA  ATCATAATTT  TTATATATAT  TTTATCTAAA  AGGACTTTTT   780
ATTTTTTATA  TATTAATAAT  AATAAATGAG  TAACGTACCT  TTAGCAACCA  AAACAATAAG   840
AAAATTATCA  AATCGAAAAT  ATGAAATAAA  GATTTATTTA  AAAGATGAAA  ATACTTGTTT   900
CGAACGTGTA  GTAGATATGG  TAGTTCCATT  ATATGATGTG  TGTAATGAAA  CTTCTGGTGT   960
TACTTTAGAA  TCATGTAGTC  CAAATATAGA  AGTAATTGAA  TTAGACAATA  CTCATGTTAG  1020
AATCAAAGTT  CACGGCGATA  CATTAAAAGA  AATGTGTTTT  GAATTATTGT  TCCCGTGTAA  1080
TGTAAACGAA  GCCCAAGTAT  GGAAATATGT  AAGTCGATTA  TTGCTAGATA  ATGTATCACA  1140
TAATGACGTA  AAATATAAAT  TAGCTAATTT  TAGACTGACT  CTTAATGGAA  AACATTTAAA  1200
ATTAAAAGAA  ATCGATCAAC  CGCTATTTAT  TTATTTGTC   GATGATTTGG  GAAATTATGG  1260
ATTAATTACT  AAGGAAAATA  TTCAAAATAA  TAATTTACAA  GTTAACAAAG  ATGCATCATT  1320
TATTACTATA  TTTCCACAAT  ATGCGTATAT  TTGTTTAGGT  AGAAAAGTAT  ATTTAAATGA  1380
AAAAGTAACT  TTTGATGTAA  CTACAGATGC  AACTAATATT  ACTTTAGATT  TTAATAAATC  1440
TGTTAATATC  GCAGTATCAT  TCCTTGATAT  ATATTACGAA  GTAATAATA   ATGAACAAAA  1500
AGATTTATTA  AAAGATTTAC  TTAAGAGATA  CGGTGAATTT  GAAGTCTATA  ACGCAGATAC  1560
TGGATTAATT  TATGCTAAAA  ATCTAAGTAT  TAAAAATTAT  GATACTGTGA  TTCAAGTAGA  1620
AAGGTTGCCA  GTTAATTTGA  AAGTTAGAGC  ATATACTAAG  GATGAAAATG  GTCGCAATCT  1680
ATGTTTGATG  AAAATAACAT  CTAGTACAGA  AGTAGACCCC  GAGTATGTAA  CTAGTAATAA  1740
TGCTTTATTG  GGTACGCTCA  GAGTATATAA  AAAGTTTGAT  AAATCTCATT  TAAAAATTGT  1800
AATGCATAAC  AGAGGAAGTG  GTAATGTATT  TCCATTAAGA  TCATTATATC  TGGAATTGTC  1860
TAATGTAAAA  GGATATCCAG  TTAAAGCATC  TGATACTTCG  AGATTAGATG  TTGGTATTTA  1920
CAAATTAAAT  AAAATTTATG  TAGATAACGA  CGAAAATAAA  ATTATATTGG  AAGAAATTGA  1980
AGCAGAATAT  AGATGCGGAA  GACAAGTATT  CCACGAACGT  GTAAAACTTA  ATAAACACCA  2040
ATGTAAATAT  ACTCCCAAAT  GTCCATTCCA  ATTGTTGTA   AACAGCCCAG  ATACTACGAT  2100
TCACTTATAT  GGTATTTCTA  ATGTTTGTTT  AAAACCTAAA  GTACCCAAAA  ATTTAAGACT  2160
TTGGGGATGG  ATTTTAGATT  GCGATACTTC  TAGATTTATT  AAACATATGG  CTGATGGATC  2220
TGATGATTTA  GATCTTGACG  TTAGGCTTAA  TAGAAATGAT  ATATGTTTAA  AACAAGCCAT  2280
AAAACAACAT  TATACTAATG  TAATTATATT  AGAGTACGCA  AATACATATC  CAAATTGCAC  2340
ATTATCATTG  GGTAATAATA  GATTTAATAA  TGTATTTGAT  ATGAATGATA  ACAAAACTAT  2400
ATCTGAGTAT  ACTAACTTTA  CAAAAAGTAG  ACAAGACCTT  AATAACATGT  CATGTATATT  2460
AGGAATAAAC  ATAGGTAATT  CCGTAAATAT  TAGTAGTTTG  CCTGGTTGGG  TAACACCTCA  2520
CGAAGCTAAA  ATTCTAAGAT  CTGGTTGTGC  TAGAGTTAGA  GAATTTTGTA  AATCATTCTG  2580
TGATCTTTCT  AATAAGAGAT  TCTATGCTAT  GGCTAGAGAT  CTCGTAAGTT  TACTATTTAT  2640
GTGTAACTAT  GTTAATATTG  AAATTAACGA  AGCAGTATGC  GAATATCCTG  GATATGTCAT  2700
ATTATTCGCA  AGAGCTATTA  AAGTAATTAA  TGATTTATTA  TTAATTAACG  GAGTAGATAA  2760
TCTAGCAGGA  TATTCAATTT  CCTTACCTAT  ACATTATGGA  TCTACTGAAA  AGACTCTACC  2820
AAATGAAAAG  TATGGTGGTG  TTGATAAGAA  ATTTAAATAT  CTATTCTTAA  AGAATAAACT  2880
AAAAGATTTA  ATGCGTGATG  CTGATTTTGT  CCAACCTCCA  TTATATATTT  CTACTTACTT  2940
TAGAACTTTA  TTGGATGCTC  CACCAACTGA  TAATTATGAA  AAATATTTGG  TTGATTCGTC  3000
CGTACAATCA  CAAGATGTTC  TACAGGGTCT  GTTGAATACA  TGTAATACTA  TTGATACTAA  3060
TGCTAGAGTT  GCATCAAGTG  TTATTGGATA  TGTTTATGAA  CCATGCGGAA  CATCAGAACA  3120
```

| | | | | | |
|---|---|---|---|---|---|
| TAAAATTGGT | TCAGAAGCAT | TGTGTAAAAT | GGCTAAAGAA | GCATCTAGAT | TAGGAAATCT | 3180 |
| AGGTTTAGTA | AATCGTATTA | ATGAAAGTAA | TTACAACAAA | TGTAATAAAT | ATGGTTATAG | 3240 |
| AGGAGTATAC | GAAAATAACA | AACTAAAAAC | AAAATATTAT | AGAGAAATAT | TTGATTGTAA | 3300 |
| TCCTAATAAT | AATAATGAAT | TAATATCCAG | ATATGGATAT | AGAATAATGG | ATTTACATAA | 3360 |
| AATTGGAGAA | ATTTTTGCAA | ATTACGATGA | AAGTGAATCT | CCTTGCGAAC | GAAGATGTCA | 3420 |
| TTACTTGGAA | GATAGAGGTC | TTTTATATGG | TCCTGAATAT | GTACATCACA | GATATCAAGA | 3480 |
| ATCATGTACG | CCTAATACGT | TTGGAAATAA | CACAAATTGT | GTAACAAGAA | ATGGTGAACA | 3540 |
| ACACGTATAC | GAAAATAGTT | GTGGAGATAA | TGCAACATGT | GGAAGAAGAA | CAGGATATGG | 3600 |
| AAGAAGAAGT | AGGGATGAAT | GGAATGACTA | TAGAAAACCC | CACGTTTATG | ACAATTGTGC | 3660 |
| CGATGCAAAT | AGTTCATCTT | CAGATAGCTG | TTCAGACAGT | AGTAGTAGTA | GTGAATCTGA | 3720 |
| ATCTGATTCA | GATGGATGTT | GCGACACAGA | TGCTAGTTTA | GATTCTGATA | TTGAAAATTG | 3780 |
| TTATCAAAAT | CCATCAAAAT | GTGATGCAGG | ATGCTAAATG | AAATTTAATA | TTATATAATA | 3840 |
| TTAACTTACA | AGTTATAAAA | ATCATTAAAA | TGATTTTTTA | AAATGATATT | ATCGATAGTT | 3900 |
| GTGATAA | | | | | | 3907 |

( 2 ) INFORMATION FOR SEQ ID NO:34:

( i ) SEQUENCE CHARACTERISTICS:
        ( A ) LENGTH: 25 amino acids
        ( B ) TYPE: amino acid
        ( D ) TOPOLOGY: unknown ( i i ) MOLECULE TYPE: protein ( i x ) FEATURE:
        ( A ) NAME/KEY: Region
        ( B ) LOCATION: 3
        ( D ) OTHER INFORMATION: /note= "This amino acid may be
           either Asn or Arg."

( i x ) FEATURE:
        ( A ) NAME/KEY: Region
        ( B ) LOCATION: 12
        ( D ) OTHER INFORMATION: /note= "This amino acid may be
           either Asn or Arg."

( x i ) SEQUENCE DESCRIPTION: SEQ ID NO:34:

Met Ala Xaa Asp Leu Val Ser Leu Leu Phe Met Xaa Xaa Tyr Val Asn
1               5                   10                  15

Ile Glu Ile Asn Glu Ala Val Xaa Glu
            20              25

( 2 ) INFORMATION FOR SEQ ID NO:35:

( i ) SEQUENCE CHARACTERISTICS:
        ( A ) LENGTH: 17 amino acids
        ( B ) TYPE: amino acid
        ( D ) TOPOLOGY: unknown ( i i ) MOLECULE TYPE: peptide ( i x ) FEATURE:
        ( A ) NAME/KEY: Region
        ( B ) LOCATION: 15
        ( D ) OTHER INFORMATION: /note= "This amino acid may be
           either Thr or Ile."

( x i ) SEQUENCE DESCRIPTION: SEQ ID NO:35:

Met Lys Ile Thr Ser Ser Thr Glu Val Asp Pro Glu Tyr Val Xaa Ser
1               5                   10                  15

Asn ( 2 ) INFORMATION FOR SEQ ID NO:36:

( i ) SEQUENCE CHARACTERISTICS:
        ( A ) LENGTH: 8 amino acids
        ( B ) TYPE: amino acid
        ( D ) TOPOLOGY: unknown ( i i ) MOLECULE TYPE: protein ( x i ) SEQUENCE DESCRIPTION: SEQ ID NO:36:

Asn Ala Leu Phe Phe Asn Val Phe
1               5

( 2 ) INFORMATION FOR SEQ ID NO:37:

( i ) SEQUENCE CHARACTERISTICS:
        ( A ) LENGTH: 7 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:37:

Glu Val Asp Pro Glu Tyr Val
1               5

( 2 ) INFORMATION FOR SEQ ID NO:38:

( i ) SEQUENCE CHARACTERISTICS:
        ( A ) LENGTH: 66 base pairs
        ( B ) TYPE: nucleic acid
        ( C ) STRANDEDNESS: double
        ( D ) TOPOLOGY: unknown ( i i ) MOLECULE TYPE: DNA (genomic)

( x i ) SEQUENCE DESCRIPTION: SEQ ID NO:38:

ATGGCTAGAG ATCTCGTAAG TTTACTATTT ATGTGTAACT ATGTTAATAT TGAAATTAAC    60

GAAGCA    66

( 2 ) INFORMATION FOR SEQ ID NO:39:

( i ) SEQUENCE CHARACTERISTICS:
        ( A ) LENGTH: 51 base pairs
        ( B ) TYPE: nucleic acid
        ( C ) STRANDEDNESS: double
        ( D ) TOPOLOGY: unknown ( i i ) MOLECULE TYPE: DNA (genomic)

( x i ) SEQUENCE DESCRIPTION: SEQ ID NO:39:

ATGAAAATAA CATCTAGTAC AGAAGTAGAC CCCGAGTATG TAACTAGTAA T    51

( 2 ) INFORMATION FOR SEQ ID NO:40:

( i ) SEQUENCE CHARACTERISTICS:
        ( A ) LENGTH: 24 base pairs
        ( B ) TYPE: nucleic acid
        ( C ) STRANDEDNESS: double
        ( D ) TOPOLOGY: unknown ( i i ) MOLECULE TYPE: DNA (genomic)

( x i ) SEQUENCE DESCRIPTION: SEQ ID NO:40:

AATAATAGAT TTAATAATGT ATTT    24